(12) United States Patent
Andersen et al.

(10) Patent No.: US 10,916,328 B2
(45) Date of Patent: Feb. 9, 2021

(54) SYSTEMS AND METHODS FOR CELL-CENTRIC SIMULATION AND CELL-BASED MODELS PRODUCED THEREFROM

(75) Inventors: Timothy L. Andersen, Boise, ID (US);
Ullysses A. Eoff, Nampa, ID (US);
Marc G. Footen, Nampa, ID (US);
Richard D. Newman, Meridian, ID (US); Timothy Otter, Caldwell, ID (US); Cap C. Petschulat, Berkeley, CA (US); Mason E. Vail, Nampa, ID (US);
David G. Zuercher, Boise, ID (US)

(73) Assignee: CROWLEY DAVIS RESEARCH, INC., Eagle, CO (US)

( * ) Notice: Subject to any disclaimer, the term of this patent is extended or adjusted under 35 U.S.C. 154(b) by 361 days.

(21) Appl. No.: 12/718,873

(22) Filed: Mar. 5, 2010

(65) Prior Publication Data

US 2010/0305929 A1 Dec. 2, 2010

Related U.S. Application Data

(63) Continuation of application No. PCT/US2008/075514, filed on Sep. 5, 2008, which is a continuation-in-part of application No. 11/899,927, filed on Sep. 7, 2007, now abandoned, said application No. 12/718,873 is a continuation-in-part of application No. 11/899,927, filed on Sep. 7, 2007, now abandoned.

(51) Int. Cl.
*G16B 5/00* (2019.01)
*G16B 45/00* (2019.01)

(52) U.S. Cl.
CPC ........... *G16B 5/00* (2019.02); *G16B 45/00* (2019.02)

(58) Field of Classification Search
None
See application file for complete search history.

(56) References Cited

U.S. PATENT DOCUMENTS

2007/0233441 A1* 10/2007 Crowley, Jr. ............ G16B 5/00 703/11

* cited by examiner

*Primary Examiner* — Lori A. Clow
(74) *Attorney, Agent, or Firm* — Nolte Lackenbach Siegel

(57) ABSTRACT

Systems and methods are provided herein that enable computer-implemented modeling of a biological event. Cell-based models produced from such systems and methods are also disclosed. In some embodiments, systems and methods are provided for cell-centric simulation with accommodating environment feedback. In one embodiment, a computer-implemented method of modeling a biological event can include receiving configurable simulation information and initializing an ontogeny engine to an initial step boundary in accordance with the configurable simulation information. The method can also include advancing the ontogeny engine from a current step boundary to a next step boundary in accordance with the configurable simulation information and the current step boundary. The advancing can include performing a stepCells function. The method can further include continuing the advancing until a halting condition is encountered. In some embodiments, simulation of biological events includes modeling biological processes, such as development of multicellular tissue and differentiation of pluripotent cells.

92 Claims, 48 Drawing Sheets

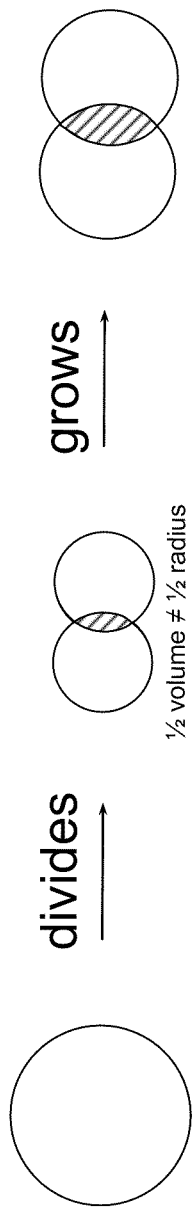
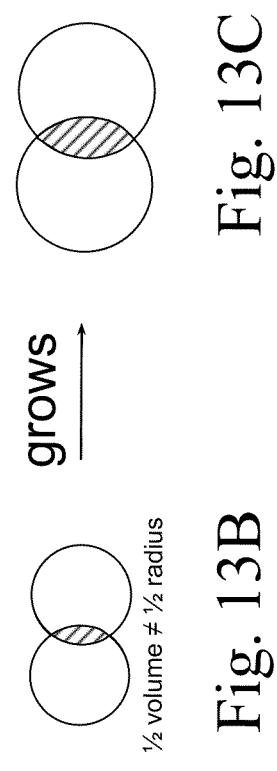
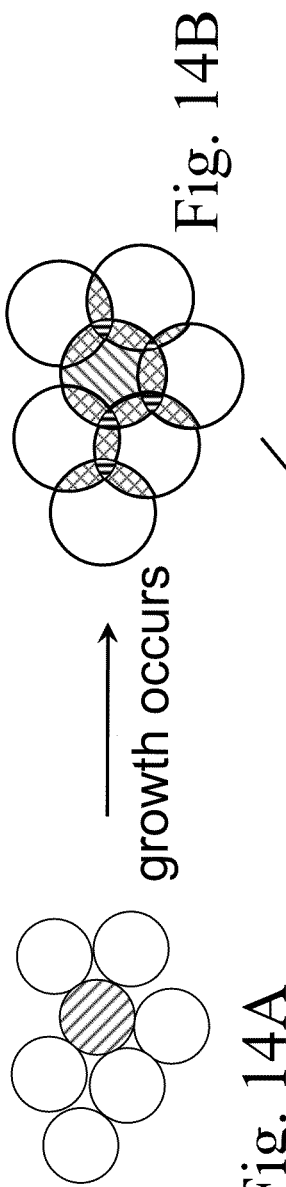
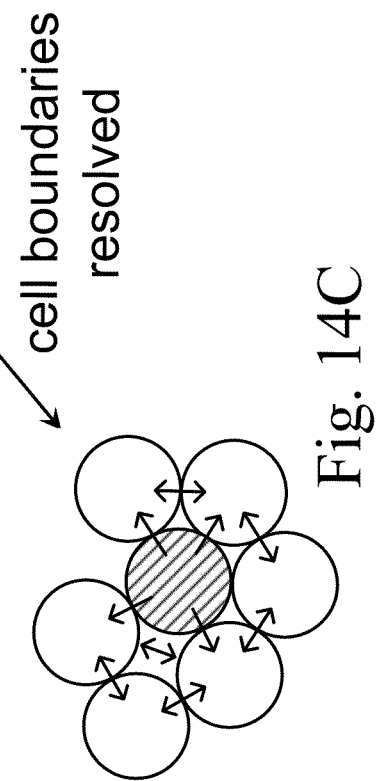
Fig. 13A  Fig. 13B  Fig. 13C
Fig. 14A  Fig. 14B  Fig. 14C diagram from Alberts, et al. Molecular Biology Of The Cell, 4th ed., p. 1264. New York: Garland Science, 2002.

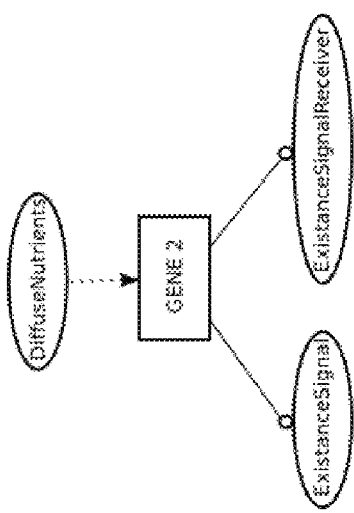
Fig. 24E
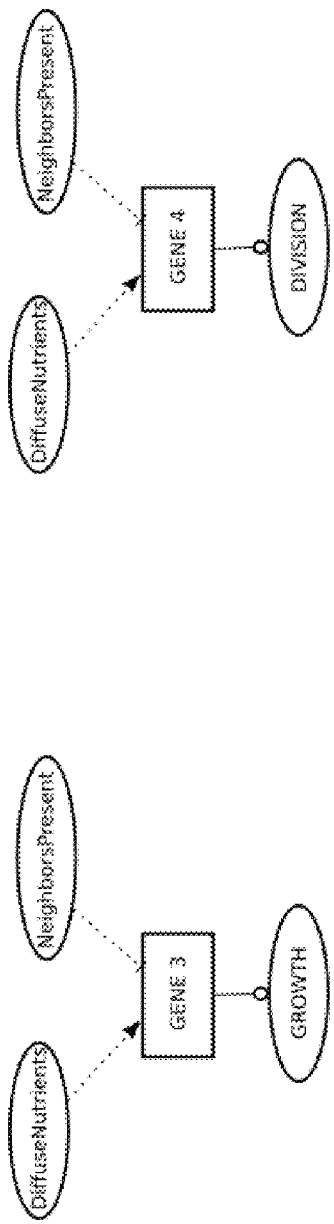
Fig. 24G
Fig. 24F

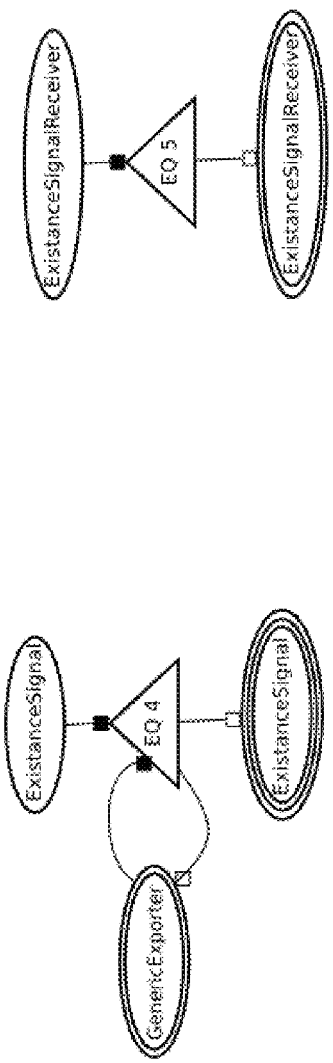
Fig. 24H
Fig. 24I
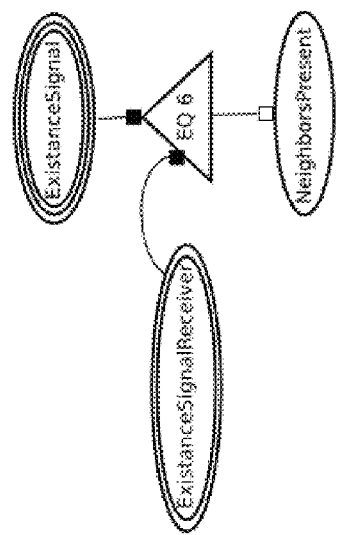
Fig. 24J

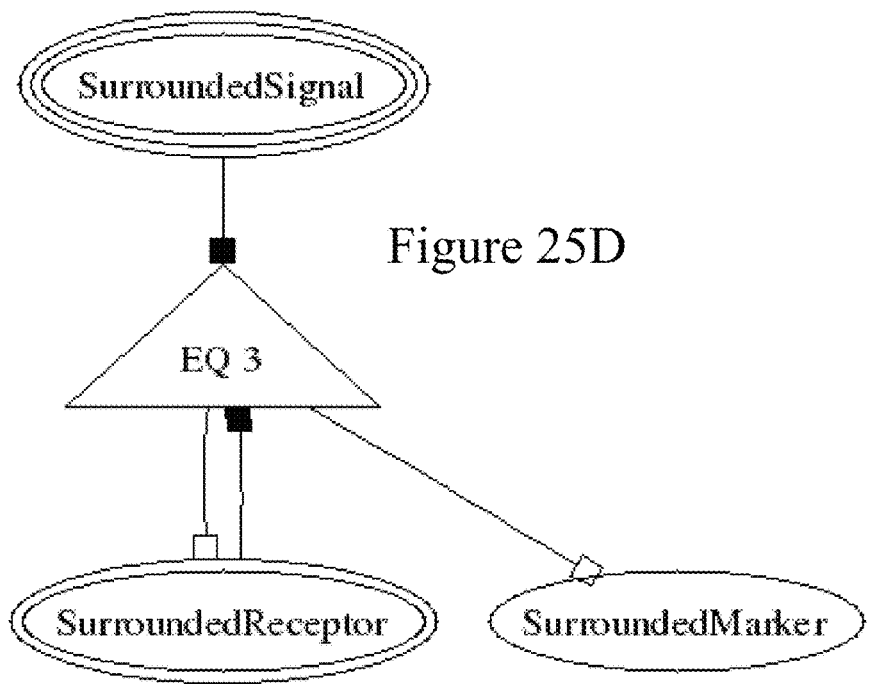
Figure 25D
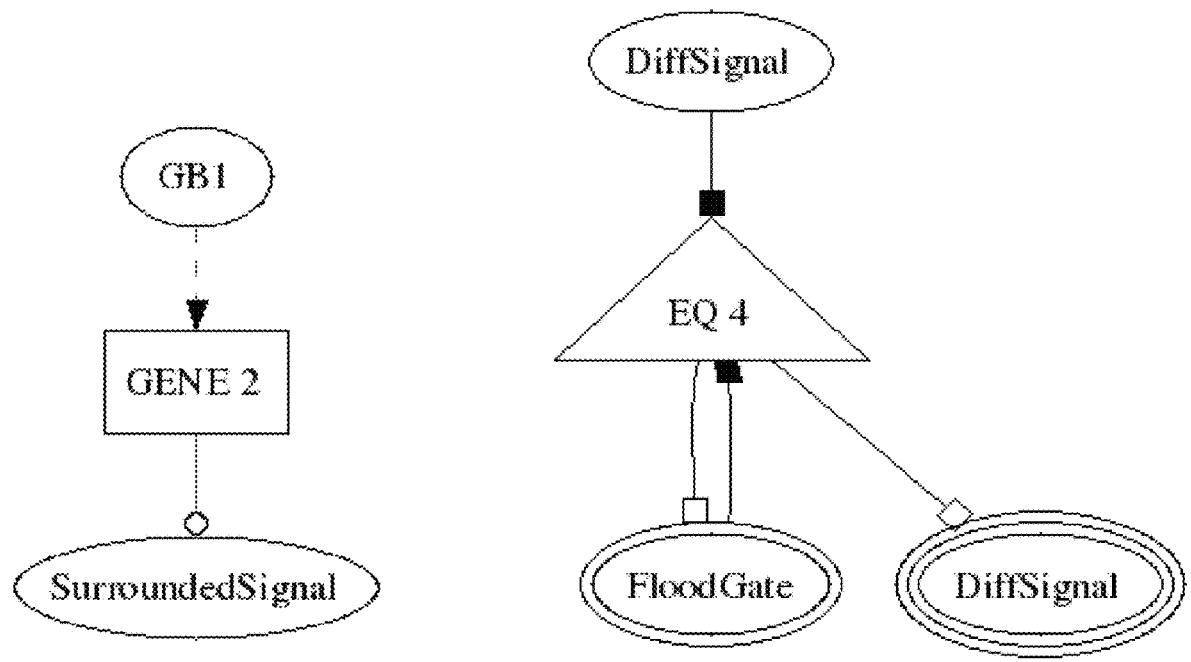
Figure 25E
Figure 25F

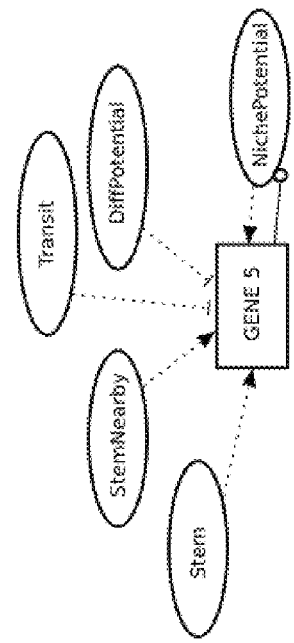
Fig. 27T
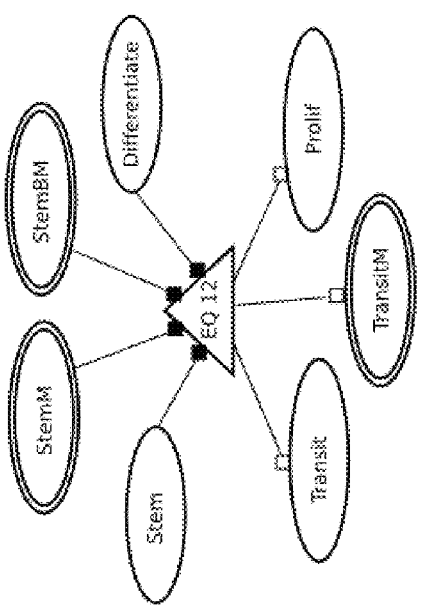
Fig. 27V
Fig. 27U
Fig. 27W

SYSTEMS AND METHODS FOR CELL-CENTRIC SIMULATION AND CELL-BASED MODELS PRODUCED THEREFROM

CROSS-REFERENCE TO APPLICATION(S) INCORPORATED BY REFERENCE

The present application is a continuation of PCT International Application No. PCT/US2008/075514, filed Sep. 5, 2008, which is a continuation in part of U.S. patent application Ser. No. 11/899,927, filed Sep. 7, 2007, now pending. The present application is also a continuation in part of U.S. patent application Ser. No. 11/899,927, filed Sep. 7, 2007, now pending. Both of the aforementioned applications, PCT International Application No. PCT/US2008/075514, filed Sep. 5, 2008, and U.S. patent application Ser. No. 11/899,927, filed Sep. 7, 2007, are incorporated by reference in their entireties as if fully set forth herein. The present application further incorporates by reference the subject matter of U.S. Patent Publication No. 2007/0233441 A1, entitled "METHOD, SYSTEM, AND APPARATUS FOR VIRTUAL MODELING OF BIOLOGICAL TISSUE WITH ADAPTIVE EMERGENT FUNCTIONALITY," filed Sep. 23, 2005, in its entirety as if fully set forth herein.

STATEMENT REGARDING FEDERALLY SPONSORED RESEARCH

The U.S. Government has a paid-up license in this invention and the right in limited circumstances to require the patent owner to license others on reasonable terms as provided for by the terms of Contract DAMD17-02-2-0049 as awarded by the US Army Medical Research Acquisition Activity (USAMRAA).

TECHNICAL FIELD

The present disclosure is generally directed to simulation systems and computer-implemented methods for modeling one or more biological events.

BACKGROUND

In vivo and in vitro biological research methods are useful for understanding the response of biological systems to various experimental conditions or challenges, such as cell growth conditions, stress, or exposure to drugs. The complexity of biological systems can obstruct interpretation of in vivo experimental results from studies of particular biological pathways or mechanisms. In vitro studies may help in resolving experimental results from these in vivo studies, but only by isolating the experimental system from physiological context.

In silico simulation of biological systems has the potential to keep subject processes and structures within a reasonably complete and detailed context, but still allow a researcher to target data of specific interest and origin. That is, in silico simulation allows dissection without separation. When used as a complementary and adjunct tool, in silico simulation can immediately make in vitro and in vivo research far more effective and, in some instances, reduce ethical issues.

However, current state of the art for in silico simulations suffer from limited applicability, rigid top-down designs, and static forms that provide only superficial mimicry of biological form and function, prevent open investigation of perturbations, mutations, and dynamic processes, and require complete knowledge of input pathways, states, or structures.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIGS. 13A-13C are schematic block diagrams illustrating modeled cell division and cell growth events using a solid sphere free-space model in accordance with an embodiment of the disclosure.

FIGS. 14A-14C are schematic block diagrams illustrating modeled cell growth and cell spatial resolution events for a plurality of virtual cells using a solid sphere free-space model in accordance with an embodiment of the disclosure.

FIGS. 25A-25K are schematic flow diagrams illustrating molecules and actions, virtual genes and gene products, and chemical-interaction rules for modeling a multicellular tissue in accordance with the simulation of biological events described in Example 2 of section G2, and in accordance with an embodiment of the disclosure.

DETAILED DESCRIPTION

A1. Overview

Figure 1A:
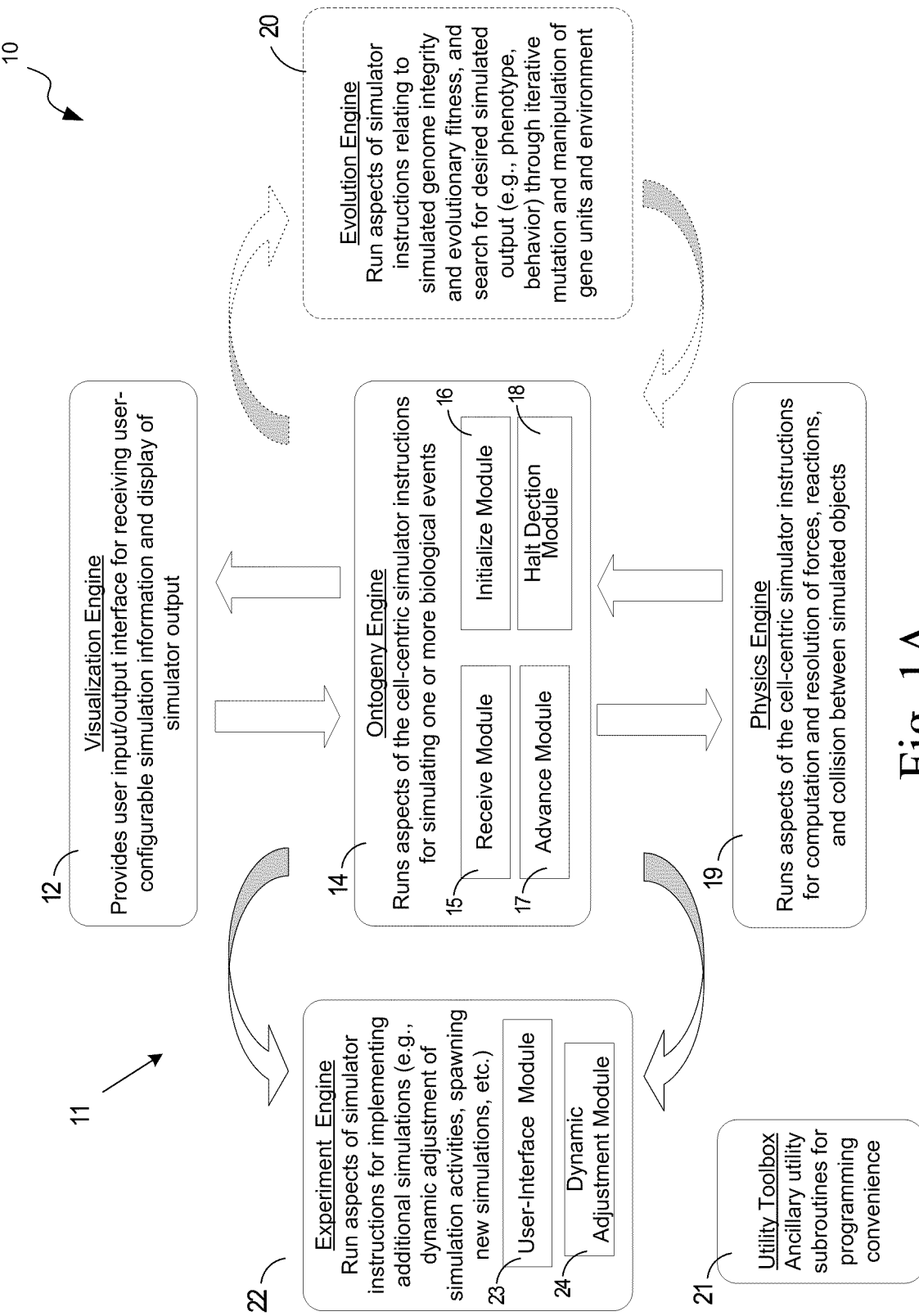
FIG. 1A is block diagram illustrating elements of a simulation system in accordance with an embodiment of the disclosure.

Systems and methods are provided herein that enable computer-implemented modeling of a biological event. In some embodiments, systems and methods are provided for cell-centric simulation. In other embodiments, cell-centric simulation can accommodate environment feedback. In one embodiment, cell-centric simulation can be implemented in accordance with configurable simulation information. In another embodiment, simulation of biological events, as described herein, can automatically implement additional simulation events in accordance with information captured during a previous simulation event and stored in a configuration file. Simulation of a biological event can include simulation of a plurality of biological events occurring concurrently and/or in sequential order. In some embodiments, simulation of biological events can include modeling biological processes (e.g., development of a multicellular tissue, differentiation of pluripotent cell, etc.), wherein the modeling generates one or more virtual cells having emergent properties.

In one embodiment, a simulation system for modeling a biological event includes a processor and a plurality of modules configured to execute on the processor. For example, the system can include a receive module configured to receive configurable simulation information and an initialize module configured to initialize an ontogeny engine to an initial step boundary in accordance with the configurable simulation information. The system can also include an advance module configured to advance the ontogeny engine from a current step boundary to a next step boundary in accordance with the configurable simulation information and the current step boundary, the advancing comprising performing a stepCells function. The system can further include a halt detection module configured to continue the execution of the advance module until a halting condition is encountered. In additional embodiments, the advancing step may also include performing one or more of a stepPhysics function, a killCells function and a stepECM function.

Another aspect of the disclosure is directed toward a computer-implemented method of modeling a biological event. The method can include receiving configurable simulation information and initializing an ontogeny engine to an initial step boundary in accordance with the configurable simulation information. The method can also include advancing the ontogeny engine from a current step boundary to a next step boundary in accordance with the configurable simulation information and the current step boundary. The advancing includes performing a stepCells function. The method can further include continuing the advancing until a halting condition is encountered.

In another embodiment, the disclosure is directed to a method for computer modeling. For example, the method can be used to model development of a virtual multicellular tissue having an emergent property of self-repair, adaptive response to an altered environment, or cellular differentiation. The method can include assigning to a virtual cell, a heritable virtual genome containing a set of gene units, wherein each gene unit has a gene control region that specifies the activity of the gene unit in response to molecules in the virtual environment, and a structural region that specifies the type of molecule or molecules produced by the gene unit, and wherein the molecules produced by the set of gene units include at least one of (a1) an intercellular adhesion molecule, (a2) a cell division molecule, (a3) a cell growth molecule, (a4) an intercellular signaling molecule, and (a5) a cell differentiation molecule. In some embodiments, the molecules produced by the set of gene units can include a combination of two or more molecule types selected from the molecule types (a1)-(a5).

The method can also include assigning at least one of (b1) a chemical-interaction rule to govern the extra-genetic behavior of molecules in the virtual environment, (b2) an action rule to promote an adhesion, growth, or cell-division condition of the cell, and (b3) a physical-interaction rule to govern cell movement in response to one or more changes in the virtual environment. The method can further include placing at least one virtual cell in the virtual environment. In some embodiments, the virtual cell can contain at least one molecule capable of activating a gene unit assigned to the virtual cell.

The method can further include updating the state of the virtual cell in the virtual environment, by updating the status of molecules produced by the gene units in the virtual cell, applying the chemical-interaction rule to update the status of the molecules present in the virtual cell and, optionally, in the virtual environment, applying the action rule to update the adhesion, growth, or division actions taken by the virtual cell, and applying the physical-interaction rule to update the position of the virtual cell with respect to the virtual environment. The method can also include repeating the updating step until a virtual multicellular tissue having one or more desired emergent properties develops. In one embodiment, the updating step continues until the developed virtual multicellular tissue reaches a state of maturity (e.g., analogous to a state of biological homeostasis). For example, a state of maturity can be a state in which (i) the status of the virtual cells is invariant over time, (ii) the condition of at least some of the virtual cells is oscillating around a stable cell condition, or (iii) virtual cells that are dying are being replaced by virtual daughter cells from dividing virtual cells.

The set of gene units in the virtual genome can contain gene units whose gene products, either by themselves or acting through a chemical-interaction rule, function to trigger an action rule relating to intercellular adhesion, trigger an action rule relating to cellular division, trigger an action rule relating to cell growth, produce molecules that are exported to the virtual environment, and/or trigger cell differentiation. In some embodiments, assigned action rules can include rules relating to the plasticity, elasticity, and rigidity of a cell adhesion force.

In some instances, the physical interaction rules can include rules for calculating intercellular forces, based on the degree of overlap between or among the virtual cells, and for resolving cell overlap during a stepPhysics operation. In other embodiments the physical interaction rules can include rules for calculating a separation distance between two or more virtual cells, and for resolving adhesion connections between the two or more separated virtual cells during a stepPhysics operation.

In some embodiments, a virtual cell can be assigned a spherical shape that is preserved through cell growth and cell division. In such embodiments, intercellular forces can be applied between a center point of a first virtual cell and a center point of a second virtual cell.

In other embodiments, a virtual cell can be assigned a plurality of spherical subcells connected together to simulate a free-form cell that can accommodate a plurality of shapes. In one embodiment, the plurality of spherical subcells can be assigned intracellular adhesion forces such that subcells have an affinity for adjacent subcells of the same virtual cell. Intercellular adhesion forces can also be calculated between subcells of a first virtual cell and subcells of a second virtual cell. For example, the physical interaction rules can include rules for calculating intracellular and intercellular forces between or among subcells belonging to the same and/or adjacent virtual cells, respectively. Additionally, the physical interaction rules can include rules for resolving subcell overlap and/or subcell separation during a stepPhysics operation In one embodiment, the method for computer modeling can further include employing a visualization engine for displaying a graphical, a numerical, and/or an alphanumeric representation of progress and/or results from a simulation session (e.g., modeling development of a tissue). In further embodiments, the method for computer modeling can include adjusting one or more parameters of the configurable simulation information. Adjustment of the one or more parameters can include adjusting one or more parameters selected from the group consisting of: (i) a virtual environment molecule profile (e.g., the types or distribution of molecules); (ii) a chemical-interaction rule; (iii) an action rule; (iv) a physical-interaction rule, and (v) the set of gene units.

In one embodiment, the updating step can continue until the virtual multicellular tissue reaches a state of homeostasis. In this embodiment, the method for computer modeling can further include at least one of: (1) perturbing the shape of the virtual tissue, and applying the updating and repeating steps until the virtual tissue returns to a state of homeostasis; (2) changing a virtual environment molecule profile, and applying the updating and repeating steps until the virtual tissue returns to a state of homeostasis; and (3) killing or removing cells from the virtual tissue, and applying the updating and repeating steps until the tissue returns to a state of homeostasis.

Other aspects of the disclosure are directed toward a multi-cellular virtual tissue having an emergent property (e.g., self-repair, adaptive response to an altered environment, tissue differentiation, etc.). In one embodiment, the multi-cellular virtual tissue can contain at least one pluripotent cell capable of division and differentiation toward non-pluripotent cell types, and at least one or more non-pluripotent cell types. Further, the virtual tissue can include a plurality of virtual cell layers, wherein virtual cells in each of the plurality of virtual layers are differentially specialized with respect to each of the other virtual cell layers.

The following description provides specific details for a thorough understanding and enabling description of these embodiments of the disclosure. One skilled in the art will understand, however, that the disclosure can be practiced without many of these details. Additionally, some well-known structures or functions may not be shown or described in detail, so as to avoid unnecessarily obscuring the relevant description of the various embodiments.

A2. Terminology

The terms below have the following definitions herein, unless indicated otherwise:

In biology, a "cell" is the basic unit of living matter in all organisms. A cell is a self-maintaining system employing chemical and physical mechanisms for obtaining energy and/or materials to satisfy nutritional and energy requirements. A cell represents the simplest level of biological organization that manifests all the features of the phenomenon of life with the capacity for autonomous reproduction, for example by cellular division. A "virtual cell", as used herein, is a computer-simulated analogue of a biological cell (e.g., a modeled cell, a simulated cell, etc.). For example, the virtual cell is separated from its environment (e.g., modeled extracellular matrix, modeled substrate, other virtual cells, etc.) via a cell barrier, e.g., virtual cell "membrane" such that the cell can be considered a discrete unit having an intracellular space separate from the extracellular surroundings.

A virtual cell can also be provided with a virtual genome having a plurality of virtual genes or gene units that can confer on the cell a number of modeled cellular functions. For example, virtual genes can provide a means from which basic cellular functions can be simulated, wherein basic cellular functions can include, but not limited to, (1) gene expression, (2) cell metabolism, (3) cell division, and/or (4) cell growth. In some embodiments, the virtual cells ("cells") can be provided with one or more gene units (e.g., virtual genes, virtual gene product, molecules, etc.) that can be influenced during simulation to invoke a cell "death" or elimination during simulation. In further embodiments, the cells can be provided with one or more gene units that can be influenced during simulation to invoke biological events, such as differentiation from one cell state or cell type to a second cell state or cell type (e.g., different states of cell differentiation).

The virtual genome can provide a template for enabling simulation of one or more biological events including simulation of cell growth, cell division, cell homeostasis, cell death, cell differentiation, tissue formation, etc. In one embodiment, the virtual genome can be the collection of gene units assigned to or applied to a virtual cell. In another embodiment, the virtual genome can be a sub-collection of gene units assigned to or applied to a virtual cell. For example, in some embodiments, a cell can be provided with more than one virtual genome, wherein each virtual genome includes a set of gene units that can be applied to a particular class of functions (e.g., metabolism genome, cell primitive genome [discussed below], fibroblast development genome, stem cell genome, neuron genome, etc.).

"Virtual genes" (e.g., gene units, gene assemblies) are computer simulation analogues, possibly abstracted, of biological genes. Each gene unit can have a gene control "region" that regulates an activity status or activity level (e.g., low, high, attenuated, etc.) of the gene unit (e.g., in response to absence or presence of molecules in the environment and/or cell). For example, in one embodiment, molecules can positively and/or negatively regulate gene control regions based on their presence, absence, location within the environment, movement within the environment, etc. In further embodiments, a quantity of a molecule within the macro- and/or micro-environment can attenuate the simulated response (e.g., high activity, low activity, etc.). In additional embodiments, more than one molecule can interact with a gene control region, thereby further attenuating a gene unit activity response to the environment during simulation. In addition to control regions, gene units can have a structural "region" (e.g., information configured to specify the type of molecule or molecules produced by the gene unit). For example, a growth gene unit may be denoted as [DiffuseNutrient 0.18, NeighborPresent −3] [Growth], specifying that a growth molecule is promoted moderately (0.18) by DiffuseNutrient, and strongly inhibited (−3.00) by NeighborPresent. In some embodiments, the structural region can specify more than one type of molecule generated by the gene unit.

A virtual "environment" can include a computer simulation analogue, possibly abstracted, of a biological cellular environment. The term "environment", as used herein, can reference both extracellular and intracellular environments, and thereby encompasses the entirety of the space or volume occupied by one or more virtual cells in the simulation system as well as the virtual space in which the cells are placed. In one embodiment, the environment can be uniform (e.g., molecules present are uniformly distributed and can invoke simulated biological events in one or more cells present in the environment regardless of location (e.g., coordinates). In another embodiment, the environment can be non-uniform or consist of a plurality of micro-environments. For example, a first micro-environment can include a first set of molecules, and a second micro-environment can include a second set of molecules. Virtual cells residing in the respective first and second micro-environments can be differentially affected (and thereby show differential modeled behavior).

Intracellular environments can also be uniformly- and/or variably-configured in accordance with an embodiment of the disclosure. For example, a virtual cell can be discreetly or non-discreetly subdivided with respect to distribution of molecules. As such, increasingly complex levels of detail that mimic the intricacies of natural biological systems can be applied using the simulation system as described herein.

"Molecules", as used herein, are computer simulation analogues, possibly abstracted, of molecules found in biological systems. For example, a molecule refers to a virtual compound or resource that can be produced by a virtual gene, or alternatively, is introduced into the environment or converted by a chemical-interaction rule. A function or set of functions can be applied to a molecule, such that, when present, the molecule can affect the state of one or more virtual cells, e.g., through its interaction with other molecules and/or gene units in a virtual cell, etc. A molecule, whether referred to in a singular or plural form, refers to a collection of a model type. A molecule can be provided a strength value indicating the molecule's relative amount or presence in a virtual environment or cell. The strength value (e.g., relative concentration) can be altered during simulation.

"Chemistry equations" or "chemical-interaction rules" refer to a set of equations that, when invoked, can simulate the extra-genetic (e.g., non-gene) behavior and interactions between or among intracellular and/or extracellular molecules, such as products generated by gene unit activity, simulated cell receptors, simulated cell transporters, etc.

"Action rules" can be provided and invoked in silico to simulate cellular adhesion events, growth events, division events and/or stages of the cell cycle, etc. For example, action rules can be a set of operational directives that are invoked when one or more pre-configured conditions are met. For example, action rules can be used, at least in part, to simulate a cell's influence from and/or on adjacent cells. Action rules can also be used, at least in part, to simulate a cell's growth to a larger cell size or to divide a cell into two cells. In some embodiments, action rules can be invoked in response to one or more molecules present in the environment, such as those molecules produced by a gene unit relating to intercellular adhesion, cell growth, cell division, etc.

"Physical-interaction rules" can be provided and invoked in silico to simulate how a cell will move in response to its own simulated growth, simulated division, simulated growth and/or division of neighboring cells, and/or how a cell will move in response to physical constraints or perturbations imposed by the environment.

A "molecule profile" can be used to define the types of molecules, distribution of each molecule, concentration of each molecule, etc., for a particular environment (e.g., macro-environment, micro-environment, etc.) or virtual cell (e.g., intracellular environment). Change in a molecule's concentration and/or gradient within an environment or virtual cell can be defined as molecule flux. During simulation, a molecule profile can change via simulation-induced molecule flux.

A gene unit can serve as a template for generating molecules that provide cellular function or activity (within the simulation scheme), such as intercellular adhesion, cell division, cell growth, intercellular signaling, etc. As such, molecule flux within the simulation scheme can alter the state or states of a virtual cell and/or adjacent cells. As representative of molecular mechanisms recognized in biological systems, a molecule and/or other resource can effect a specified role or function within the context of the biological system, such as, by directly or indirectly invoking action and/or physical-interaction rules, interacting with other molecules through chemical-interaction rules, etc. One of ordinary skill in the art will recognize that the molecule(s) derived from a gene unit can provide more than one function within the simulation scheme.

"Cell primitives" refer to the simplest operations or behaviors that a virtual cell can perform (e.g., ability to divide, ability to grow larger, ability to move, etc.). All other operations of a cell can be combinations of such cell primitives and/or combinations of cell primitives and other operations or behaviors that a virtual cell can perform.

A "virtual tissue" is a collection of virtual cells collectively having a shape and functional characteristics within the simulation scheme. In biology, a tissue is a mass of cells that are derived from the same origin, but are not necessarily identical, and which work together to perform a particular function or set of functions. For example, tissues (e.g., epithelial, muscle, neural, connective, vascular, etc.) can be recognized as an intermediate form of cellular organization between the individual cell and an organism (e.g., animal, plant).

"Cell signaling" can refer to an event in which molecules assigned a signaling function and which are available in the virtual environment (e.g., generated during a simulation step and/or session from a gene unit) can affect the behavior of one or more cells in that environment. For example, simulative generation of a "signaling" molecule in one virtual cell can, in a next step, interact with "receptor" molecules in or on a second virtual cell. When simulating cell signaling processes, chemical-interaction rules can further effect a behavior change in the second virtual cell (e.g., activation of one or more gene units within the second cell, etc.).

A "signal" molecule can refer to a nutrient or other molecule located external to a virtual cell that can, directly or indirectly, affect the behavior of the cell within the context of the simulation scheme. For example, the presence of a signal molecule can spawn simulative responses such as transport of the signal molecule into a virtual cell, interaction with a control region of a gene unit, interaction with a cell surface receptor molecule, etc.

When present, a "receptor" molecule can be localized on a virtual cell's surface (e.g., cell barrier, cell membrane, etc.). Interaction, via an invoked chemical-interaction rule, between an extracellular molecule with a signal function and a receptor molecule localized on a virtual cell surface, can directly or indirectly affect the behavior of the cell by invoking one or more additional chemical-interaction rules, action rules, or other rules.

An "adjacent cell," as applied to a specified virtual cell, refers to other cells that are in contact with and/or are an immediate neighbor of that cell with respect to the simulated environment. In one embodiment, the simplest neighborhood of a cell consists of those cells that are spatially adjacent to (touching) the cell of interest. However, in other embodiments, a cell's neighborhood may be configured as any arbitrary group of cells. For example, a neighborhood (the cells to/from which it will send/receive signals) could include cells that are not adjacent, as occurs in vivo with cells that are able to signal non-local cells via hormones.

The "phenotype" of an organism or tissue refers to the observable traits, appearance, properties, function, and behavior of the subject organism or tissue.

"Physical constraints" refer to constraints imposed upon the position and/or growth of a cell due to the presence of adjacent cells or size limits of the tissue.

A "totipotent cell" refers to a cell having the capability to form, by one or more rounds of simulated cell division, other totipotent cells, pluripotent cells, or differentiated cell types. In biology, totipotent cells can give rise to any of the various cell types in an organism.

A "pluripotent cell" refers to a cell that can give rise to daughter cells capable of differentiating into a limited number of different cell types. For instance, dermal stem cells (e.g., a pluripotent cell) can give rise to cells of a variety of dermal cell types, but do not give rise to cells of non-dermal cell types.

A "stem cell" can refer to a totipotent or pluripotent cell. For example, a stem cell can be an undifferentiated or partially undifferentiated cell that can divide indefinitely, the process of which can give rise to a first daughter cell that can undergo a terminal differentiation event resulting in a cell having a specific cell type and/or function. The second daughter cell resulting from each successive division event can be a stem cell that retains its proliferative capacity and an undifferentiated state or partially undifferentiated state.

A "virtual stem cell", "virtual totipotent cell", or "virtual pluripotent cell" refer to virtual cells having analogous characteristics to their biological cell counterparts described above.

"Homeostasis" refers to the ability or tendency of an organism or cell to maintain a relatively constant shape, temperature, fluid content, etc., by the regulation of its physiological processes in response to its environment.

"Emergent properties" or "emergent behavior" refers to a process or capability that exists at one level of organization, but not at any lower level and that depends on a specific arrangement, organization, or interaction of the lower level components. Two emergent behaviors of a virtual tissue in accordance with embodiments of the disclosure are (i) self-repair, induced response whereby cells are replaced when they have been killed, damaged, or removed, and (ii) adaptation, meaning a change in structure, function, or habits as appropriate for different conditions, enabling an organism to survive and reproduce in a certain environment or situation.

An "interval" refers to a time period, typically but not necessarily a discrete time period, at which the state or status of the cells making up a virtual tissue are updated, e.g., while simulating or modeling a biological event.

"Cell differentiation" is the process by which cells acquire a more specialized form or function during development. Cell differentiation can be, in part, described in terms of incremental and/or various stages transitioning the cell toward a terminal stage (e.g., of specialized form or function). For example, stages of differentiation can include a committed and/or specified stage that indicates the cell's strong propensity to differentiate, a determined stage that indicates an inexorable commitment to differentiation, etc. In one example, during early embryonic animal development, a plurality of identical cells eventually become committed to alternative differentiation pathways resulting in development of specialized tissues (e.g., bone, heart, muscle, skin, etc.) in the developing animal. See also pluripotent and totipotent discussed above.

B. Embodiments of Computing Environments

B1. Suitable Computing Systems

Figure 28:
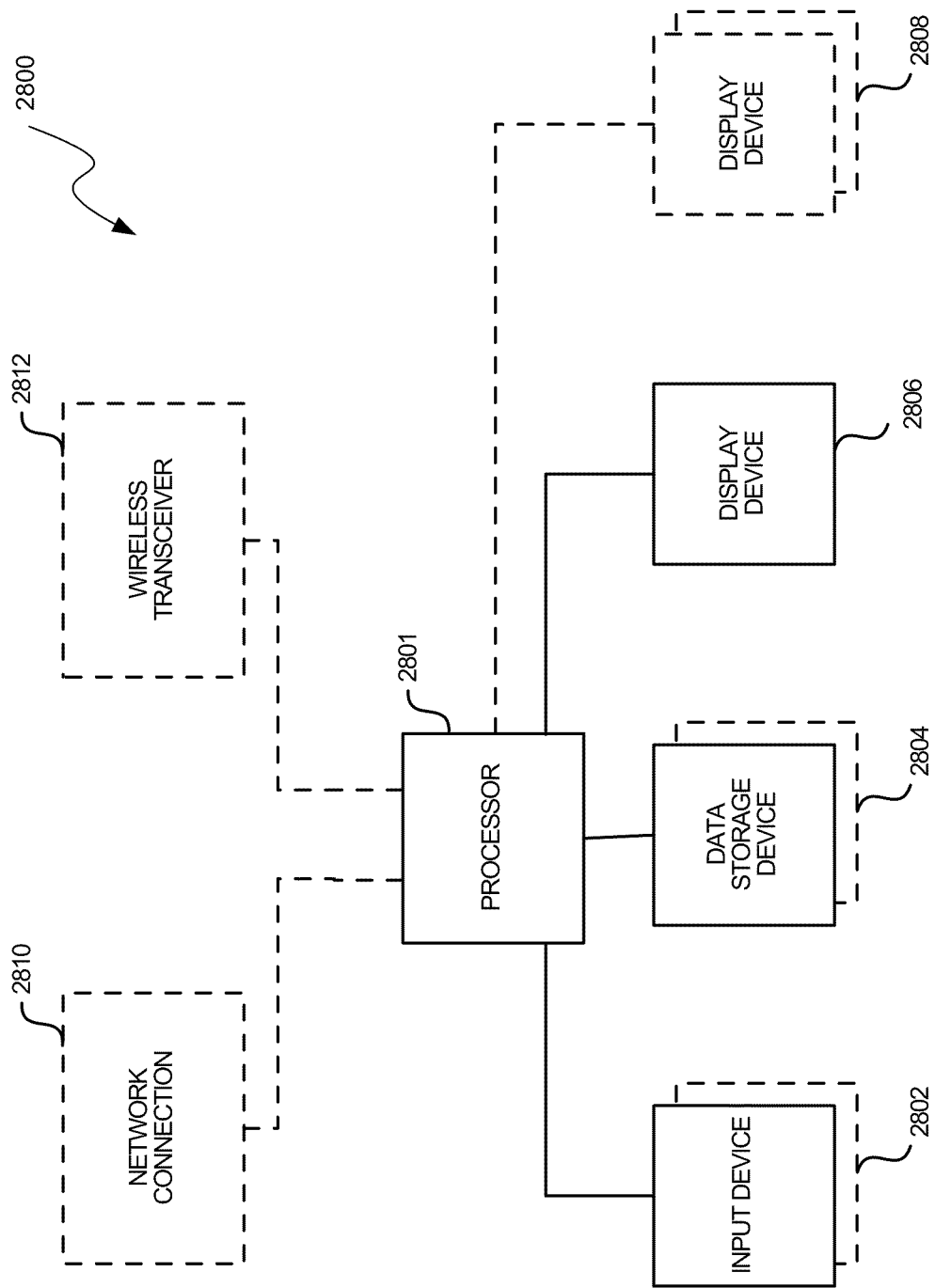
FIG. 28 is a block diagram of a basic and suitable computer that may employ aspects of the disclosure.

FIG. 28 and the following discussion provide a general description of a suitable computing environment in which aspects of the disclosure can be implemented. Although not required, aspects and embodiments of the disclosure will be described in the general context of computer-executable instructions, such as routines executed by a general-purpose computer, e.g., a server or personal computer. Those skilled in the relevant art will appreciate that the disclosure can be practiced with other computer system configurations, including Internet appliances, hand-held devices, wearable computers, cellular or mobile phones, multi-processor systems, microprocessor-based or programmable consumer electronics, set-top boxes, network PCs, mini-computers, mainframe computers and the like. The disclosure can be embodied in a special purpose computer or data processor that is specifically programmed, configured or constructed to perform one or more of the computer-executable instructions explained in detail below. Indeed, the term "computer", as used generally herein, refers to any of the above devices, as well as any data processor.

The disclosure can also be practiced in distributed computing environments, where tasks or modules are performed by remote processing devices, which are linked through a communications network, such as a Local Area Network ("LAN"), Wide Area Network ("WAN") or the Internet. In a distributed computing environment, program modules or sub-routines may be located in both local and remote memory storage devices. Aspects of the disclosure described below may be stored or distributed on computer-readable media, including magnetic and optically readable and removable computer discs, stored as firmware in chips (e.g., EEPROM chips), as well as distributed electronically over the Internet or over other networks (including wireless networks). Those skilled in the relevant art will recognize that portions of the disclosure may reside on a server computer, while corresponding portions reside on a client computer. Data structures and transmission of data particular to aspects of the disclosure are also encompassed within the scope of the disclosure.

Referring to FIG. 28, one embodiment of the disclosure employs a computer 2800, such as a personal computer or workstation, having one or more processors 2801 coupled to one or more user input devices 2802 and data storage devices 2804. The computer is also coupled to at least one output device such as a display device 2806 and one or more optional additional output devices 2808 (e.g., printer, plotter, speakers, tactile or olfactory output devices, etc.). The computer may be coupled to external computers, such as via an optional network connection 2810, a wireless transceiver 2812, or both.

The input devices 2802 may include a keyboard and/or a pointing device such as a mouse or haptic device. Other input devices are possible such as a microphone, joystick, pen, touch screen, scanner, digital camera, video camera, and the like. The data storage devices 2804 may include any type of computer-readable media that can store data accessible by the computer 2800, such as magnetic hard and floppy disk drives, optical disk drives, magnetic cassettes, tape drives, flash memory cards, digital video disks (DVDs), Bernoulli cartridges, RAMs, ROMs, smart cards, etc. Indeed, any medium for storing or transmitting computer-readable instructions and data may be employed, including a connection port to or node on a network such as a local area network (LAN), wide area network (WAN) or the Internet (not shown in FIG. 28).

Aspects of the disclosure may be practiced in a variety of other computing environments. For example, referring to FIG. 29, a distributed computing environment with a network interface includes one or more computing devices 2902 (e.g., a client computer) in a system 2900 are shown, each of which includes a remote client module 2904 that permits the computing device to access and exchange data with the network 2906 (e.g., Internet, intranet, etc.), including web sites within the World Wide Web portion of the Internet. The computing devices 2902 may be substantially similar to the computer described above with respect to FIG. 28. Computing devices 2902 may include other program modules such as an operating system, one or more application programs (e.g., word processing or spread sheet applications), and the like. The computing devices 2902 may be general-purpose devices that can be programmed to run various types of applications, or they may be single-purpose devices optimized or limited to a particular function or class of functions. While shown with remote client applications using internet protocols or proprietary communication protocols for communication via network 2906, any application program for providing a graphical user interface to users may be employed (e.g., network browsers), as described in detail below.

At least one server computer 2908, coupled to the network 2906 (e.g., Internet or intranet) 2906, performs much or all of the functions for receiving, routing and storing of electronic messages, such as web pages, data streams, audio signals, and electronic images. While the Internet is discussed, a private network, such as an intranet may indeed be preferred in some applications. The network may have a client-server architecture, in which a computer is dedicated to serving other client computers, or it may have other architectures such as a peer-to-peer, in which one or more computers serve simultaneously as servers and clients. In some embodiments, a database 2910 or databases, coupled to the server computer(s), can store much of the content exchanged between the computing devices 2902 and the server 2908. The server computer(s), including the database(s), may employ security measures to inhibit malicious attacks on the system, and to preserve integrity of the messages and data stored therein (e.g., firewall systems, secure socket layers (SSL), password protection schemes, encryption, and the like).

The server computer 2908 can also contain an internal memory component 2920. The memory 2920 can be standard memory, secure memory, or a combination of both memory types. The memory 2920 and/or other data storage device 2910 can contain computer readable medium having computing device instructions 2922, such as cell-centric simulator computing device instructions. The encoded computing device instructions 2922 are electronically accessible to at least one of the computing devices 2908 and 2902 for execution. In further embodiments, computing device instructions 2922 can include basic operating instructions, cell-centric simulator instructions (e.g., source code, configurable simulation information), etc.

The server computer 2908 may include a server engine 2912, a web page management component 2914, a content management component 2916, a database management component 2918 and a user management component 2924. The server engine performs basic processing and operating system level tasks. The web page management component 2914 handles creation and display or routing of web pages. Users may access the server computer by means of a URL associated therewith. The content management component 2916 handles most of the functions in the embodiments described herein. The database management component 2918 includes storage and retrieval tasks with respect to the database 2910, queries to the database, read and write functions to the database and storage of data such as video, graphics and audio signals. The user management component 2924 can support authentication of a computing device to the server 2908.

Many of the functional units described herein have been labeled as modules, in order to more particularly emphasize their implementation independence. For example, modules may be implemented in software for execution by various types of processors, such as processor 2801. An identified module of executable code may, for instance, comprise one or more physical or logical blocks of computer instructions which may, for instance, be organized as an object, procedure, function, or algorithm. The identified blocks of computer instructions need not be physically located together, but may comprise disparate instructions stored in different locations which, when joined logically together, comprise the module and achieve the stated purpose for the module.

A module may also be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

A module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

B2. Embodiments of User Systems and Interfaces

Figure 29:
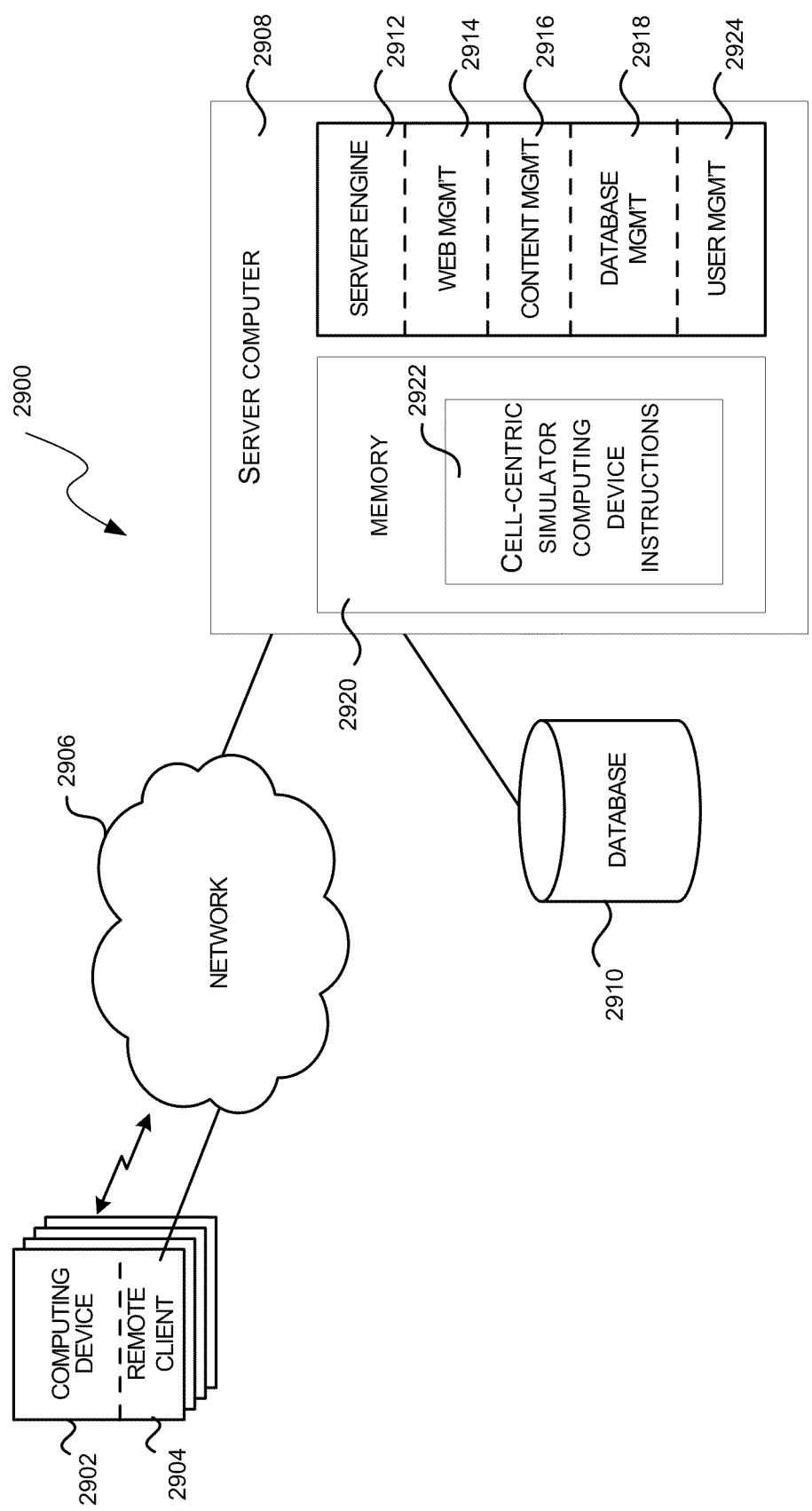
FIG. 29 is a block diagram illustrating a simple, yet suitable system in which aspects of the disclosure may operate in a networked computer environment.
Figure 30:
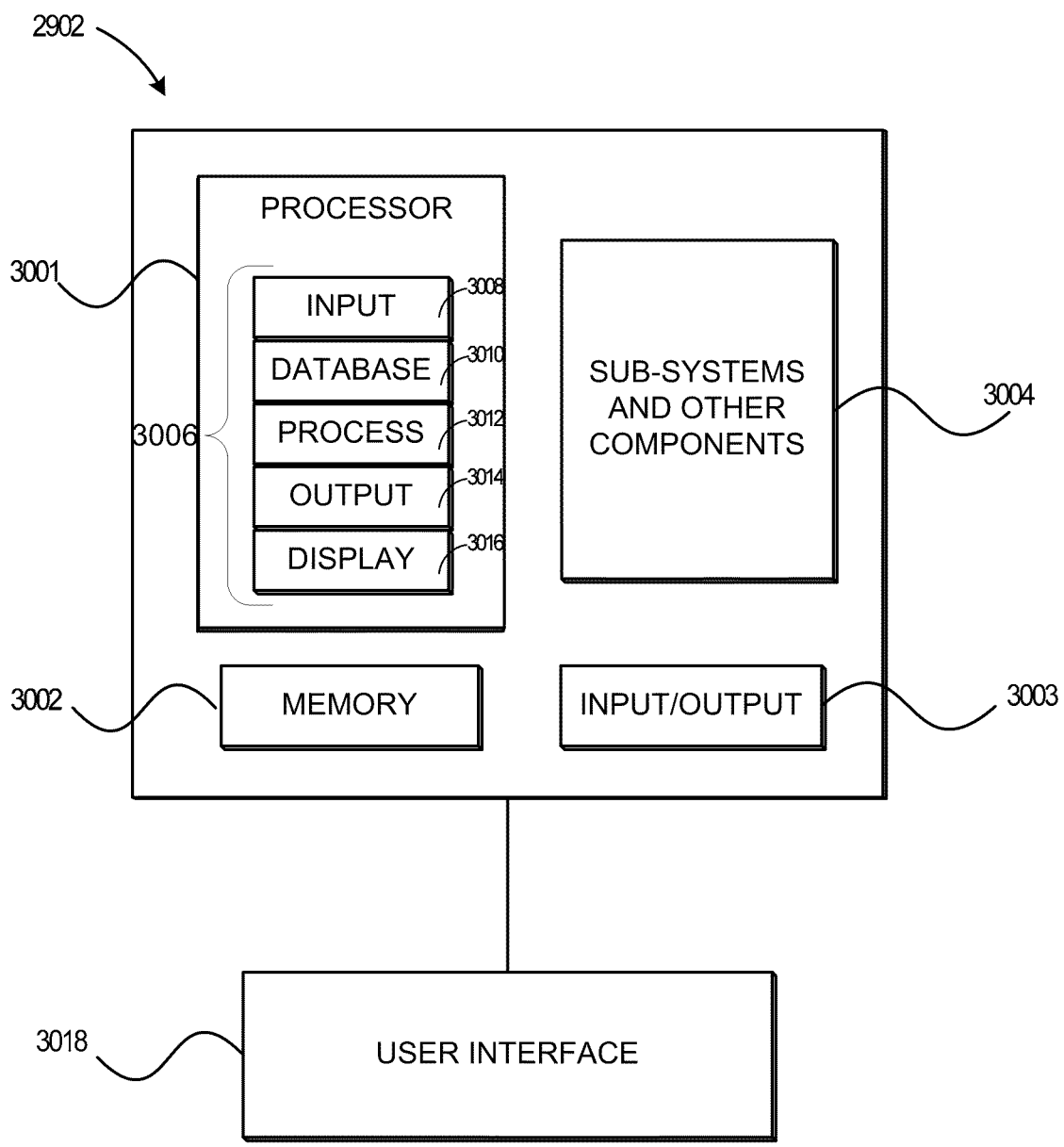
FIG. 30 is a schematic block diagram illustrating subcomponents of the computing device of FIG. 29 in accordance with an embodiment of the disclosure.

FIG. 30 is a schematic block diagram illustrating subcomponents of the computing device 2902 of FIG. 29 in accordance with an embodiment of the disclosure. The computing device 2902 can include a processor 3001, a memory 3002 (e.g., SRAM, DRAM, flash, or other memory devices), input/output devices 3003, and/or subsystems and other components 3004. The computing device 2902 can perform any of a wide variety of computing processing, storage, sensing, imaging, and/or other functions. Components of the computing device may be housed in a single unit or distributed over multiple, interconnected units (e.g., through a communications network). The components of the computing device 2902 can accordingly include local and/or remote memory storage devices and any of a wide variety of computer-readable media.

As illustrated in FIG. 30, the processor 3001 can include a plurality of functional modules 3006, such as software modules, for execution by the processor 3001. The various implementations of source code (e.g., in a conventional programming language) can be stored on a computer-readable storage medium or can be embodied on a transmission medium in a carrier wave. The modules 3006 of the processor can include an input module 3008, a database module 3010, a process module 3012, an output module 3014, and, optionally, a display module 3016.

In operation, the input module 3008 accepts an operator input via the one or more input devices described above with respect to FIG. 28, and communicates the accepted information or selections to other components for further processing. The database module 3010 organizes records, including simulation records, configurable simulation information, generated models, and other operator activities, and facilitates storing and retrieving of these records to and from a data storage device (e.g., internal memory 3002, external database 2910, etc.). Any type of database organization can be utilized, including a flat file system, hierarchical database, relational database, distributed database, etc.

In the computing environment illustrated in FIG. 30, the process module 3012 can generate simulation control variables based on operator input accepted by the input module 3008, simulation operational parameters, etc., and the output module 3014 can communicate operator input to external computing devices such as server computer 3008. In other embodiments, the input module 3008 can accept data transmitted by a server, such as server 2908 (e.g., over a network 2906). The display module 3016 can be configured to convert and transmit simulation parameters, biological event modeling, input data, etc. through one or more connected display devices, such as a display screen, printer, speaker system, etc.

In various embodiments, the processor 3001 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 3002 can be standard memory, secure memory, or a combination of both memory types. By employing a secure processor and/or secure memory, the system can ensure that data and instructions are both highly secure and sensitive operations such as decryption are shielded from observation.

The computing environment 2900 can receive user input in a plurality of formats. In one embodiment, data is received from a user-operated computer interface 3018 (i.e., "user interface"). In various embodiments, the user interface 3018 is associated with the computing device 2902 and can include various input and output devices, such as a keyboard, a mouse, a haptic device, buttons, knobs, styluses, trackballs, microphones, touch screens, liquid crystal displays, light emitting diode displays, lights, speakers, earphones, headsets, and the like. In other embodiments not shown, the user interface 3018 can be directly associated with the server computer 2908.

Referring back to FIG. 29, the computing device 2902 may connect to network resources, such as other computers 2902 and 2908 and one or more data storage devices 2910. As examples, the computing device 2902 may connect to a server 2908 to upload data logs, configurable simulation information, simulation commands, and so forth. The computing device 2902 may also connect to a server 2908 to download updates to software, cell-centric simulator computing device instructions, and so forth. The computing device 2902 can also connect to the data storage device 2910. As described above, the computing device 2902 may connect to network resources via network 2906, such as the Internet or an intranet.

B3. Embodiments of Systems and Methods for Simulating a Biological Event

The method, system, and apparatus disclosed herein are directed to a computational approach and platform that incorporates principles of biology, particularly those primitive features of living systems that are fundamental to their construction and operation and that distinguish them from non-living systems. The goal of such incorporation is to identify, extract, and capture in algorithmic form the essential logic by which a living system self-organizes and self-constructs. Such algorithmic form(s) include a perspective based on the properties of the natural cells and embeds those properties within the simulation system for modeling one or more biological events. Accordingly, the cell-based (e.g., cell-centric) approach to modeling biological events and processes produces advantageous modeling features, such as accommodating dynamic environment feedback and hierarchical organization of cells and tissues, thereby effectuating emergent properties.

The simulation system and methods disclosed herein can be used to simulate a developmental process starting from a single cell or initial grouping of cells, each with a configured genome (e.g., genotype), to model resultant tissue and/or cellular phenotypes. Phenotypic properties, such as tissue shape and self-repair, arise from the interaction of gene-like elements as the multicellular virtual tissue develops. The simulation system can include an ontogeny engine (described in further detail below) for defining and controlling the parameters of the virtual environment necessary for modeling biological events, such as, tissue development, placement of nutrients, allocation of space for cells to grow, sequencing of simulated events and/or actions, rules that invoke simulation of natural physical laws in the virtual environment, etc. To make the simulation and modeling flexible, the environmental parameters, including rules governing the calculation of molecular affinity as well as the placement and concentration of nutrients or other molecules, are configurable.

The present simulation platform provides means for receiving and updating configurable simulation information relating to the simplest operations or behaviors that a virtual cell can perform (e.g., the cellular primitives). For example, configurable simulation information can capture, in algorithmic form, the primitive features of living systems by which the system can self-organize, self-construct, and self repair. The logic behind primitive features (i.e., cell primitives) that can be captured in algorithmic form can include a cell's genome, cellular membrane, extracellular matrix (ECM), ability to divide, ability to grow larger, ability to move or migrate through an environment, ability to maintain and/or change cell shape, ability to polarize, ability to differentiate (functionally specialize), ability to communicate with neighboring cells and the surrounding environment (e.g., send and receive signals), ability to age and/or die, ability to retain or recall or readapt to recent cellular states, ability to connect to adjacent cells and/or the ECM via cellular adhesion, etc. As such, configurable information relating to cell primitives provides the simulation platform with the means to model biological processes such as differentiation (specialization) of cell clusters, communication and feedback between specialized clusters, and metabolism.

FIG. 1A is block diagram illustrating elements of a simulation system 10 in accordance with an embodiment of the disclosure. As shown in FIG. 1A, the system 10 includes a cell-centric simulator 11 configured to model one or more biological events. In one example, the cell-centric simulator 11 can simulate a developmental process (e.g., tissue growth and generation, cell differentiation, blastocyte development starting from a single fertilized egg, etc.). In one embodiment, the cell-centric simulator 11 can model tissue phenotype (e.g., appearance, physical traits, properties, etc.). Properties such as tissue shape and self-repair arise from the interaction of modeled gene-like elements (e.g., gene units) as the multicellular virtual tissue develops. In some embodiments, the simulator 11 can define and control a plurality parameters of the virtual environment necessary for modeling cellular and/or tissue development, including placement of nutrients, defining space for cells to grow, sequencing of simulated events and/or actions, rules that invoke simulation of natural physical laws in the virtual environment, etc. In additional embodiments, environmental parameters (e.g., rules governing the calculation of molecular affinity and the placement and concentration of nutrients or other molecules, etc.) are configurable at run-time.

In one embodiment, the cell-centric simulator 11 can include a visualization engine 12 for supporting client visualization and manipulation of simulation data generated during a simulation session. In one embodiment, the visualization engine can be supported on a client computing device, such as computing device 2902 (FIGS. 29 and 30)

as, for example, a client application. In another embodiment, the visualization engine 12 can be supported by another computing device, such as the server 2908 and/or another computing device. The visualization engine 12 can include a user input and output interface and be configured to interact with the simulator 11 and system 10 (e.g., imputing/receiving user-configurable simulation information, requesting simulation of a biological event, interacting with a simulation in real-time, displaying results and/or data of a completed simulation, etc.). In some embodiments, the visualization engine 12 can be configured to display at least one of a graphical, a numerical and an alphanumeric representation of data generated during or following a simulation session. For example, the visualization engine 12 can be configured to generate and display a graphical image representing the current status of the simulation at a user interface, such as user interface 3018 (FIG. 30).

The cell-centric simulator 11 can also include the ontogeny engine 14 for running aspects of the cell-centric simulator instructions (e.g., relating to simulation of biological events, developmental processes, metabolic processes, etc.). For example, the ontogeny engine 14 can include a receive module 15, an initialize module 16, an advance module 17 and a halt detection module 18. In another embodiment, not shown, the ontogeny engine can also include an output module. In general, modules 15, 16, 17 and 18 comprise listings of executable instructions for implementing logical functions which can be embodied in any computer readable medium for use by or in connection with an instruction execution system or device (e.g., computer-based system, processor-containing system, etc.).

In one embodiment, the ontogeny engine 14 can provide the following functions:
from one cell, many cells can develop by cell growth, division, and death;
cells can descend from parent cells and so develop with lineage and sequential order;
cells can be semi-autonomous units, each with its own set of genes;
context-dependent, cell-by-cell control of gene expression via signaling;
construction and monitoring of an extracellular environment; and
higher order, emergent properties (e.g., self-repair).

The cell-centric simulator 11 can further include a physics engine 19 for running additional aspects of the cell-centric simulator instructions (e.g., physical interaction simulation, resolution of spatial and/or size constraints, etc.). In another embodiment, the cell-centric simulator can include an experiment engine 22 for running additional aspects of the cell-centric simulator instructions (e.g., dynamic adjustment of simulation activities, spawning new simulations, etc.) For clarity, the ontogeny engine 14 is shown separate from the physics engine 19 and the experiment engine 22; however, one of ordinary skill in the art will recognize that the ontogeny engine 14 could include the function of the physics engine 19, the experiment engine 22 and/or other functional features relating to the cell-centric simulator 11.

In another embodiment, the simulation system 10 can also include an evolution engine 20 for running further simulation instructions relating to simulated genome integrity, evolutionary fitness, etc. In a further embodiment, the simulation system 10 can include and/or be in communication with adjunct utilities 21 for providing additional programming and/or operation options and support.

Figure 1B:
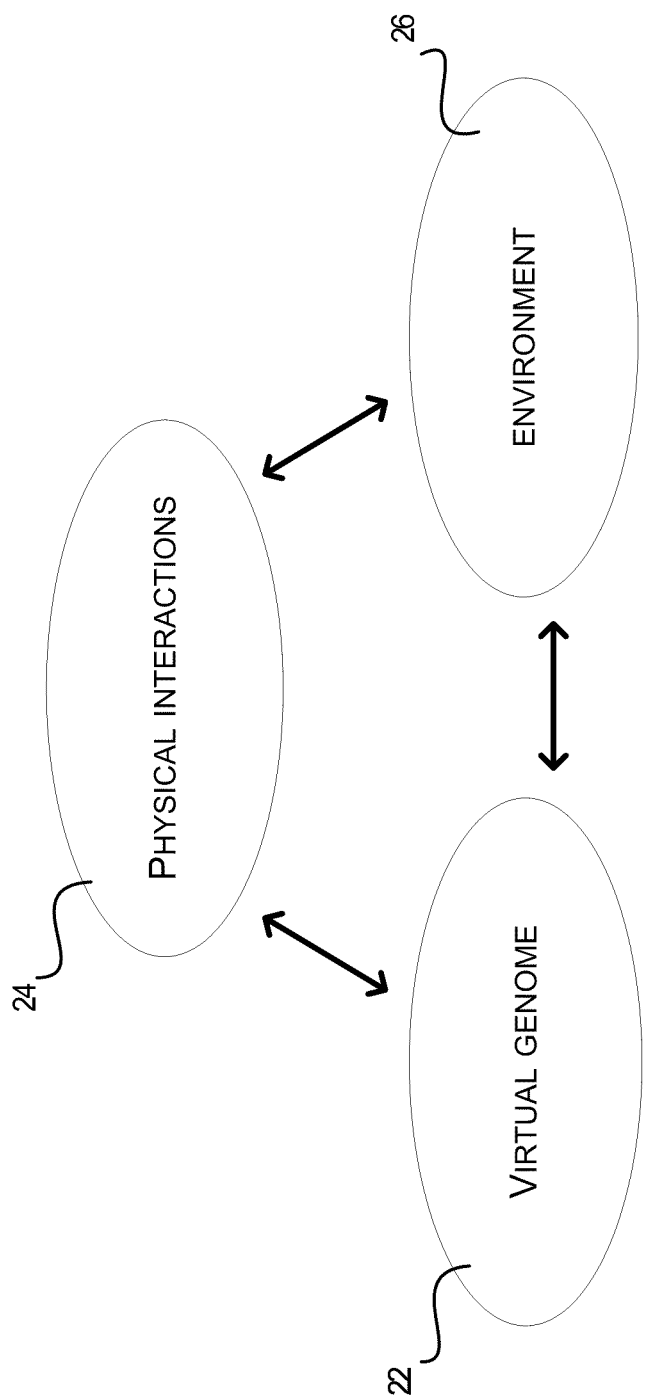
FIG. 1B is a schematic block diagram illustrating aspects of the simulation environment for modeling a biological event in accordance with an embodiment of the disclosure.

FIG. 1B is a schematic block diagram illustrating aspects of the simulation environment for modeling a biological event in accordance with an embodiment of the disclosure. In one embodiment, the ontogeny engine 14 runs aspects of the cell-centric simulator instructions for defining and characterizing the following elements: (i) a virtual genome 22 which specifies the gene units (e.g., control region and structure region) present in a cell; (ii) physical interactions 24, which specifies how the cells move and occupy space during cell growth, division, death, within a tissue, etc.; and (iii) an environment 26 in which the cells will grow.

The simulated and/or configured elements relating to the virtual genome 22, physical interactions 24 and the environment 26 interact within the simulated environment, as illustrated by the arrows in FIG. 1B. For example, status and/or activation of gene units present in a cell depend on both signal molecules in both the micro- and macro-environments, and accordingly, gene products simulated by activation of a gene unit contribute to the changing of both the micro- and macro-environments. Biological events, such as cell division and cell growth can occur as a result of the changing molecules (e.g., invoked action rules), and such events can alter the physical interactions modeled between cells and their environment (e.g., neighboring cells, substrate, spatial constraints, etc. In principle, any of these elements 22, 24 and 26 can be adjusted to devise the generation of a given tissue or a given tissue's response to a perturbation.

In addition, the cell-centric simulator instructions can contain chemistry equations that can be invoked to simulate the extra-genetic activity of molecules, including gene products and molecules from the environment. The chemistry equations can be configured to model the molecular interactions that occur normally within cells (e.g., how the molecules behave independent of the cell genome). For example, chemistry equations can be used to simulate the rate of turnover of the molecules, molecular binding and/or reaction effects, etc.

Configurable simulation information for initializing the ontogeny engine 14 can also be accompanied by configurable simulation information relating to criteria for suitability, a basis for evaluating the outcomes of many schemes for development—different gene interactions, physical constraints, environmental conditions, etc. These criteria, analogous to evolutionary processes of selection and descent with modification from ancestral forms, may be provided by the evolution engine 20 for modeling the concept of tissue "fitness". For example, the evolution engine 20 can include one or more functional modules for generating and/or evaluating a plurality of virtual genomes. In one embodiment, a fitness factor, which can form a basis for selecting preferred and/or "more fit" genomes, can be used to compare the modeled tissue (e.g., during and/or post simulation) with one or more characteristics of a desired target tissue. Evaluation and selection by a fitness criterion can establish a basis for competition among the members of a population of solutions, and a strategy for iterative improvements whereby the most successful solutions of one generation contribute more to the next generation (e.g., simulated cell divisions, cell replacement in a virtual tissue, etc.).

The selection and evaluation process provided by the evolution engine 20 can be useful when simulations of the modeled cells and tissue can be specified with precise coordinates, such as an "egg carton" model wherein each cell is assigned to a specified bin. Alternatively, when using a model where the cells are allowed to adopt positions in free space, and assume a variety of sizes and shapes, it may be more practical to employ the visualization model 12 to visually compare the modeled tissue with the target tissue, and make empirical adjustments to the genome or environmental conditions, to achieve a closer match between the modeled and target tissues.

In biology, genes provide a resource for cells by providing a template from which proteins and other molecular molecules (e.g., non-translated ribonucleic acids) can be synthesized. As such, the cell-centric simulator 11 provides each virtual cell with a virtual genome, e.g., a set of gene unit templates for simulating protein production and molecule synthesis for generating and coordinating a multicellular aggregate during a simulation session. For gene units to simulate natural genes for modeling a biological event, e.g., a developmental process, there can be a means to control how, where and when particular gene units are activated (e.g., generate a molecule increase). To represent these features in a computational model, each gene unit within a virtual genome contains both a control (e.g., regulatory) region and a structural (e.g., designating a functional gene product) region. Gene unit activation is controlled by the interaction of molecules (e.g., representing transcription factors) in the internal micro-environment of the virtual cell with the control region (e.g., configured simulation parameters specific to that gene unit), in a manner analogous with gene regulatory networks in vivo.

In biology, genes contribute to the biological potential of scale whereby complexity arises from a relatively simple set of genetic encodings. Yet for this potential to be realized, genetic information must be rendered by a process of self-construction, e.g., by development. Self-construction by living systems is driven in a manner that harnesses the power of genetic encodings to ensure heritability of traits, while packaging them in an encoded form that is compact enough to place into a single cell, the smallest living unit.

Integration of gene units into biological simulations (e.g., in the context of development) can rely on understanding characteristics of the gene product encoded by the natural correlate gene sequence, e.g., in the manner that it contributes to cellular function or its coordination in the growing multicellular tissue). For instance, some genes encode sensor molecules that allow cells to propagate signals to the ECM and to neighboring cells, while other genes encode receptor molecules that allow cells to detect signals from neighboring cells. However, while genes determine the types of sensors a cell can make, genes do not specify the patterns of information that the cell can receive.

Figure 2:
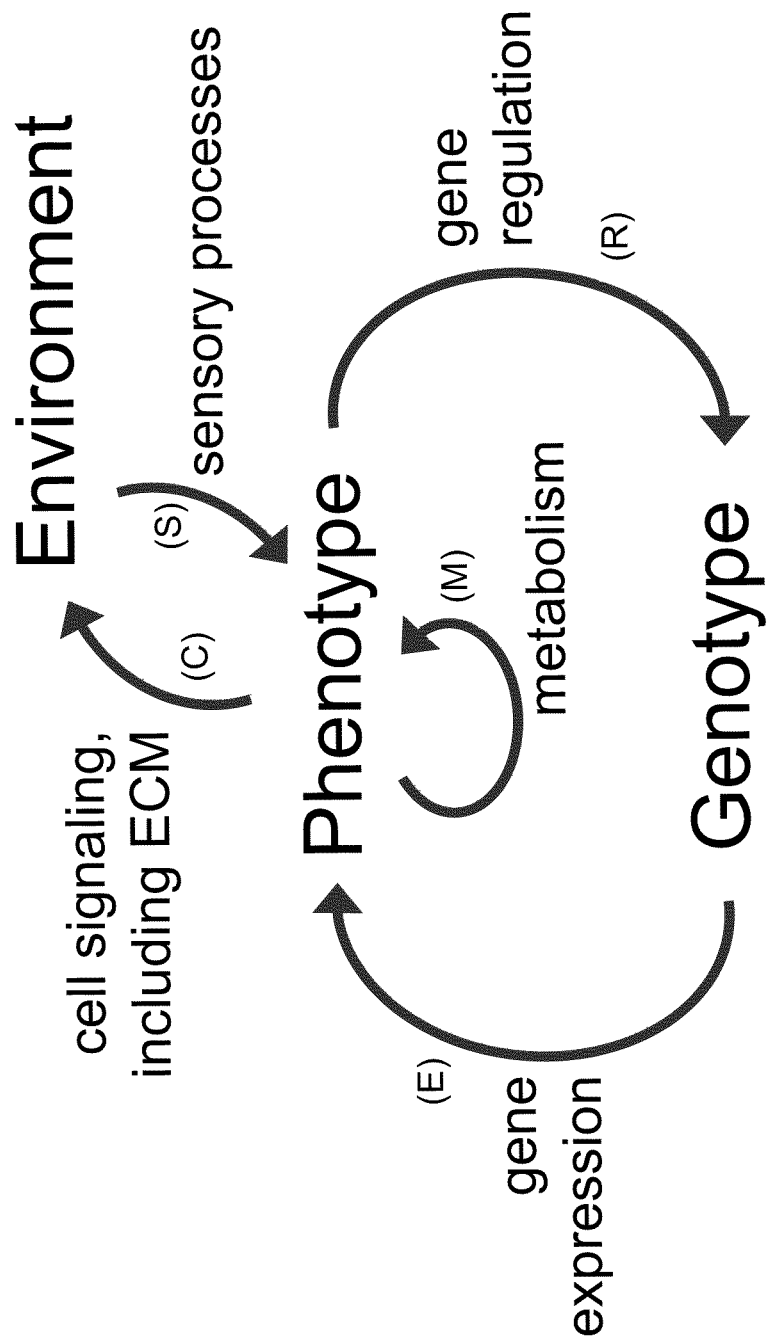
FIG. 2 is a schematic flow diagram of an ontogeny model illustrating the relationship between gene expression, metabolism, cell signaling, sensory processes and gene regulation in accordance with an embodiment of the disclosure.

FIG. 2 is a schematic flow diagram of an ontogeny model illustrating the relationship between gene expression, metabolism, cell signaling, sensory processes and gene regulation in accordance with an embodiment of the disclosure. The ontogeny engine 14, which runs aspects of the cell-centric simulator instructions, can be configured to simulate biological processes configured in accordance with the ontogeny model depicted in FIG. 2. For example, the cell-centric simulator instructions can include simulation information related to genetic encoding, a process of self-construction analogous to biological development, as well as environmental influences of the processes by which the organism and/or cell is so constructed. Although FIG. 2 illustrates genotype, phenotype, and environment as separate domains of influence on the process of development (e.g., ontogeny), the arrows indicate that these influences can be interdependent and overlapping.

As seen in the ontology model illustrated in FIG. 2, genotype can influence phenotype through gene expression (E) and internal cellular metabolism (M), while phenotype acts on the genome by regulating overall gene activity (R). The phenotype influences the local environment of adjacent cells by cell signaling (C), for example, by release of cellular products into the environment. In turn, the phenotype is acted upon by the local environment through sensory processing (S), for example, extracellular molecules acting on cell receptors, extracellular molecule transport into cells, etc. Accordingly, phenotype represents a higher ontological category than genotype, since the phenotype has access to genetically encoded information and information in its environment that is not so encoded.

Patterns of gene expression in cells, or across an entire tissue or organism are derived from functional controls each cell applies according to and/or in response to both the internal and external signals it receives. In contrast, signal molecule concentration(s) are locally defined by the position a cell occupies in the developmental field. For example, localized concentration(s) of signal molecules can depend on the type and level of molecules produced by the cell's neighbors, as well as by signal molecules retained in the extracellular matrix (ECM). In biology, microenvironments and mechanisms for control of gene expression provide the basis for differentiation.

In addition to their role in development, genes serve a passive role as units of inheritance, the units for transfer of information across generations. For genes to serve as units of inheritance they must have a stable, but not completely unchangeable, structure. For example, changes that occur in the structure (e.g., the coding sequence) of genes are passed on to progeny.

Emergence is a term that conveys many meanings, and accordingly, a broad range of phenomena have been classified as emergent (Steels, L. [1994] The artificial life roots of artificial intelligence. *Artificial Life I*, [no. 1,2]:75-110; Morowitz, H [2002]. *The Emergence of Everything*. Oxford Univ. Press, Oxford UK. 209 pp.). As used herein, emergence refers to a relationship among cell primitives in a multi-cellular system. In one embodiment, a specific arrangement or interaction among cell primitives produces the emergent behavior, such that the behavior is not a property of any single cell primitive. Typically, emergence refers to behaviors or dynamic states rather than static shapes or structures. In living systems, emergence can convey one or more additional meanings: 1) that the property of interest appears only at some higher level of hierarchical organization than the elements that give rise to it; and 2) that the emergent behavior is adaptive, that it carries survival value, or increases fitness. For instance, homeostasis among vertebrates (e.g., maintenance of blood composition within narrow limits) can satisfy both of these conditions.

As described in more detail below, the cell-centric simulator 11 provides means for simulating one or more biological events such as those that model the naturally occurring events and interrelationships described above. For example, the cell-centric simulator can model development of a tissue, differentiation of specialized cells, wound healing, immune system responses, neurological processes, etc. In operation, the cell-centric simulator 11 provides means for receiving configurable simulation information. Such configurable simulation information can include both macro- and micro-environmental parameters, as well as cell-specific parameters. Cell-specific parameters can include, for example, features characterizing the plurality of gene units that make up the cell's virtual genome, the defined state and/or maturity level of the cell at an initial step boundary (e.g., at the beginning of a simulation session), etc. Further, configurable simulation information can include a plurality of rules and equations that model the interrelationships between the object oriented molecules (e.g., gene unit products, nutrients, receiver molecules, signaling molecules, etc.). Additional configurable simulation information can include physical rules that are invoked to model the physical laws of nature (e.g., contact inhibition, size constraints, gravity, affinity/adhesion parameters between molecules and/or cells, etc.). In one embodiment, configurable simulation information can be interpreted by the cell-centric simulator source code for running a simulation.

Additionally, embodiments of the present disclosure have demonstrated utility for simulating emergent properties, such as those described above (e.g., self-repair, cell communication that leads to a desired phenotype, dynamic adaptability to a changed environment, feedback networks that respond to a dynamic environment and model oscillations of cell state that can propagate through a modeled multicellular tissue, etc.). In particular, emergent properties simulated by the cell-centric simulation system 10 can include the following:

differentiation and/or cell specialization from an initial state to a terminal state;
communication by sensory functions and exchange of signals;
homeostasis by regulatory processes and metabolic feedback;
metabolism of fuels, energy, and molecular synthesis;
self-repair through cell turnover, regeneration, and replication; and
adaptation by phenotypic plasticity.

Figure 3A:
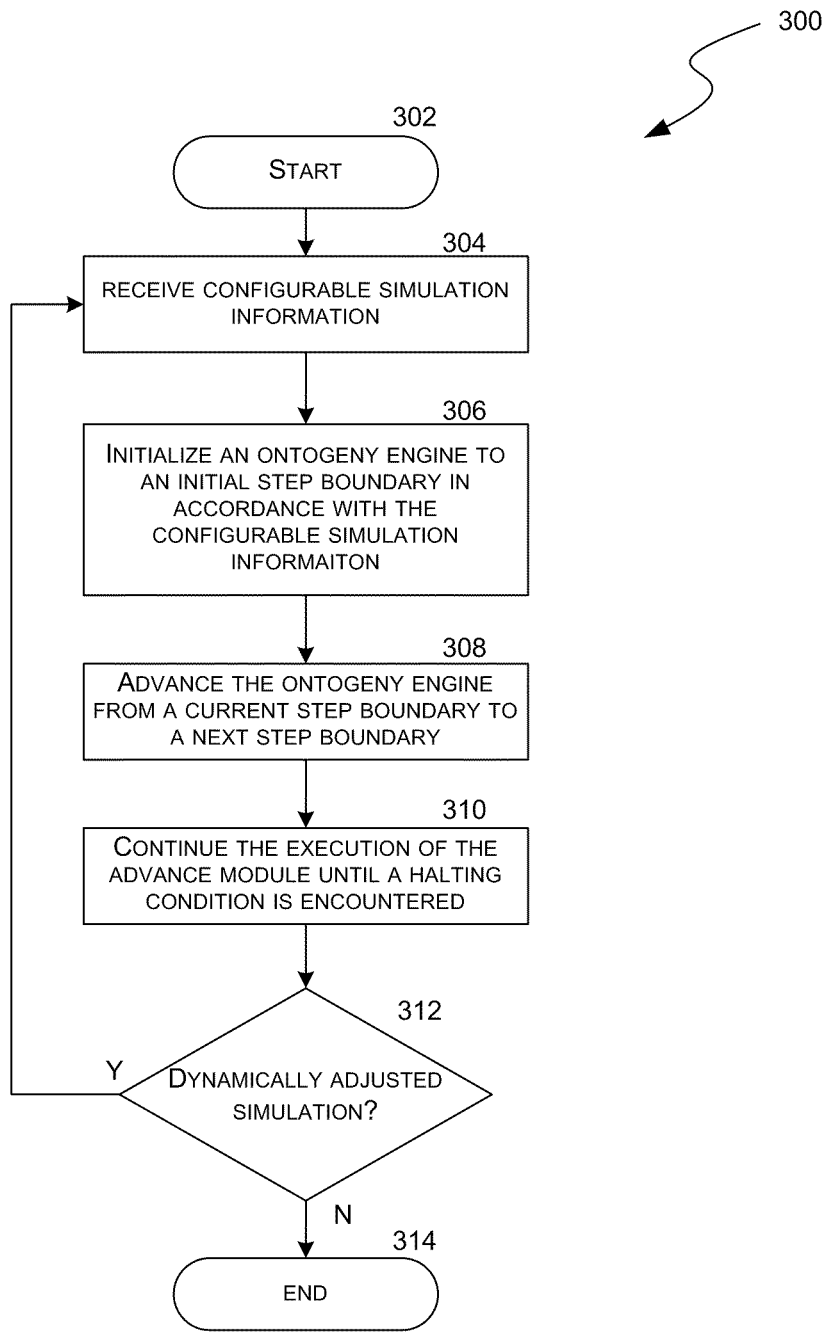
FIG. 3A is a flow diagram illustrating a routine for modeling one or more biological events invoked by the simulation system and in accordance with an embodiment of the disclosure.

FIG. 3A is a flow diagram illustrating a routine 300 for modeling one or more biological events invoked by the simulation system 10 in some embodiments. The routine 300 can be invoked by a computing device, such as a client computer or a server computer coupled to a computer network. In one embodiment, the computing device includes the cell-centric simulator 11 having the ontogeny engine 14. As an example, the computing device may invoke the routine 300 after an operator engages a user interface in communication with the computing device.

The routine 300 begins at block 302 and the receive module receives configurable simulation information (block 304). In some embodiments, the configurable simulation information can include user-configurable simulation information received from a user interface. In additional embodiments, the configurable simulation information can include information in a configurable file generated from a previous modeling session. The initialize module initializes the ontogeny engine to an initial step boundary in accordance with the configurable simulation information (block 306). In one embodiment, the initial step boundary can define a reference point from which a simulation can commence or continue. For example, the initial step boundary can define the static starting "state" from which subsequent steps may be taken. In the present implementation, the ontogeny engine can be driven one step at a time from the initial step boundary to subsequent step boundaries.

The advance module advances the ontogeny engine from a current step boundary to a next step boundary in accordance with the configurable simulation information and the current step boundary (block 308). In one embodiment, the advancing includes performing a stepCells function (described in detail below). In another embodiment, the advancing can include performing one or more of a killCells function, a stepECM function and stepPhysics function. One of ordinary skill in the art will recognize that the killCells, stepCells, stepECM and stepPhysics functions can be implemented in any combination, in sequential order, in non-sequential order, and/or simultaneously (e.g., to model a biological even in a continuous manner).

A halt detection module continues the execution of the advance module until a halting condition is encountered (block 310). The routine 300 may then continue at block 312, where it ends.

In one embodiment, a halting condition can be a halt command received from an operator (e.g., user) of the system at a user interface, for example. In another embodiment, the halting condition can be a configured halting condition and the halt detection module continues the execution of the advance module until the configured halting condition is detected during simulation. For example, the configured halting condition can be a preset number of advancements by the ontogeny engine from a current step boundary to a next step boundary and the halt detection module can halt the advancement module when the preset number of advancements has been exhausted. In another embodiment, the configured halting condition can be a condition in which a degree of change (of one or more parameters) between a current step boundary and a next step boundary is less than a threshold degree of change. For example, a simulated biological process can be configured to continue through step advancements until a virtual tissue reaches a state of homeostasis.

In another embodiment, the cell-centric simulator 11 can be configured to model a biological event in a continuous and/or asynchronous manner. For example, the initialization module can be configured to initialize the ontogeny engine to an initial step boundary such that the initial step boundary includes one or more virtual cells initialized in a virtual environment. The advance module can be configured to advance the ontogeny engine from a current step boundary to a next step boundary, wherein the advancing includes advancing each of the one or more virtual cells in the virtual environment independent of each of the other virtual cells. For example, the advancing can include the killCells function, the stepCells function, the stepECM function and/or the step Physics function (e.g., "the functions") operating on each virtual cell independently from the other virtual cells. In operation, the functions can be invoked in a first virtual cell or, in another embodiment, in a first subpopulation of cells at a different time and/or rate than in a second virtual cell or second subpopulation of cells. Accordingly, a step boundary for one cell can occur independent of a step boundary in an adjacent cell. In this manner, the cell-centric simulator can operate in a continuous manner and/or in a manner in which virtual cells can exhibit differential behavior.

In some embodiments, the visualization engine can generate and display a graphical image representing the current step boundary at a user interface. In one example, the graphical image can be a first graphical image, and the visualization engine can display a second graphical image representing the next step boundary in sequential order following the display of the first graphical image. In another embodiment, the visualization engine can provide progressive display of a plurality of graphical images either in real-time mode (e.g., during simulation), or off-line at one or more times following simulation. For example, the visualization engine can retrieve and render simulation data stored in files for replaying the simulation session (e.g., on a client computer, on a server, etc.). In a further embodiment, the visualization engine can provide a user interactive interface such that an operator can, in real-time, make a change to the simulation (e.g., perturb the environment, change a gene unit in one cell so that cell division and/or growth are not inhibited by neighbor cells, etc.). For example, the routine 300 (at decision block 312) can accommodate adjustment information received (at block 304) from the visualization engine user interactive interface, for initializing the ontogeny engine to an initial step boundary in accordance with the adjustment information.

In some embodiments, not shown, the output module can transmit simulation data to one or more data storage devices. In one embodiment, the output module can generate and transmit a recording file following the end 312 of the routine 300, wherein the recording file can be accessed at a subsequent time to "replay" the simulation, e.g., by the visualization engine. In another embodiment, the visualization engine can retrieve and render the recording data in the recording file such that a visual output of the recording can be manipulated (e.g., cells can be colored, cell connections displayed, visualize subspheres, rotate a point of reference, etc.). The visualization engine can also be configured to replay an entire simulation recording form the recording data, or in another embodiment, replay a sub-portion. Further, the visualization engine can capture "snap shot" images from the recording data in the recording file, e.g., from selected step boundaries.

In one embodiment, configuration files can be generated at any point (e.g., at any step boundary) during a simulation session, including a stop boundary (e.g., when a halting condition is encountered), transmitted (e.g., by the output module) and can be stored for later retrieval. For example, configuration files corresponding to any of the initial step boundary, $1^{st}$ step boundary, $2^{nd}$ step boundary, . . . $n^{th}$ step boundary, $n^{th}+1$ step boundary, . . . stop boundary, etc., can be generated and stored for subsequent retrieval. In one embodiment, configuration files can include simulation information, including all configurable information used during the initiation of the ontogeny engine, as well as simulation information regarding the current step boundary from which the file was generated. In one embodiment, the experiment engine can be configured to access and retrieve a stored configuration file generated during a previous simulation session such that the configuration file can be used to run additional simulations. For example, a selected configuration file can be received by the receive module at block 304 (e.g., from the experiment engine) and the initialize module, at block 306, can initialize the ontogeny engine to an initial step boundary in accordance with the configurable simulation information provided in the selected configuration file. Accordingly, configurable simulation information derived from any step boundary and/or stop boundary can be used to initialize the ontogeny engine and, e.g., define an initial step boundary for initiating further simulation sessions.

In some embodiments, the experiment engine 22 can include a user-interface module 23 (FIG. 1A) for supporting user-selection of the configuration file. For example, the configuration file can be a user-selected file, and be selected from a plurality of stored configuration files. In such embodiments, the operator may be queried by and/or instruct the experiment engine to further alter the configurable simulation information stored in the configuration file. For example, the operator can perturb selected parameters (e.g., gene units, environmental parameters, chemical equations, action rules, etc.) and/or alter a simulation protocol prior to the initialization of the ontogeny engine at block 306. Accordingly, the simulation system can be used for iterative experiments and queries by an operator by running subsequent simulation sessions having selected parameters altered. An operator can compare results from a plurality of modeled sessions.

In a particular and non-limiting example, an operator may want to determine if and how development of a tissue can be altered when the cells are starved for nutrients at an intermediate point during development. In this example, an operator can choose to run a first simulation session wherein the configurable simulation information codes for a high level of modeled nutrient molecules. In a second simulation session, the operator can select a configuration file generated during an intermediate step boundary (e.g., $1^{st}$ step boundary, $2^{nd}$ step boundary, . . . $n^{th}$ step boundary, $n^{th}+1$ step boundary, . . . etc.). Following selection of the desired configuration file, the receive module can receive, at block 304, the configuration file and additional configurable simulation information, wherein the additional information instructs a low level of modeled nutrient molecules. The initialize module can initialize the ontogeny engine (block 306) as described above and modeling of tissue development can "continue" from the selected intermediate step boundary while in a virtual environment depleted of nutrient molecules. The operator can compare results of the first simulation session to the second simulation using, for example, the visualization engine, or some other data output device.

In other embodiments, the experiment engine 22 can be configured with additional programming logic for automatically selecting configuration files from which additional and/or different simulations can be generated. For example, a simulation session can be automatically implemented using the simulation system without requiring an operator to manually input or otherwise specify the configurable simulation information.

In one embodiment, experiment engine 22 can include a dynamic adjustment module 24 for capturing configuration files and automatically initiating additional simulation sessions for modeling biological events. One of ordinary skill in the art will recognize that the dynamic adjustment module 24 includes configurable hyper-directives (e.g., programmed rules for generating rules). Such hyper-directives allow the spontaneous generation of rules so that the dynamic adjustment module can automatically, and in real-time, run a plurality of directives in accordance with a plurality of simulations.

In one aspect, the dynamic adjustment module can be configured to recognize instances (e.g., at step boundaries, at a stop boundary, etc.) wherein criteria are met for generating a second or multiple simulation sessions. For example, the dynamic adjustment module can be configured to automatically spawn a second simulation following or to run concurrently with a first simulation (decision block 312). In such embodiments, the routine 300 may then continue at block 304, wherein the receive module receives configurable simulation information.

In further embodiments, the dynamic adjustment module 24 can be configured to alter a captured configuration file and/or user-configurable simulation information over multiple simulation sessions, such that the equivalent of multiple experiments can be simulated automatically. For instance, the dynamic adjustment module 24 can systematically and/or randomly alter the control region parameters (e.g., simulating constitutively active expression of a gene, simulating a gene "knock-out" or "knock-down", etc.) of each of a targeted group of gene units in sequential simulation sessions. An operator can compare the results and/or final modeled output data from any simulation session (e.g., a first simulation session using a "wild-type" or normal gene unit configuration) to any other simulation session results (e.g., a second simulation session using a "knock-out" or absent gene-unit).

Figure 3B:
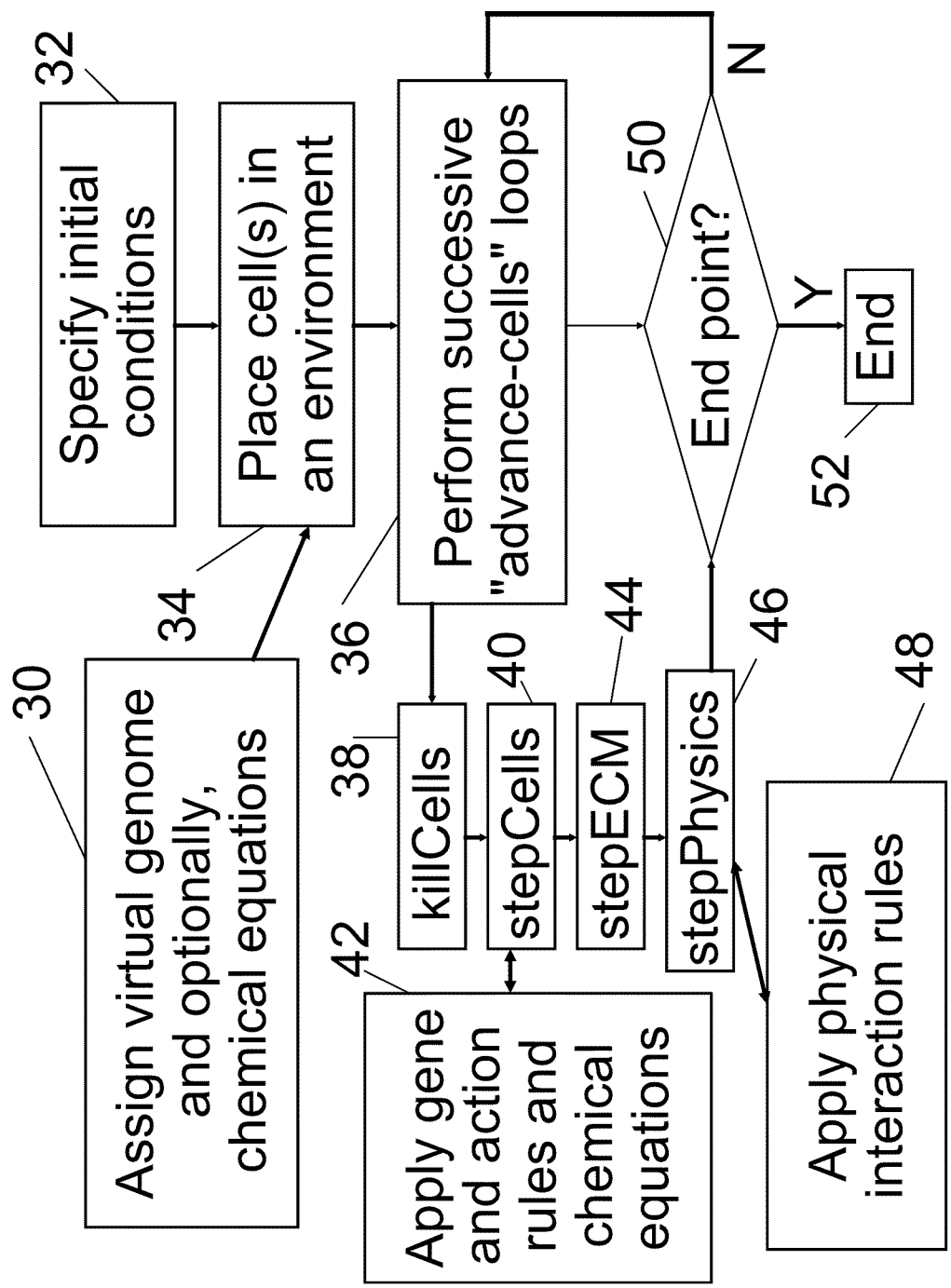
FIG. 3B is a flow diagram illustrating another routine for modeling a biological event supported by the simulation system and in accordance with an embodiment of the disclosure.

FIG. 3B is a flow diagram illustrating another routine for modeling a biological event supported by the simulation system 10 and in accordance with an embodiment of the disclosure. In block 30, a virtual cell (or cells) is assigned a virtual genome, e.g., a set of gene units, each with specified gene control and gene product characteristics (detailed in Section C below). In some embodiments, one or more chemistry equations that govern the extra-genetic behavior of the molecules present in an environment or generated as a result of gene unit activity can be specified (described below in Section C). In block 32, a simulated environment is generated through specification of initial conditions (e.g., spatial parameters, virtual substrate characteristics, molecule types [external signals] present, molecule density, molecule gradient(s) within the environment, available nutrient(s), quantity and distribution of nutrients, etc.). In block 34, one or more virtual cells can be placed in the virtual environment. For example, following blocks 30, 32 and 34, the ontogeny engine can be initialized to an initial step boundary (e.g., an initial static state in accordance with the configuration simulation information received in steps 30, 32 and 34).

Following initialization of the ontogeny engine, simulation of the one or more biological events includes advancing the ontogeny engine from a current step boundary to a next step boundary in accordance with the configurable simulation information and the current step boundary. Accordingly, at block 36, the state of each virtual cell can be advanced in steps. Advancing can include applying at each step, one or more of the functions indicated at blocks 38, 40, 44 and 46. One of ordinary skill in the art will recognize that the ontogeny engine can perform one or more of these functions in any combination and/or order. It will also be recognized that each function employed during the advancing of the ontogeny engine can be performed in a sequential and/or simultaneous manner. In a further embodiment, one or more functions can be performed in an asynchronous manner.

The "killCells" function is configured to eliminate virtual cells from the virtual environment/virtual tissue. The cells that are removed are the cells for which a cell death criterion was met (e.g., death gene unit activated, loss of activation of an essential gene unit, etc.) in the previous cell advancement step.

The "stepCells" function (block 40) is configured to update and/or refresh cell activity functions that are poised to be affected at that step, including gene activity, gene response, intracellular and intercellular signaling, etc. (described in more detail below). The stepCells function invokes the gene unit control region rules and chemistry equations (block 42) to determine the adjustment in the on/off and/or level of activity of each gene unit, change state of molecules acting within or on each cell, etc. For example, the chemistry equations and correlating changes in activity level of gene units can be applied to produce a "new cell state" for each cell. In response to new and/or step-wise refreshed interactions between molecules within a cell and each gene unit, each gene unit within the cell can contribute to the generation of molecules (e.g., increasing or decreasing the value of molecule strength in the cell, etc.). In biology, when a gene is turned on, the transcriptional machinery of the cell synthesizes corresponding ribonucleic molecules (RNA) that are defined by the gene's structural region (e.g., open reading frame). Many of these RNAs are, in turn, translated by the cell's translation machinery into proteins having specific functions. Likewise, when gene units are turned on, the simulation system is updated as though the gene units give rise to the correlative levels of the specific gene product for which the gene units represent. These newly generated molecules may in turn interact with the cell's other gene units (e.g., in the virtual genome), affecting rates and/or levels of transcription during the next round of applied stepCells function. In some embodiments, the stepCells function can include rules that independently determine rates and/or levels of transcription and translation operations of gene unit templates.

Simulation of biological events is thus governed, at each step advancement, through changes in the virtual environment (external to the cell), as well as changes to the internal cell environment. Using further complexity, a virtual cell can also be affected through chemical equations representing interaction with molecules generated by neighboring virtual cells. During simulation, the simplest neighborhood of a cell consists of those cells that are spatially adjacent to (touching) the cell of interest. However, a cell's neighborhood may be configured as any arbitrary group of cells. For example, a neighborhood (the cells to/from which it will send/receive signals) could include cells that are not adjacent, as occurs in vivo with cells that are able to signal non-local cells via hormones.

In one embodiment, the "stepECM" function (block 44) can be invoked at each advancing step to update and/or refresh simulated adhesion properties between virtual cells and a virtual ECM, for example. For instance, the stepECM function can be configured to execute rule-based directives for breaking overextended cell adhesions, forming cell adhesions between adjacent cells, weakening cell adhesions over time, etc. (discussed in more detail below).

In addition to operations that increase or decrease a molecule strength value (e.g., analogous to concentration) during simulation, additional actions, e.g., cell growth, cell division and optionally, cell death, are applicable to each cell and each of these action affect the environment's spatial parameters. The virtual genome of a cell can include gene units that serve as a template for growth molecules, division molecules, death molecules, etc., and as these gene units are activated during the simulation session, the concentration of encoded molecules in the cell's virtual cytoplasm increases. In some embodiments, growth and/or death can be a function of the concentration of these two types of molecules. When a cell accumulates a threshold level of a death molecule, it can be removed from the environment in a subsequent advancing step. In another example, if a cell grows, its overall size (e.g., spherical diameter, volume, etc.) is increased. In a further example, if a cell divides, a new cell is placed in a location adjacent to the parent cell. If all adjacent positions are already occupied, operation rules can prevent a cell from dividing. Such operation rules can supersede other factors, such as division and/or growth potential exceeding a predetermined threshold for meeting a division and/or growth action rule requirement.

In one embodiment, the "stepPhysics" function (block 44) can be invoked at each advancing step to update and/or refresh simulation of physical forces on the cells and/or molecules in the environment. For example, the stepPhysics function can move cells according to calculated forces in their environment (e.g., dividing cells, cell growth of neighboring cells, adhesion or attraction forces, etc. In one embodiment, the stepPhysics function is configured to resolve overlaps between cells that arise from cell growth, division, and/or motion, including motion from prior calculations for resolution of cell overlap. The stepPhysics function invokes physical interaction rules (block 48) for specifying cell adhesion forces, rules for applying natural physical laws and rules for simulating the mechanics of moving cells (e.g., apart from one another during resolution of cell overlap, toward one another to resolve excessive cell motion, etc.) The stepPhysics function, can in one embodiment, be provided by or reside in source code for running by the physics engine.

In one embodiment, the stepPhysics function operates using spatially defined models described further herein. For example, the stepPhysics function can operate using (1) a fixed-coordinate, discrete-coordinate, or egg-carton model in which cells are assigned to predetermined two- or three-dimensional coordinates in space, similar to the bins of an egg carton; (2) a free-space or continuous-coordinate model in which each cell is represented by a solid sphere which is free to assume arbitrary coordinates in two- or three-dimensional space; and (3) a free-space model in which the cells are identified by a plurality of subspheres (e.g., a "bag of marbles"), and therefore, are free to assume arbitrary non-spherical shapes, e.g., flattened shapes. In general, a free-space model gives a much closer approximation to real-cell behavior, and may be required for modeling certain tissue behavior. In one embodiment, during each "advance-cells" loop (block 36), the stepPhysics function (block 46) runs several cycles, e.g., 20 cycles or greater, to iteratively resolve cell movement and overlap.

As indicated in FIG. 3B, the "advance-cells" loop is repeated until a halting condition is encountered end point is reached, at 50, terminating the run at 52. This end point may be defined by a pre-selected number of loops, or when the tissue reaches a stable or steady state.

C. Virtual Genes and Chemical-Interaction Rules

Each virtual cell in the system is assigned a virtual genome containing a plurality of gene units, each of which has a control region that determines what combination of signals (e.g., molecules or conditions) will signal gene activity and at what level. Each gene unit also comprises a gene product region that specifies the gene product or action produced by the gene unit. Table 1 includes an exemplary group of gene units that represent a "basic" set of virtual genes that can be used during in a variety of simulation session, e.g., for tissue development applications. One of ordinary skill in the art will recognize additional and/or alternative gene units that can be included in a virtual genome. Furthermore, the listings in Table 1 are not meant to be limiting to the structure or context of code shown, and as such, other means and methods of coding and/or conveying gene unit information is considered within the scope of this present disclosure.

TABLE 1

Examples of Gene Units having Control and Gene Product Regions

| Gene Unit | Gene specification |
|---|---|
| 1 | [DiffuseNutrients .3] [Plasticity, Elasticity, Rigidity], |
| 2 | [DiffuseNutrients 5] [ExistanceSignal, ExistanceSignalReceiver], |
| 3 | [DiffuseNutrients .18, NeighborPresent −3] [Growth], |
| 4 | [DiffuseNutrients .18, NeighborPresent −3] [Division], |
| 5 | [DiffuseNutrients 5, Dominator −10, Dominated 5] [DominationSignalReceiver], |
| 6 | [NeighborPresent 3, Dominated −10, Dominator 3] [Dominator, DominationSignal] |

As shown in Table 1, each gene unit includes a paired control region and a gene product (e.g., structure) region. For example, referring to GENE 3 in Table 1, "[DiffuseNutrients 0.18, NeighborPresent −3] [Growth]" indicates that cell growth is promoted at (+)0.18 by DiffuseNutrients (a configured designation for molecules, in this case placed in the environment and transported into the cell) and, given its negative coefficient is inhibited at −3.0 by NeighborPresent. The actions invoked by these six genes units (e.g., cell growth, division, death, adhesion, etc.) are described in greater detail below.

Molecules present in the environment or generated within virtual cells are governed by extragenetic rules, referred to herein as chemical-interaction rules or chemistry equations, which can determine how molecules will be transformed or transported as they interact with other molecules in the system. Table 2 includes a listing of nine exemplary chemistry equations or chemistry-interaction rules that can be invoked when modeling a biological event. One of ordinary skill in the art will recognize additional and/or alternative chemistry equations that can be included in the cell-centric simulation instructions. Furthermore, the listings in Table 2 are not meant to be limiting to the structure or context of code shown, and as such, other means and methods of coding and/or conveying chemistry equation information is considered within the scope of this present disclosure.

TABLE 2

Example Chemical-Interaction Rules

| EQ # | CHEMISTRY EQUATION |
|---|---|
| 1 | {DiffuseNutrients} + (NutrientTransport) = 0.1 DiffuseNutrients + (1.11111111111111 NutrientTransport); |
| 2 | (NutrientTransport) = (1.11111111111111111 NutrientTransport); |
| 3 | (GenericExporter) = (1.11111111111111111 GenericExporter); |
| 4 | ExistanceSignal + (GenericExporter) = (1.1111111111111 GenericExporter) + {ExistanceSignal}; |
| 5 | ExistanceSignalReceiver = (ExistanceSignalReceiver); |
| 6 | {ExistanceSignal} + (ExistanceSignalReceiver) = 20 NeighborPresent; |
| 7 | DominationSignal + (GenericExporter) = (1.1111111111111 GenericExporter) + {DominationSignal}; |
| 8 | DominationSignalReceiver = (DominationSignalReceiver); |
| 9 | {DominationSignal} + (DominationSignalReceiver) = 20 Dominated + 20 GrowABit; |

The left side of the equal sign in each chemistry equation denotes the reactants and/or substrates, while the right side of the equation denotes the products and/or result of the reactant/substrate interaction. For instance, EQ 4 can be interpreted as follows: when ExistanceSignal is internal to the cell and GenericExporter is on the cell surface, as denoted by parentheses about the molecule name, the equation will produce 1+1/9 GenericExporter for every one GenericExporter in the reaction and produce ExistanceSignal molecule outside of the cell, as denoted by the braces about the molecule name. Since reactants are "consumed" in the execution of an interaction equation, the net effect is to replenish the GenericExporter and move ExistanceSignal from inside the cell to outside of it.

Chemistry equations can designate how internal or surface substrate molecules are converted to other internal or surface molecules, how molecules are transported across the cell membrane by surface molecules, and how molecules are relocated between a cell's interior and surface. Chemistry equations can also be used to consume molecules, thereby inhibiting their involvement in other and/or additional interactions.

Figure 4:
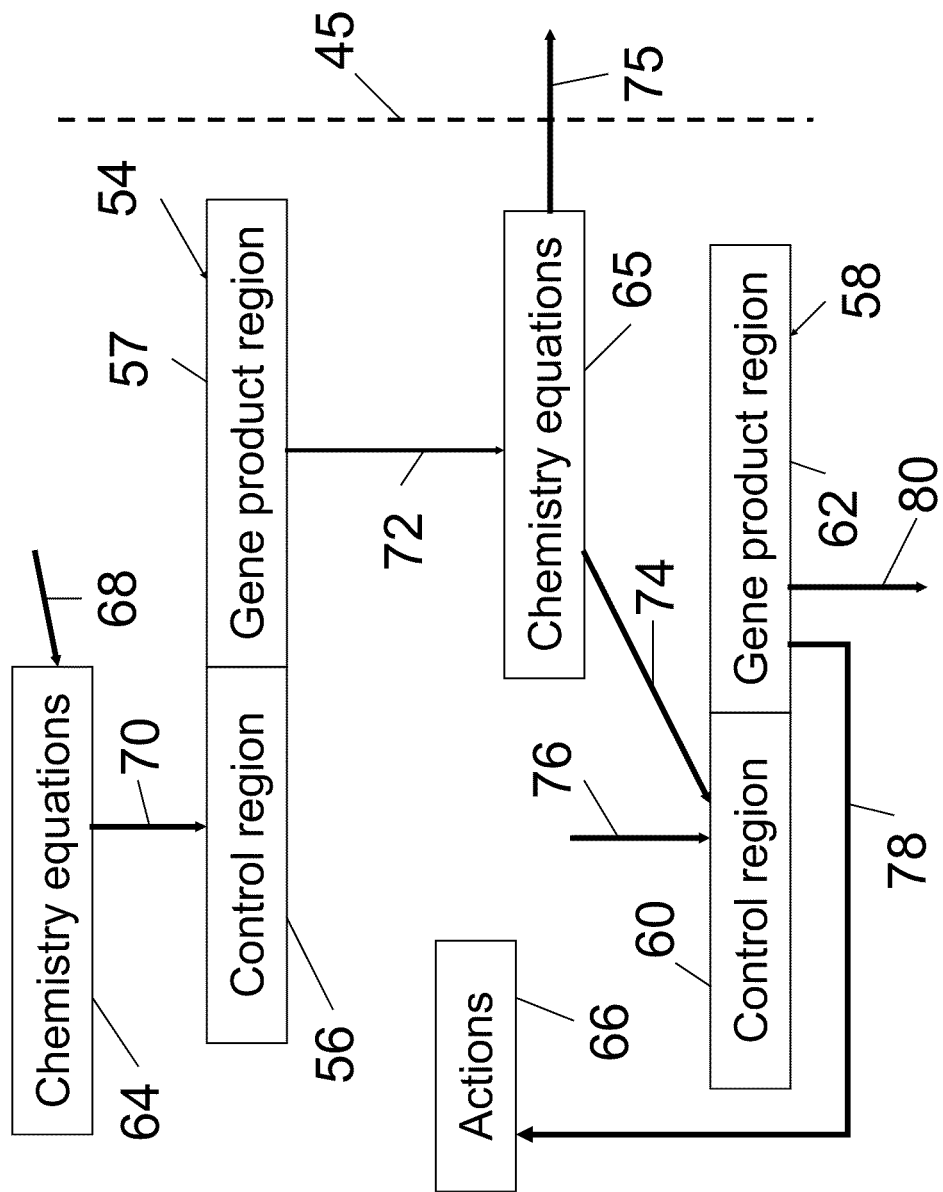
FIG. 4 is a schematic flow diagram illustrating interactions between gene units within a virtual cell in accordance with an embodiment of the disclosure.

FIG. 4 is a schematic flow diagram illustrating interactions between gene units within a virtual cell in accordance with an embodiment of the disclosure. For example, FIG. 4 illustrates two gene units within a cell, whose "outer membrane" (e.g., abstract separation between the interior and exterior of a cell), is indicated at 45. A first gene unit 54 has a gene control region 56 and a gene-product region 57. In this example, the first gene unit 54 generates a gene product that, in turn, can affect a second gene unit 58. As shown in FIG. 4, the product of the first gene unit can interact with a control region 60 of the second gene unit 58 to, for example, promote the second gene unit and thereby generate 80 a second gene product as indicated by the code of the gene-product region 62. In the example illustrated in FIG. 4, the second gene product invokes a specific action rule 66, and thereby triggers a cell-based action (e.g., cell growth, cell division, etc.).

To expand on the example illustrated in FIG. 4, assume a cell encounters 68 an intracellular signal which is transformed through first chemistry equation(s) 64 to produce 70 an intracellular molecule that has an affinity with the control region 56 of the first gene unit 54 for generating 72 a first product molecule. The first product molecule can trigger a second chemistry equation 65 for generating 74 another molecule having affinity to the control region 60 of the second gene unit 58. In one example, the presence of molecule generated at 74 is the result of the presence and/or availability of first product molecule and an interaction 75 between the cell of interest and a neighbor. Thus, if gene unit 58 in FIG. 4 corresponds to GENE UNIT 3 listed in Table 1 above, the gene control region 60 responds to the presence of both DiffuseNutrients (indicated by directly presented molecule 76), and NeighborPresent, indicated by molecule 74, to produce 80 a second gene product which is accumulated 78 in accordance with cell behavior actions 66 to cause the cell to grow, for example. The same general mechanisms of gene unit control, chemical-interaction rules and action rules can apply to GENE UNIT 4 (see Table 1) for cell division, for example. In another embodiment, GENE UNIT 1 (see Table 1), which controls cell adhesion events, can operate using similar gene regulatory mechanisms. One of ordinary skill in the art will recognize that gene units can operate using a variety of parameters and input, for example, GENE UNIT 1 may not require the presence of NeighborPresent.

Figure 5:
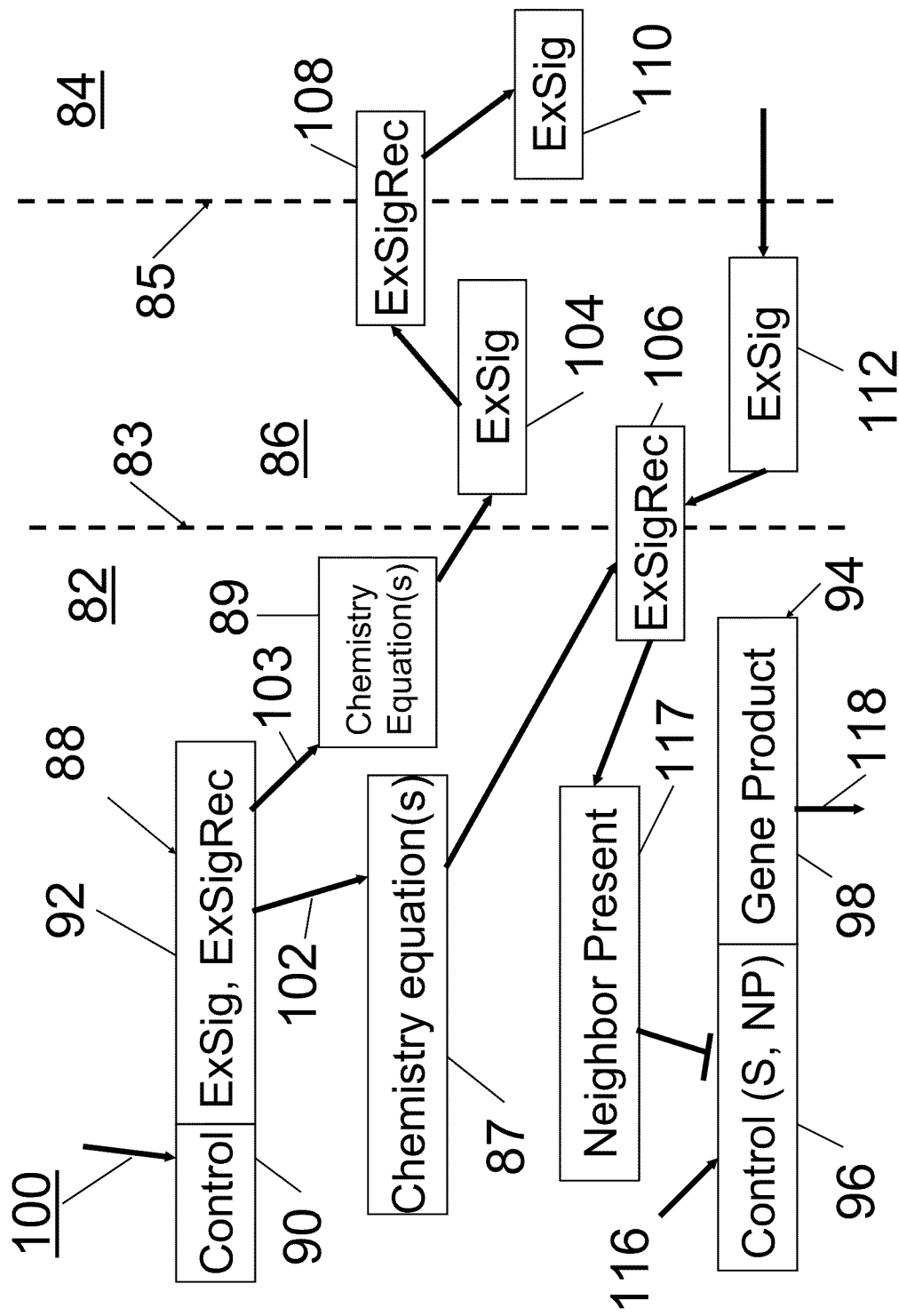
FIG. 5 is a schematic flow diagram illustrating interactions between gene units and gene unit products within a virtual cell and in a neighboring virtual cell in accordance with an embodiment of the disclosure.

FIG. 5 is a schematic flow diagram illustrating interactions between gene units and gene unit products within a virtual cell and in a neighboring virtual cell in accordance with an embodiment of the disclosure. For example, continuing with the GENE UNIT examples listed in Table 1, FIG. 5 illustrates how GENE UNIT 2 (see Table 1) present in neighboring cells leads to intercellular signaling. The two cells, with their interior environments, are indicated at 82 and 84 and separated by outer "membranes" 83 and 85 to define an intercellular space 86 between the two cells.

Referring to FIG. 5, virtual cell 82 contains gene unit 88. In one embodiment, gene unit 88 can be substantially similar to GENE UNIT 2 (see Table 1) and be configured to produce a gene product molecule for signaling and/or receiving signals to/from a neighboring virtual cell 84. Neighbor cell 84 may also contain a gene unit (not shown) substantially similar to gene unit 88 for producing a gene product molecule for signaling and/or receiving signals to/from the virtual cell 82, among others. Gene unit 88 includes a control region 90 which can be responsive to DiffuseNutrients, and a gene product region 92. Upon promotion 100 of gene unit 88 by the presence of DiffuseNutrients gene unit 88 generates 102 and 103 both ExistanceSignalReceiver and ExistanceSignal molecules. One or more chemistry equations 87 (e.g., EQ 5 listed in Table 2) can be used to simulate transportation of the ExistanceSignalReceiver to position 106 at the outer membrane 83 of the cell 82. Once the ExistanceSignalReceiver is at position 106, it can trigger a second chemistry equation (not shown in FIG. 5; e.g., EQ 6 listed in Table 2) with external ExistanceSignals 112 from one or more neighboring cells 84. The second chemistry equation can trigger the generation of NeighborPresent molecule 117 that can, in turn, act on gene unit 94.

A third chemistry equation 89 (e.g., EQ 4 listed in Table 2) can trigger a move 103 of the ExistanceSignal (e.g., if a GenericExporter is also present), from inside cell 82 to the intracellular space 86 at location 104. In this example, ExistanceSignal 104 can interact with ExistanceSignalReceiver 108 on the outer membrane 85 of neighboring cell 84. Accordingly, ExistanceSignal can be further moved into cell 84 at location 110.

In one embodiment, gene unit 94 can be substantially similar to GENE UNIT 3 (see Table 1). Gene unit 94 can include a gene control region 96 and a gene product region 98. In this example, the gene control region 96 can be inhibited by NeighborPresent 117 and responsive 116 to a DiffuseNutrient molecule. In one embodiment, the Diffuse-Nutrient molecule can be a molecule configured to trigger cell growth or division, through action triggered 118 by gene unit product molecules. In one embodiment, chemistry equations EQ4 through EQ6 (listed in Table 2), along with gene units 88 and 96, can provide resemblance to intercellular signaling between neighboring cells for inhibiting cell growth and division. In other embodiments, additional gene units can be provided for simulating intercellular signaling and/or other modes of cellular signaling.

Figure 6:
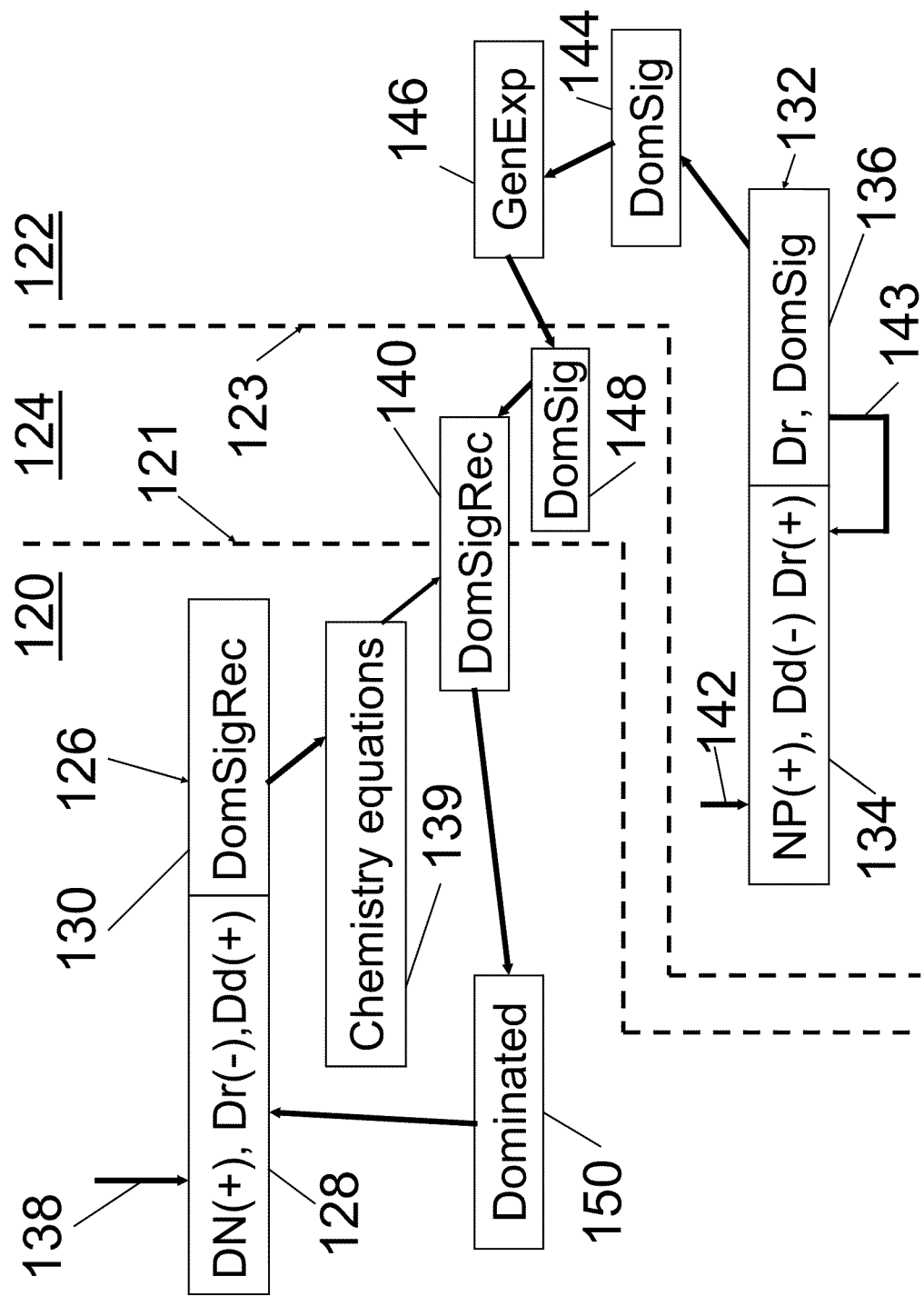
FIG. 6 is a schematic flow diagram illustrating interactions between gene units and gene unit products capable of establishing cell state in a virtual cell and in a neighboring virtual cell in accordance with an embodiment of the disclosure.

FIG. 6 is a schematic flow diagram illustrating interactions between genes units and gene unit products capable of establishing cell state in a virtual cell and in a neighboring virtual cell in accordance with an embodiment of the disclosure. For example, continuing with the GENE UNIT examples listed in Table 1, FIG. 6 illustrates how gene units (e.g., GENE UNIT 5 and GENE UNIT 6 listed above in Table 1) present in a virtual genome can influence a change in the relative status of two neighboring virtual cells. In some embodiments, the mechanism illustrated in FIG. 6 can be self-reinforcing, such that a cell can remain in a given state (e.g., analogous to a state of differentiation in a living biological tissue).

The two cells, with their interior environments, are indicated at 120 and 122 and separated by outer "membranes" 121 and 123 to define an intercellular space 124 between the two cells. Cell 120 is shown having a first gene unit 126 (e.g., GENE UNIT 5 listed in Table 1) which includes a control region 128 that responds 138 positively to Diffuse-Nutrients, negatively to Dominator molecules, and positively to Dominated molecules 150. The gene unit product region 130 can be configured to generate a DominationSignalReceiver molecule which can be transported to the outer membrane 121 of the cell 120 at location 140 through chemistry equation 139 (e.g., EQ8 listed in Table 2).

Cell 122 is shown having a gene unit 132 (e.g., GENE UNIT 6 listed in Table 1) which includes a control region 134 that can respond 142 positively to NeighborPresent molecules, negatively to Dominated molecules, and positively to Dominator molecules. The gene unit product region 136 can be configured to generate 143 both Dominator and DominationSignal molecules. In this example, the Dominator molecules generated from gene unit 132 can, via one or more chemical-interaction rules, inhibit the control region 128 of gene unit 126 as well as positively promote the control region 134 of gene unit 132 (illustrated by loop 143 in FIG. 6).

In one embodiment, simulation conditions can favor increased promotion of gene unit 132 in cell 122, causing a further promotion of the gene unit (and additional generation of gene unit product molecules) through feedback loop 143. The gene unit product of gene unit 132 includes DominationSignal 144, which can be transported out of the cell 122 if a GenericExporter 146 is present (e.g., via a chemistry equation, such as EQ 7 listed in Table 2). Gene unit 126 in cell 120, through the presence of DiffuseNutrients, can generate DominationSignalReceiver molecules, which can subsequently be moved to the cell outer membrane 121 to location 140 via a chemistry equation as described above (e.g., EQ8 listed in Table 2). When DominationSignal molecules 148 are located in the extracellular space 124, these molecules can interact with DominationSignalReceiver 140 on outer membrane 121 of cell 120. If this interaction occurs within the simulated environment, a chemical-interaction rule (e.g., EQ 9 listed in Table 2) can generate Dominated molecules 150 within cell 120. In turn, the Dominated molecules can positively promote gene unit 126, causing an increased accumulation of DominationSignalReceiver on the outer membrane 121 of cell 120. Conversely, cell 122, through its initial activation of gene unit 132, can continue to generate increasing levels of Dominator and DominationSignal molecules, which can inhibit generation of DominationSignalReceiver in cell 122 (not shown). Thus, if each cell 120 and 122 each include gene units, such as GENE UNIT 5 and GENE UNIT 6 as listed in Table 1, the two virtual neighboring cells can be promoted to opposing and self-sustaining cell "states." In one embodiment, a cell "state" may only be disrupted and/or reversed when one or more virtual neighboring cells is eliminated from the virtual environment, for example, by invoking a cell death event.

Figure 7A:
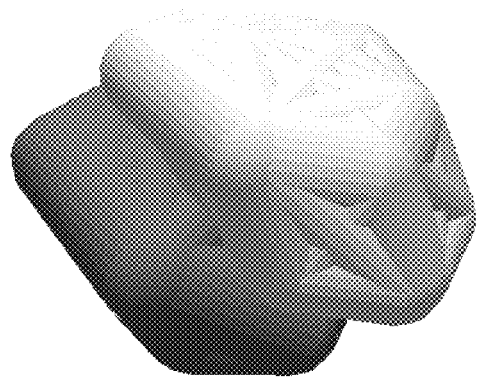
FIGS. 7A-7C are isometric views illustrating a simulation of a cell division event including an initial cell division event and a differentiation event resulting in two cell types (7A), a second cell division event resulting in two cells representing each cell type (7B), and a reversion event (7C) in accordance with embodiments of the disclosure.
Figure 7C:
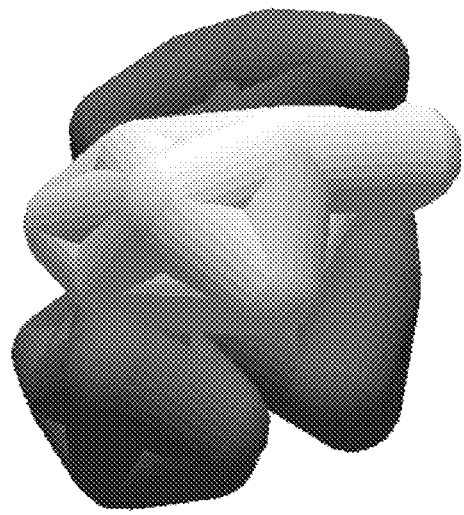
Figure 7B:
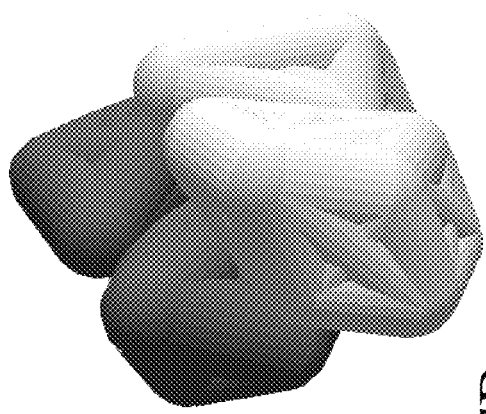

FIGS. 7A-7C are isometric views illustrating a simulation of a cell division event including an initial cell division event and a differentiation event resulting in two cell types (7A), a second cell division event resulting in two cells representing each cell type (7B), and a reversion event (7C) in accordance with embodiments of the disclosure. In one embodiment, an initial virtual cell having a configured virtual genome can be placed into a virtual environment having a specific molecular profile. Aspects of an emergent signaling and gene regulatory network (SGRN) consistent with this example are discussed below with respect to FIG. 9.

In FIG. 7A, the initial cell has divided to yield two virtual cells in the virtual environment. Following the division event depicted in FIG. 7A, signaling (e.g., as operated by a plurality of gene units, chemical-interaction rules, action rules, physical-interaction rules, etc.) between the two progeny cells can result in each of the virtual cells establishing a cell state (e.g., state of differentiation, etc.) different from the other virtual cell. For instance, a first cell can be configured to have a light-colored surface, and a second cell can be configured to have a dark-colored surface. Each of the light and dark colored cells can have properties that 1) allow the cell to retain its light or dark color, respectively, and/or 2) prevent the other cell from attaining its light or dark color, respectively. As such, this example illustrates one process used to simulate maintenance of cell identity and/or differentiation, as well as demonstrating how intercellular influences can influence a cell's identity.

FIG. 7B illustrates a second graphical image of the simulation output following a second division event. As shown in FIG. 7B the cell identity can be configured to be heritable and/or otherwise influenced by the parent cell. For example, the light-colored cell gave rise to two light-colored daughter cells, and the dark-colored cell gave rise to two dark-colored daughter cells. In further embodiments, virtual cells can be configured to revert to previous and change to a different cell state. For example simulated intercellular signaling pathways (e.g., as operated by a plurality of gene units, chemical-interaction rules, action rules, physical-interaction rules, etc.) can influence cells to alter a cell state. FIG. 7C illustrates this embodiment and shows that one of the light-colored cells has altered its cell state to become a black-colored cell, leaving only one remaining light-colored cell in the virtual cell cluster.

The above-discussed model for differentiation does not include a mechanism for maintaining a virtual stem cell following one or more cell division events. However, mechanisms and/or interaction pathways for abstracted (e.g., not detailed, etc.) virtual molecular interactions can be advantageous for investigative attempts to better appreciate the dynamics of such a precursor model.

Figure 9:
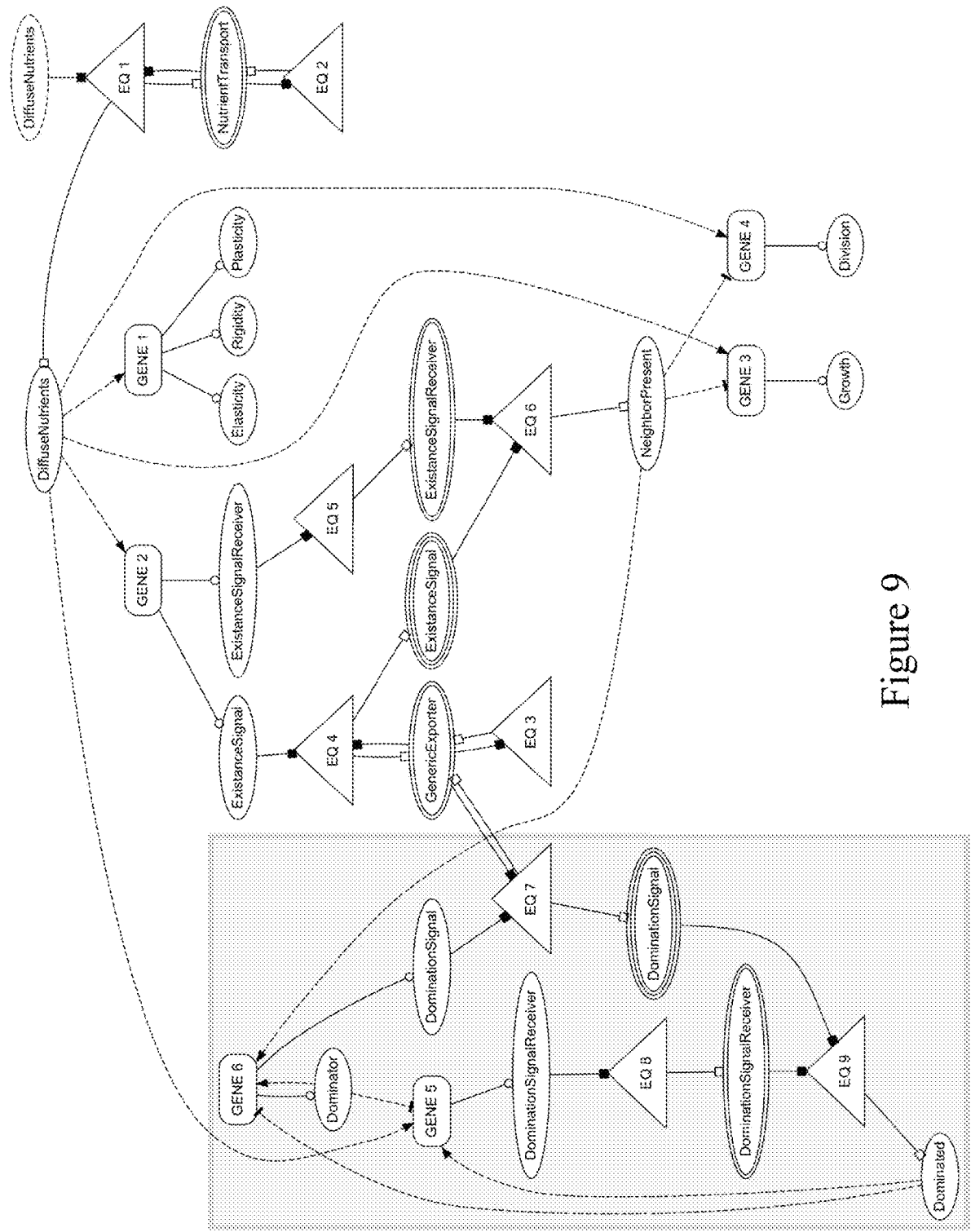
FIG. 9 is a schematic flow diagram illustrating a modeled SGRN for simulating development of a multicellular tissue in accordance with an embodiment of the disclosure.

FIG. 9 is a schematic flow diagram illustrating a modeled signaling and gene regulatory network (SGRN) for simulating development of a multicellular tissue in accordance with an embodiment of the disclosure. The SGRN illustrated in FIG. 9 some of the gene units, molecules, chemistry equations, etc., used for simulating the development of a multicellular tissue.

Figures 8A, 8B:
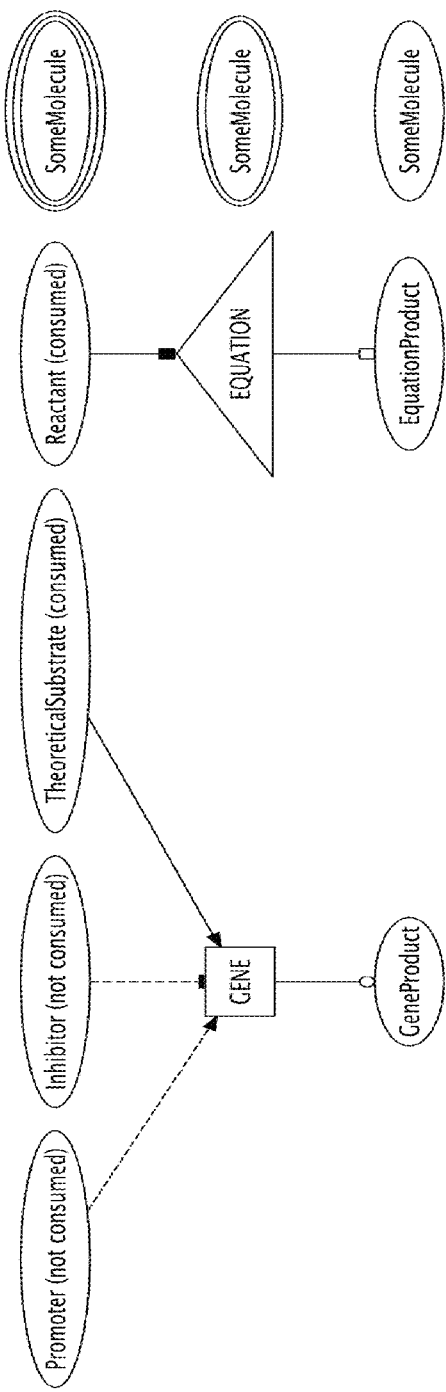
FIGS. 8A and 8B are schematic flow diagrams illustrating legends for interpreting flow diagrams describing molecules and actions in a modeled signaling and gene regulatory network (SGRN) in accordance with an embodiment of the disclosure.

FIGS. 8A and 8B are schematic flow diagrams illustrating legends for interpreting flow diagrams describing molecules and actions in a modeled signaling and gene regulatory network (SGRN) in accordance with an embodiment of the disclosure. As seen in FIG. 8A, a gene unit, represented by a square box in the SGRN diagram, can be acted upon by a variety of molecules, indicated by single-line ovals. A dashed line with an arrow indicates a promoter that is not consumed, a dashed line with a tee indicates an inhibitor that is not consumed, and a solid line with an arrow indicates a substrate that is consumed when an action is invoked (e.g., via a chemical-interaction rule, etc.). Also in FIG. 8A, the gene unit product is indicated by a solid line terminating at an open circle.

In a further example, the legend in FIG. 8B represents a chemistry equation. Reactants consumed by the chemistry equation are indicated by solid lines terminating in solid boxes. Products of the chemistry equation are indicated by solid lines ending in an unfilled box. FIG. 8B also shows three ovals representing molecules: those with a three-line perimeter represent extracellular molecules, those with a two-line perimeter represent molecules on a cell surface, and those with a single-line perimeter represent molecules internal to a cell.

With continued reference to the exemplary SGRN diagrammed in FIG. 9, extracellular DiffuseNutrients can be available in the virtual environment (e.g., indicated in the top right of FIG. 9) from a molecular source describe in the <Shade> section of the configuration file (described in more detail below). In this example, the shade configuration provides DiffuseNutrients in the extracellular environment. The molecular interaction equation "EQ 2" can be provided to move the NutrientTransport molecules (provided for in the initial configuration file) to a cell surface, where they can react in "EQ 1" with DiffuseNutrients for transporting the DiffuseNutrients into the cell.

Once inside the cell, DiffuseNutrients (indicated in FIG. 9 with a single perimeter) can invoke one or more changes in the molecule profile inside of the cell. For example, DiffuseNutrients can promote "GENE 1" to generate internal adhesion factors, such as RIGIDITY, PLASTICITY and ELASTICITY, to maintain a cell's cohesion. Likewise, DiffuseNutrients can also promote other gene units: "GENE 2", "GENE 3", "GENE 4", and "GENE 5", for example.

Shown in the lower central portion of FIG. 9, surface GenericExporter molecules, continually replenished by "EQ 3", can be a reactant in "EQ 4" with the ExistanceSignal, expressed by "GENE 2", to move the ExistanceSignal outside the cell. For example, GenericExporter can serve as a catalyst for transport of the ExistanceSignal molecule such that the ExistanceSignal molecule can function as a signaling molecule to neighboring cells (e.g., via "EQ 6").

The preceding description discusses configurable simulation information including cell metabolism information for simulating biological events such as growth, division, cell signaling, etc. The top, left shaded portion of the SGRN diagram in FIG. 9 included examples of configurable simulation information including information pertaining to cell differentiation. For example, this portion of the SGRN diagram illustrated in FIG. 9, represents a plurality of signaling events that can occur between virtual cells, including signaling events that promote development of, commitment to and/or maintenance of a cell state. For example, the presence of a neighbor cell, determined through "EQ 6", can promote "GENE 6" to generate both Dominator and DominationSignal molecules. Dominator molecules can be configured to both amplify the promotion of "GENE 6" (and create a self-reinforcing signal loop), while also be configured to inhibit "GENE 5".

With the presence of surface GenericExporter, "EQ 7" can move the DominationSignal expressed by "GENE 6" outside the cell. For cells receiving external DominationSignal, "EQ 9" can generate internal Dominated molecules. These Dominated molecules can be configured to both inhibit "GENE 6" and promote "GENE 5". In one embodiment, "GENE 5" can also be promoted by DiffuseNutrients. If not sufficiently inhibited by Dominator molecule, "GENE 5" can be configured to generate DominationSignalReceiver which, by "EQ 8", can be moved to the cell surface, interacting in "EQ 9" to receive DominationSignal from other cells.

Accordingly, the SGRN can be configured such that the more a given cell generates Dominator molecules, the more that cell can influence other cells in the virtual environment via DominationSignal. In contrast, the more DominationSignal a cell receives, the higher the level of Dominated molecules it will accumulate, thereby inhibiting its own production of Dominator molecules. In one embodiment, a first cell can progressively send more DominationSignal to a second cell. In such a scenario, the cells can commit to opposing states, thus having separate propensities to differentiate and to maintain these differences.

Daughter cells arising as a result of a cell division event from a parent cell having high DominationSignal levels can be initiated with some accumulated level of Dominator and DominatorSignal molecules, and accordingly, remain predisposed to generating high levels of DominationSignal molecules. Likewise, daughter cells arising as a result of a cell division event from a parent cell having high Dominated molecule levels can be predisposed to generate high levels of Dominated molecules. Additionally, following a cell division event, each daughter cell can be subjected to DominatorSignal versus Dominated molecule competition until only once cell remains having a high level of Dominated molecules. The resulting cell with high levels of Dominated molecules can be configured to resist differentiation and/or further differentiation to other cell states or cell types. In this example, the neighboring cells in the virtual environment can proceed to differentiate if so stimulated.

The cell-centric simulator can be configured to create and initiate virtual cells having a variety of and/or different virtual genomes. However, GENE UNITS 1 through 6 listed above in Table 1 are representative of gene units that can be included in virtual genomes regardless of the model being queried. Similarly, chemistry equations 1 through 9 listed above in Table 2 can be representative of a "standard set" of chemistry interactions associated with cellular transport, decay or renewal of molecules, and molecular interactions. Examples 1 through 5 described below illustrate different virtual tissue systems involving different and configurable virtual genomes and chemistry equations. The SGRN illustrated in FIG. 9 shows the interactions of gene units and chemical-interaction rules relating to Example 1 (described below) for a simple tissue model having cells committed to differentiation.

D. Physical Constraints

Physical constraints on the virtual cell and/or environment can be configured. This section discusses the representation of virtual cells, as fixed spheres, free-space solid spheres or free-space groups of subspheres. The following discussion also addresses embodiments of the disclosure relating to calculation of adhesion forces applied between and among cells (e.g., spheres, groups of subspheres, etc.), and where cells are composed of multiple subspheres, between and among the intracellular subspheres.

D1. Grid Arrangement of Cells

Figure 10:
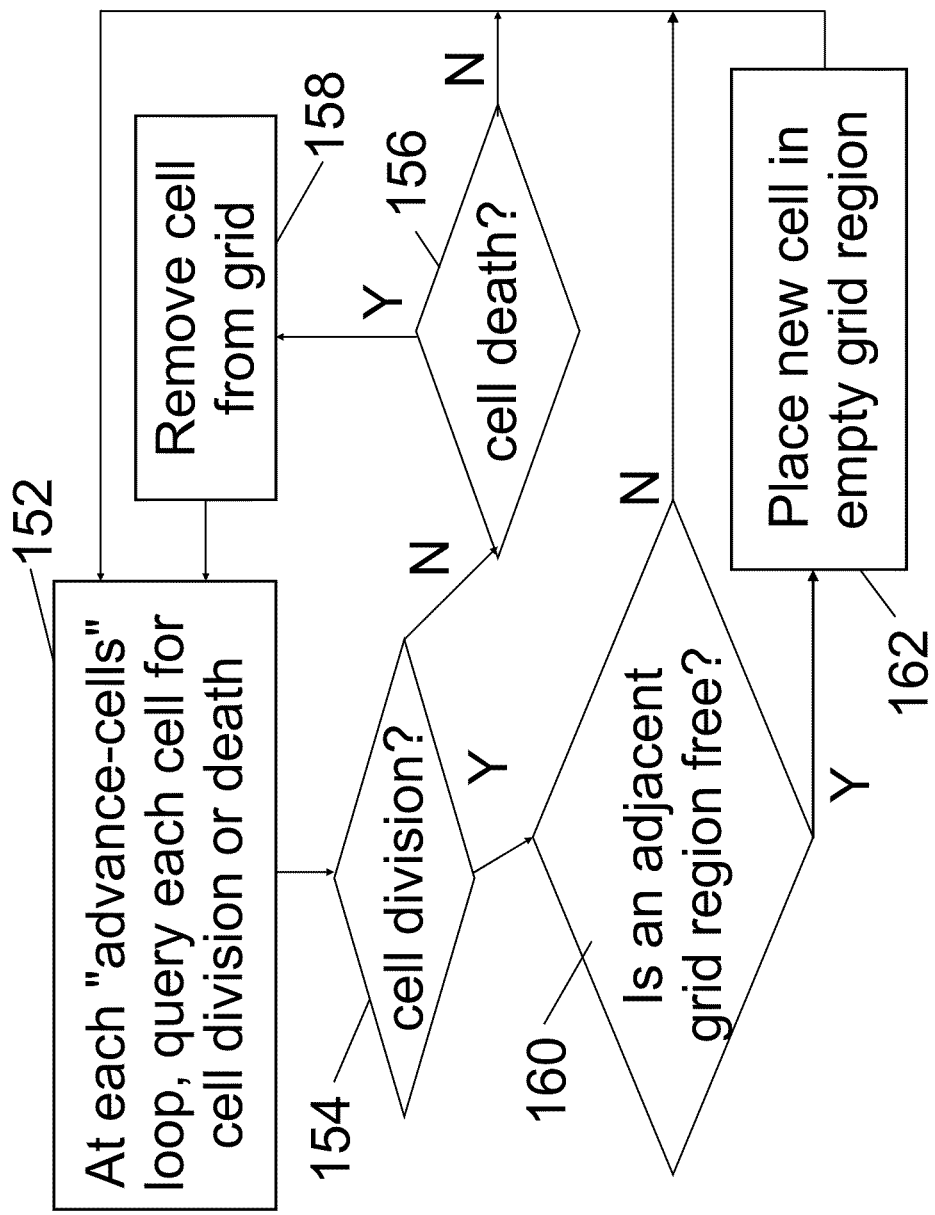
FIG. 10 is a flow diagram illustrating a routine invoked by a stepPhysics module using an egg-carton model for cell placement in accordance with an embodiment of the disclosure.
Figure 11B:
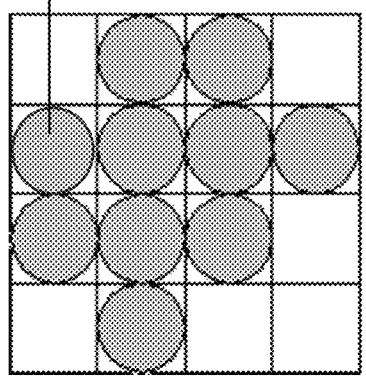
FIGS. 11A-11C are schematic block diagrams illustrating an embodiment of a planar egg-carton model for cell placement (11A), and illustrating virtual cell placement configurations after addition of a new virtual cell (11B), and after removal of one virtual cell (11C) in accordance with further embodiments of the disclosure.
Figure 11C:
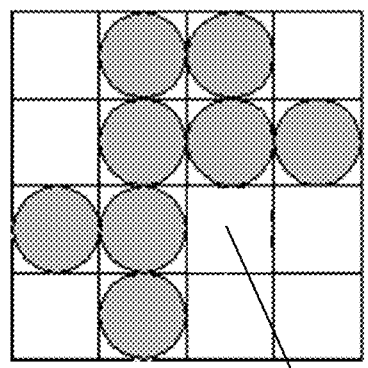
Figure 11A:
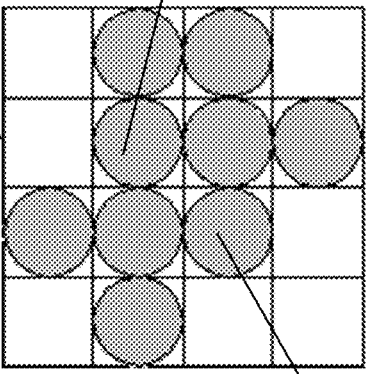

In one embodiment, modeling of virtual phenotypes by the ontogeny engine can be performed using a discrete-based environment space organized as a three-dimensional, uniformly divided grid, called "grid space". In this embodiment, uniform spherical shapes represent the cells, with one such spherical cell positionable at each individual grid location. Therefore, adjacent cells are positioned a predetermined and fixed distance from a given cell and can only be in any of the 26 adjacent locations. FIG. 10 is a flow diagram illustrating a routine invoked by a stepPhysics module using an egg-carton model (e.g., grid space model) for cell placement in accordance with an embodiment of the disclosure. FIGS. 11A-11C are schematic block diagrams illustrating an embodiment of a planar egg-carton model for cell placement (11A), and illustrating virtual cell placement configurations after addition of a new virtual cell (11B), and after removal of one virtual cell (11C) in accordance with further embodiments of the disclosure.

Referring to FIG. 10, the illustrated steps are part of the "stepPhysics" function shown at 46 in FIG. 3B, and as part of each "advance-cells" loop, shown at 36 in FIG. 3B and, more specifically for this representation, at 152 in FIG. 10. As seen in FIG. 10, the routine queries each cell during an "advance-cells" loop 152 for a cell-division or cell-death event. If the routine determines that a cell-division event has occurred during the loop (at decision block 154), the routine can further determine (at decision block 160) if an adjacent grid location is empty. If an adjacent location is available, a new cell is placed in that previously empty location (block 162).

For example, with the configuration of cells in the 4×4 grid shown at 164 in FIG. 11A, assume that the cell marked 166 is to divide. The location identified at 170 in FIG. 11B is identified as an empty, adjacent location which can accommodate a new cell from the division. As all cells in this approach are of uniform size and in fixed locations, daughter cells can be configured to be immediately equal in size and mass as parent cells. Referring again to FIG. 10, if there is no empty adjacent location available, the routine takes no action, and returns to the "advance-cells" loop (block 152). Referring to FIGS. 10 and 11A-C together, if the cell 168 in FIG. 11A is marked for death, the routine can remove that cell from the grid, as indicated at decision block 156 in FIG. 10 and at grid space 171 in FIG. 11C.

The grid space cell placement model provides cell-centric simulation without imposing increased complexity of a more realistic environment space. Cellular division, cell signaling, and phenotype evolution events can result from simplified calculations such as space available for division or discovery of cellular neighbors. If modeling some types of behavior or development wherein it is desirable to model a cell that is smaller than the fixed grid location volume, the modeled cell may not be in contact with other cells as it might in a more flexible (e.g., free-space) model. Since cell size varies in vivo, a living cell may have more than eight smaller adjacent cells or fewer than eight larger neighbors when considered in two dimensions (26 neighbor cells when considered in three dimensions): Such configurations may not be possible with the above described grid space cell position approach.

It is also feasible to consider other discrete space variations than the grid space description above. Grid locations can be made more granular allowing an individual cell to cover multiple locations but with each location allocated to at most one cell, or the shape of the grid organization can be changed from cubical locations to allow greater sphere packing and so potentially vary adjacency. Further, non-spherical shapes can exhibit different patterns of adjacency than are possible with simple spheres.

D2. Free Arrangement of Cells

In another embodiment, the cell-centric simulator can be configured to model cell position using a "free space" approach. In the free space modeling approach, cell positions are not constrained to a fixed grid using discrete coordinates, but can be specified in actual coordinates. Furthermore, the free space model allows for cell movement throughout a defined and/or constrained space or area.

For free space modeling, the following are considered: (i) locating vacant, adjacent positions where a cell division event can place daughter cells; (ii) detecting cell boundaries so that cell bodies do not simultaneously occupy the same space; (iii) moving cells within free space, (iv) adhering cells to one another so that some cells are considered attached; (v) locating neighboring cells for exchange of cell signals; and (vi) shaping cells, in embodiments wherein free space modeling is configured to allow non-spherical cell shapes.

In living biological cells, the process of cytokinesis results in two daughter cells having a joint mass approximately equal to the mass of the parent cell. If division is symmetric, each daughter cell is approximately half the size of the parent and the two new cells occupy roughly the same space as the original cell (Alberts, B., A. Johnson, J. Lewis, M. Raff, K. Roberts, and P. Walter (2002). *Molecular Biology of the Cell*, Fourth Edition, pp 1027-1125. Garland Science, New York. [Alberts 2002]). Since the division halves the mass into two new cells, these cells must subsequently grow to reach the size of their parent cell.

By dividing virtual cells in the same way as living cells, cell placement can be realistically achieved in free space. Further, cell division and growth can be configured as separate cell actions. Most of the space for daughter cells is immediately available since it was occupied by the pre-division parent cell. To resolve adjacency, cells can be placed such that an adjoining point between the daughter cells is at a coordinate approximately equal to the parent cell's center point prior to the division event.

Though partially solving adjacency and vacancy, it is the cell mass, and thus its volume, that is halved (assuming constant density). A spherical cell's radius is not likewise halved. Since the volume of a uniform sphere is $$V = \frac{4}{3}\pi R^3$$

where V is the volume and R is the radius, the radius of the new sphere is $$r = \sqrt[3]{\frac{1}{2}}\, R \approx 0.79R$$

which is quite larger than $$\frac{1}{2}R.$$

A free space model with realistic cell division must either accept that new cells overlap by more than 25% of their radii and so simultaneously occupy the same space or they must push away from one another (possibly pushing on other adjacent cells) to resolve this overlap.

Figure 12:
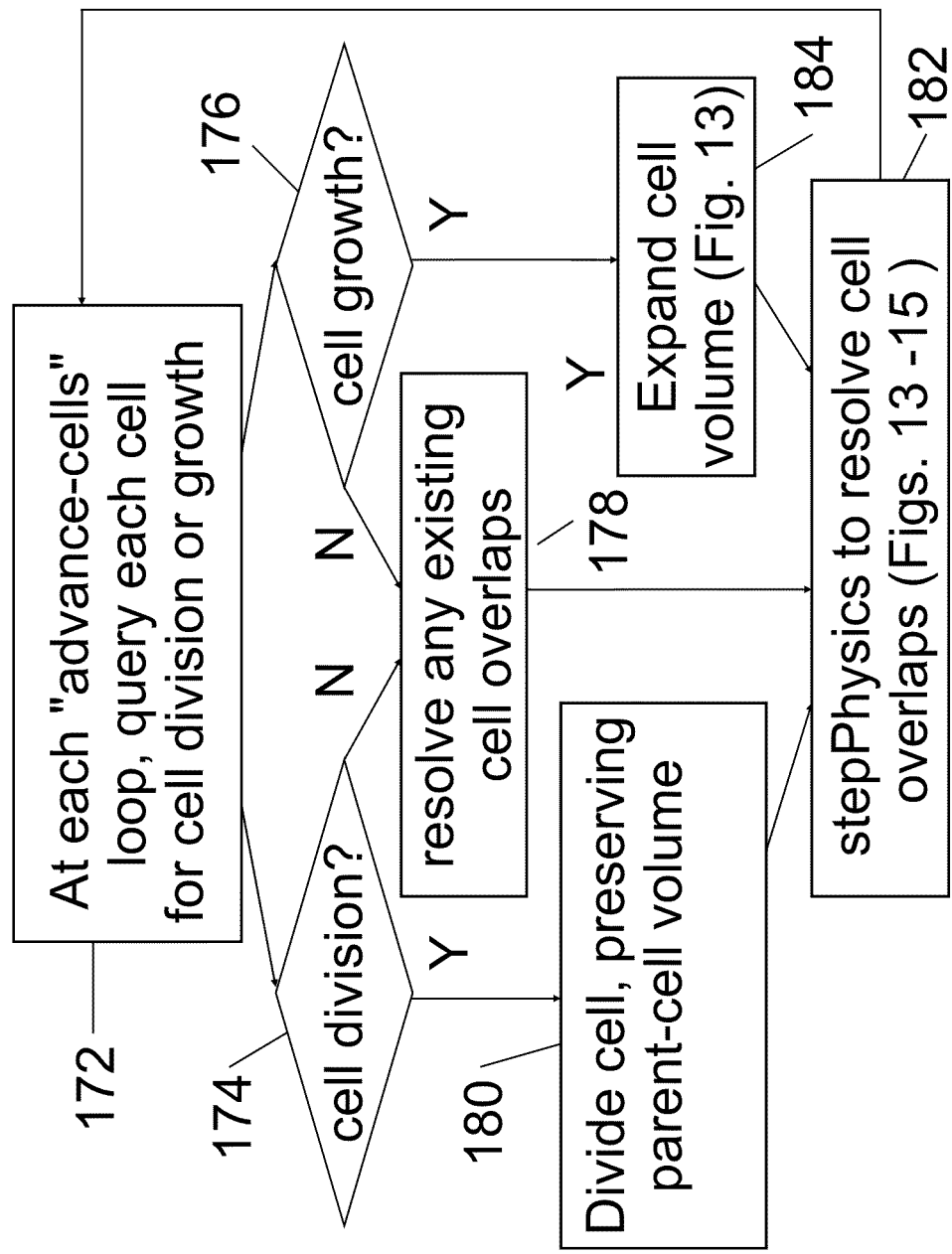
FIG. 12 is a flow diagram illustrating a routine invoked by a stepPhysics module using a free-space model for cell placement in accordance with an embodiment of the disclosure.

FIG. 12 is a flow diagram illustrating a routine invoked by a stepPhysics module using a free-space model for cell placement in accordance with an embodiment of the disclosure. Referring to FIG. 12, the illustrated steps are part of the "stepPhysics" function shown at 46 in FIG. 3B, and as part of each "advance-cells" loop, shown at 36 in FIG. 3B and, more specifically for this representation, at 172 in FIG. 12. As seen in FIG. 12, the routine determines, for each cell during an "advance-cells" loop 172, if a cell-division event (decision block 174) or cell-growth event (decision block 176) will occur. If a cell-division event is indicated at block 174, the routine includes dividing the cell while preserving the parent cell volume (block 180). In one embodiment, the cell-division event can include dividing a parent cell into two daughter cells having approximately equal volume. Following cell division at block 180, the routine can invoke a stepPhysics function to resolve cell overlaps (block 182). Following resolution of cell overlap at block 182, the routine can return to block 172.

If a cell-growth event is indicated at block 176, the routine includes expanding the cell volume (block 184). Following cell growth and/or expansion at block 184, the routine can invoke a stepPhysics function to resolve cell overlaps (block 182). Following resolution of cell overlap at block 182, the routine can return to block 172. If a cell-division and/or a cell-growth event does not occur (as determined at blocks 174 and 176, respectively), the routine can resolve existing cell overlaps (block 178) by invoking a stepPhysics function at block 182.

FIGS. 13A-13C are schematic block diagrams illustrating modeled cell division and cell growth events using a solid sphere free space model in accordance with an embodiment of the disclosure. As illustrated in FIGS. 13A-13C, a cell division event giving rise to two cells of equal volume, but with radii that are substantially greater than half of the parent cell's radius, results in cell overlap (FIG. 13B). As the daughter cells grow (FIG. 13C), there is progressively greater cell overlap that must be accommodated by movement of the cells away from one another.

FIGS. 14A-14C are schematic block diagrams illustrating modeled cell growth and cell spatial resolution events for a plurality of virtual cells using a solid sphere free space model in accordance with an embodiment of the disclosure. For example, FIG. 14A illustrates a cluster of cells that have not been positioned to accommodate cell growth. As the cells grow, there is increasing overlap among adjacent cells (FIG. 14B), exerting mutual repulsion forces on each pair of overlapping cells. FIG. 14C illustrates how these repulsion forces are resolved by movement of the cells in the direction of the indicated arrows.

Figure 15:
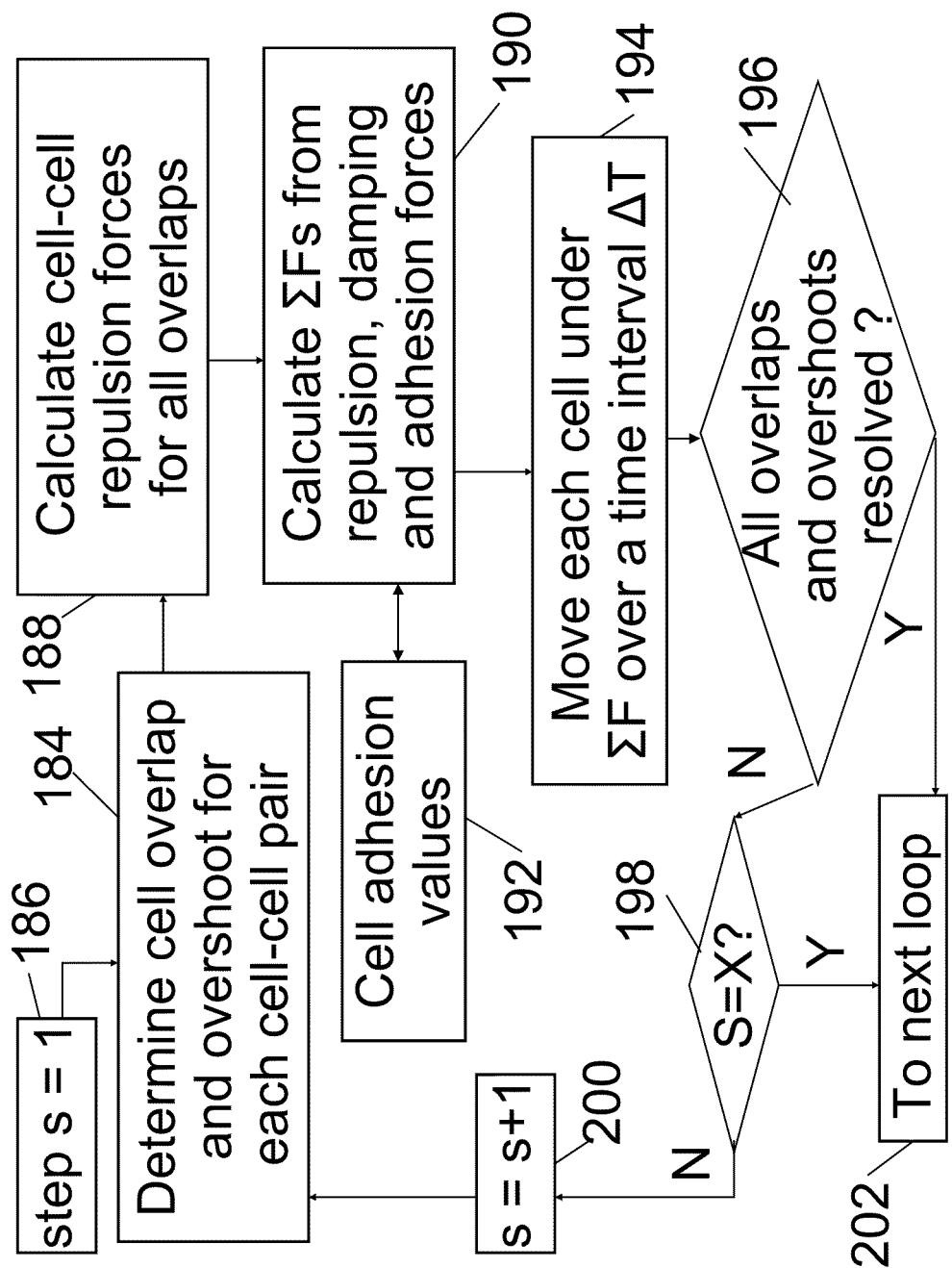
FIG. 15 is a flow diagram illustrating a routine invoked by a stepPhysics module for resolving cell overlap and overshoot events for a plurality virtual cells using a solid sphere free-space model in accordance with an embodiment of the disclosure.

FIG. 15 is a flow diagram illustrating a routine invoked by a stepPhysics module for resolving cell overlap and overshoot events for a plurality virtual cells using a solid sphere free space model in accordance with an embodiment of the disclosure. As described below, these steps can be part of a single "successive loop" operation of the system (e.g., "advance-cells" loop shown at 36 in FIG. 3B). In a particular example, in each cycle of this loop, the stepPhysics function can be configured to carry out a predetermined number of cell position adjustments designed to reduce the extent of overlap or overshoot, such that changes in volume and position from division, growth, or death preserve overall cell shape and intercellular contact.

In the first stage, and with the step number set to 1 at block 186, the routine can determine the extent of cell overlap or overshoot for each pair of cells in the virtual environment (block 184), and calculate intercellular repulsion forces for cell-pair overlaps (block 188). Using cell adhesion values (block 192), the routine can compute forces acting on each cell (block 190). In one embodiment, the computed forces can include repulsion forces, damping forces or adhesion forces, etc. Each cell can be moved under the calculated forces over a given time interval, ΔT (block 194). After the position adjustment at block 194, the routine can evaluate, at decision block 196, whether the cell movement at block 194 was effective to resolve overlaps and overshoots. If not, the steps described above can be repeated, through the logic illustrated at blocks 198 and 200. The process can be reiterated until all of the overlaps and overshoots are resolved, as indicated at 196 and 202, or until a given number of iterations (e.g., 20, 50, 100, etc.) has been performed, as indicated at 198 and 202. Individual aspects of the routine and its logic are detailed below.

D3. Cell Movement in Free Space

Exemplary forms of cell motion or movement available to natural living cells are listed in Table 3 below.

TABLE 3

Categorical Examples and Descriptions of Cell Movement

| | |
|---|---|
| TRANSLOCATION | Passive displacement where the cell is moved across space by forces external to the cell; also called translation. |
| LOCOMOTION | Active displacement when the cell moves itself or travels across space. |
| RESHAPING | Modification of the cell shape, regardless of whether it remains in place. |

Regardless of its cause, cell overlap may be resolved by considering an opposing cell to apply an external force on the subject cell such that the subject cell is translocated. Cell translocation may also occur due to forces applied outside the phenotype. For instance, pressure from a blunt instrument such as a probe may push on cells and so motion is one effect on a cell from an external force. From a cell's frame of reference, a force from an external probe or from another cell can result in translocation.

In one embodiment, computational support of cell translocation can be included in free space cell position modeling. As the ontogeny engine advances from a current step boundary to a next step boundary, a plurality of operations is applied to the virtual cells and environment. Accordingly, cell movement can also be "advanced" from a current step boundary to a next step boundary.

In a particular example of cell movement in a virtual environment, cell A can travel a path. If a boundary for cell A overlaps with the boundary of another cell B along the travel path, the path of cell A can be altered and/or cell B can be displaced. When using discrete time steps (such as advancing from a current step boundary to a next step boundary), movement of cell A might be seen as a series of jumps. For example, a collision between cells A and B will only be noticed as long as jumps end where cells A and B overlap. One solution is to graduate the time steps such that the smallest possible translocation that might precede a collision can be taken and make the effect of the current boundary to next boundary step proportionate in relation to other cells' processes (e.g., transcription). In the one embodiment, a fixed number of movements, say 20 (indicated as X at 198 in FIG. 15), can be applied for one or more steps during a simulation session. For example, the fixed number of movements can be user-specified and/or empirically determined.

In some embodiments, cell translocation can also affect a phenotype when external forces are applied. For example, possible affects can include rotation, deformation, displacement of a cellular mass, separation of cells, etc. Accordingly, the motion of a cell and the forces upon a cell can be transmitted to other cells according to the structure of the phenotype.

D4. Cell Adhesion Through Connections

The transmission of force between cells is not applicable in the grid space model since those cells did not move from one grid location to another. However, in most living tissues [Alberts, 2002], cells are connected to each other in a network of physical attachments. These connections can determine how cells transmit force to other cells. From the cell translocation example above, if cell A moves, another cell might be pushed because of boundary collisions. Further, if cell A moves, a connected cell B may be dragged along to stay in contact with cell A.

Figure 16B:
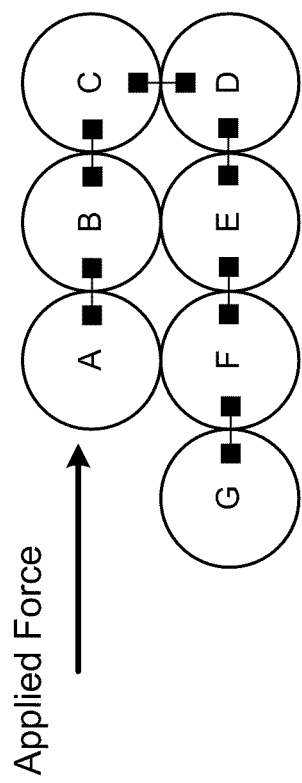
FIGS. 16A-16D are schematic block diagrams illustrating modeled distribution of forces among solid-spheres upon application of force to one of a group of connected solid-spheres, in the absence (16A and 16B) and presence (16C and 16D) of end-to-end sphere connections in accordance with en embodiment of the disclosure.

The concept of cell adhesion can be applicable when considering the transmission of force between some cells while not applying it to others. FIGS. 16A-16D are schematic block diagrams illustrating modeled distribution of forces among solid-spheres upon application of force to one of a group of connected solid-spheres, in the absence (16A and 16B) and presence (16C and 16D) of end-to-end sphere connections in accordance with en embodiment of the disclosure. As illustrated in FIGS. 16A and 16B: if a string of cells, labeled A through G are connected, but the string of cells is bent such that A and G have immediate physical proximity but are not directly connected, then pushing A away from G will not directly affect G. Instead A would drag B along with it and B would drag C and so on. Eventually G might be dragged along, but only when affected by a force from cell F.

Figure 16D:
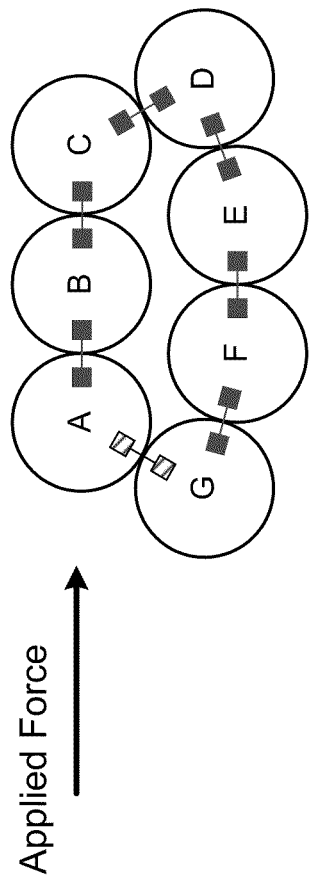
Figure 16A:
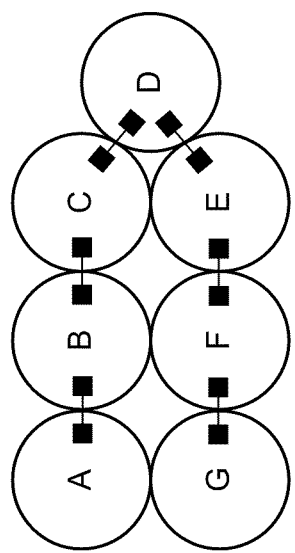
Figure 16C:
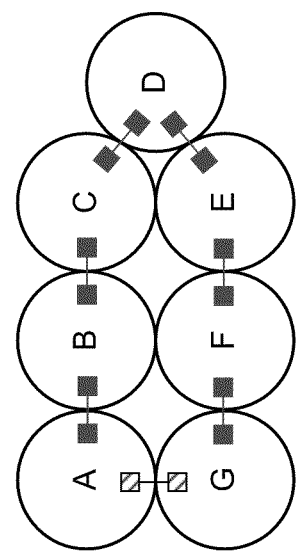

In a second scenario depicted in FIG. 16C and FIG. 16D, adding adhesion between A and G changes the respective cells' behavior as well as how the remaining cells are affected by an applied force. Adhesion connections can be configured to occur between multiple cells, for example, one cell can be independently connected to many cells. For example, Cell A can be directly connected to adjacent cells B and G, and so it may take more force to pull and/or push cell A since two other cells would also have to be moved.

Connected cells may also have other connections, increasing the resistance to translocate. In another example (not shown), pairs of cells may have multiple connections between them rather than just one large connection. This is analogous to some types of adhesion events seen in biology wherein cells attach themselves together with several connections [Alberts, 2002].

During and/or following cell division events, adhesion connections between cells can be resolved. In one embodiment, the proximity of the associated cell's surface to the surfaces of the new daughter cells can be determined. Following a cell-division event, the stepPhysics function can determine if the connecting neighboring cell is closer to the surface of one of the daughters than the other. The closest daughter cell can be assigned the already established adhesion connection. In some embodiments, the proximity of a connecting neighbor cell to each daughter cell can be approximately equal. In these embodiments, both daughters can be assigned an adhesion connection to the neighboring cell.

Adhesion connections can be configured to be rigid or flexible. If a connection is rigid and there is no inertia or other applied forces, pushing a cell also transfers that force to any adhered cells. Thus pushing a peripheral cell may cause a cluster of cells to rotate. Pushing a center cell of a cluster of cells may move the cluster of cells across a distance, but the cluster may otherwise remain unchanged. However, if the adhesion connection is flexible adhesion connection, then a cluster of cells having a first cluster shape may deform to a second cluster shape, with some of the cluster cells unaffected. Accordingly, it would take a greater force to affect cells further away from the point of contact.

D5. Generalizing Connections

In one embodiment, cell connections/adhesions can be modeled as a mathematical graph where the cells are represented by vertices and the connections represented by edges. In this manner, a cyclic undirected graph can be implemented, allowing operations upon cells using graph theory techniques such as shortest-path algorithms.

Other cell associations can be modeled as connections distinct from adhesion-type connections. In one embodiment, simulation of cell signaling events can be modeled as signals traveling along signal paths, thereby forming a signal connection. As in biological cell arrangements, signals can be transmitted to/from virtual cells that are not immediately physically adjacent to each other. To model such a relationship, a cyclic directed graph, distinct from a graph modeling adhesion connections, can be employed. For example, vertices on the graph can represent virtual cells, and edges can represent the applied signal connections.

In some embodiments, cell position can be calculated with reference to other cells, such as connected cells, or as an absolute position in the virtual environment. For example, a cell can be tracked during simulation with reference to the cell's absolute position in the general environment space. If the cell moves, its new location can be recalculated as a function of that translocation across the total space. In further embodiments, however, a cell position can be calculated with reference to other cells to which the cell is connected (e.g., in a multicellular tissue) and movement of the tissue and/or the cell can be integrated such that calculation of any individual cell position (e.g., following movement) can be in reference to that of that of the other cells (e.g., other cells in a multicellular tissue, other cells in a cell cluster, etc.). For example, the plurality of connections that can associate cells to other cells, can determine the relative position between the cells. For instance, if two cells are connected by a positional connection, the connection information generated during simulation can include information relating to a separation distance between the cells as well as a relative direction. In this way, cells can have a "position" relative to other cells. By treating one cell, in a group of cells, as anchored to an absolute position in the environment, absolute positions can be calculated for the remaining cells. Thus, if a single cell is moved such that a group of cells moves with it, the absolute anchor position can be recalculated, without requiring recalculation of the relative connections between the individual cells.

D6. Cell Signaling and Neighboring Cells

A cell in the ontogeny engine sends a signal by releasing virtual molecules to its neighbors. If the neighbor has receptors for the molecules it is presented with, it absorbs the signal and processes it. In grid space, such signals are simply applied within a specific radius from the cell's center: individual grid locations within this radius are readily calculated. In free space, a cell's neighbors cannot be determined with a simple check of enumerated adjoining spaces. Instead the same approach used for cell overlap resolution is applied: each cell in the phenotype is checked to see if it is a neighbor based on the distance of its surface from that of the other cell. If this separation of the two cells is within the configurable threshold, then they are neighbors and can share signals.

D7. Cell Shaping

To further improve fidelity with living cells, the ontogeny engine can support cell shaping. If two rigid, uniform spheres are positioned such that their shapes overlap, it is reasonable to treat this as a collision and resolve the overlap. However, most living cells do not have rigid shells, but have some plasticity and can deform. Further, through differentiation, cells adopt shapes that best fit the function they serve.

The various approaches to computing the shape of cells may be categorized as follows:

TABLE 4

Categorical Examples and Descriptions of Cell Shape

| | |
|---|---|
| EXTERNALLY SPECIFIED: | A cell's shape is a function for its surface such as a sphere or complex equation; shape is imposed upon the cell. |
| CALCULATED AD-HOC: | The cell has no prescribed shape, but rather is calculated when needed. An example might be the rendering of two cells close together: from an assumption of spheres, choose a midpoint between the centers of the cells against which to flatten the sides of the cells. |
| INTERNALLY DERIVED: | The cell's shape is maintained through internal data storage as a function of its own behavior. |

External specification of cell shape requires that known shapes be catalogued and defined rigorously. Such cataloguing inherently limits the range of cell shapes possible and removes the possibility that unconsidered or unrecognized cell shapes might better solve a phenotype development challenge.

Ad hoc shape calculation treats shape as completely dynamic, existing only as long as the influences on it continue. Cells then do not have their own shape but instead adopt whatever shape is most immediately useful. While some living cells may be very plastic, many cells (e.g., bone, skin) have a shape that, while deformable, are essentially static and continue for the duration of the cell's existence [Alberts, 2002].

Figure 17A:
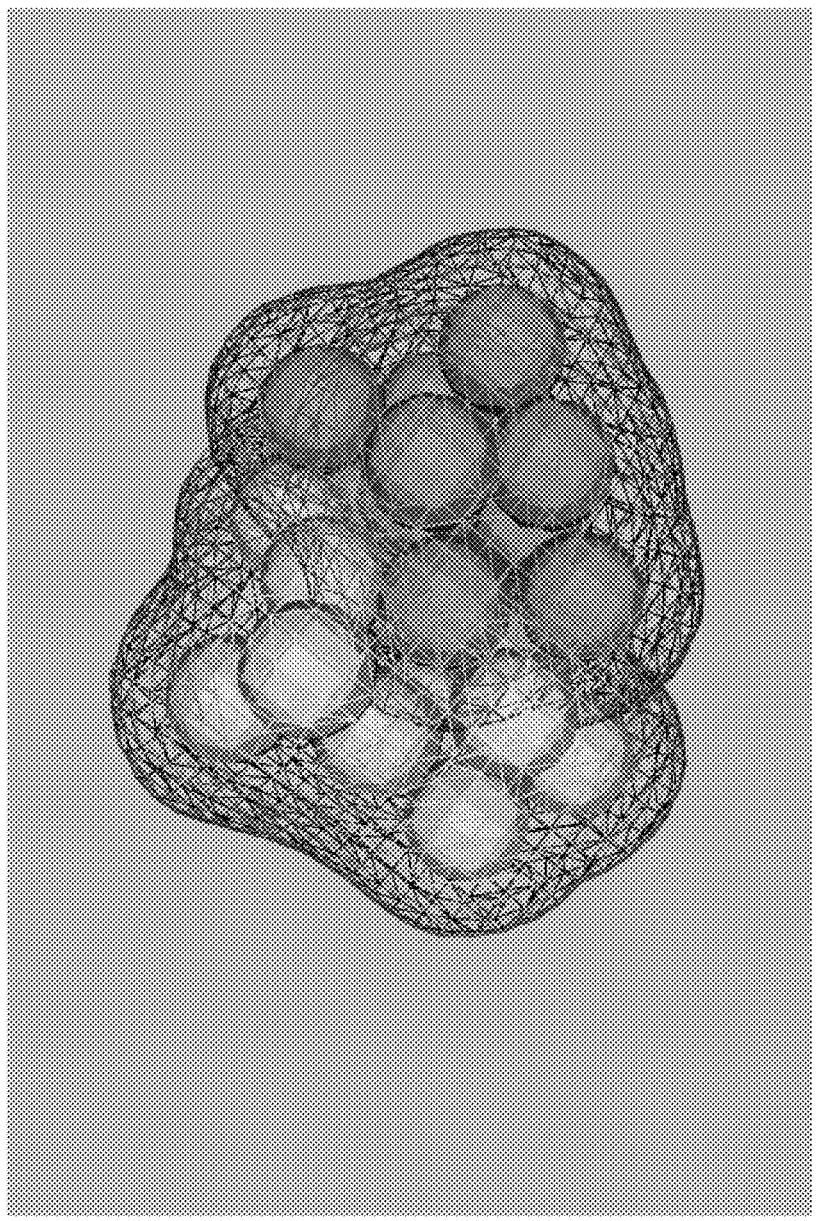
FIGS. 17A and 17B are isometric views illustrating two simulated cells using a subsphere free-space model with (17A) and without (17B) visible internal subspheres and in accordance with an embodiment of the disclosure.
Figure 17B:
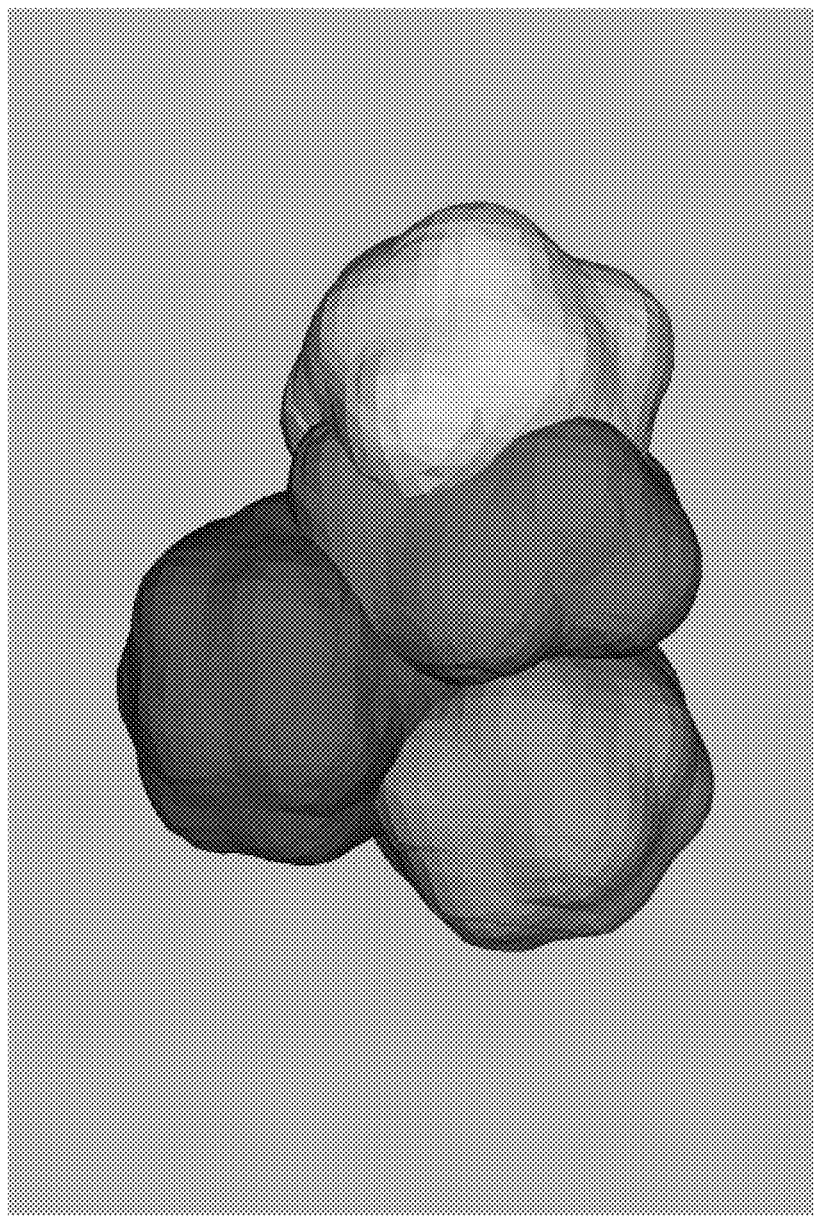

Internally derived shapes can provide fidelity with living cells. Cell shape can be modeled as collection of hard spheres held together with varying cohesion in the same way. FIGS. 17A and 17B are isometric views illustrating two simulated cells using a subsphere free-space model with (17A) and without (17B) visible internal subspheres and in accordance with an embodiment of the disclosure.

FIGS. 17A and 17B show such hard spheres depicted as "bags of marbles". FIG. 17A depicts the bags as wire-framed envelopes representing adjacent cells. The shapes of these cells are determined, as will be detailed below, by intracellular interactions among the marbles in each cell, and by extracellular interactions among marbles of adjacent cells. FIG. 17B depicts fully visualized bags without the internal marbles directly visible.

As an analogy, shifting a closed bag of marbles around moves the marbles around each other: the enclosing bag's shape is given from the arrangement of the enclosed marbles. Depending on forces imposed externally onto the bag (and thus the enclosed marbles) and how tight the bag holds the marbles together, the bag may become roughly spherical, fairly flat, or some arbitrary shape. For a pile of many such bags, each bag takes a form based on the surrounding bags and how each bag holds its marbles as cohesive collections. Forcing rigid connections between some of the marbles, such as with glue, constrains the potential shapes the bag can take.

This bag-of-marbles model is abstracted to remove the enclosing bag as a design construct, instead holding the marbles together in cohesive collections via virtual adhesions. The resulting shape of the marble collection is derived from whichever marbles are then exposed at the collection's surface. As before, forces applied to such collections cause the contained marbles to shift around until equilibrium is reached.

As in the previously described free space adhesion implementation, adhesions exist between sphere centers, but instead of uniform spheres representing whole cells, the spheres represent the proverbial marbles bound together to shape cells. These constituent spheres are referred to as subspheres. For each step of simulation, adhesions influence the arrangement of the subspheres.

Two methods of adhesion creations have been considered: completely-connected and proximity-based. When subspheres in a cell are completely connected, cell shapes tend to be spherical and highly coherent. When adhesions are created only between subspheres within a proximity threshold, cell shapes are frequently irregular and less coherent. Each of a cell's subspheres must be connected to at least one other intracellular subsphere, unless the cell is made up of only one subsphere.

Unlike adhesions between cells, these intracellular adhesions are not intended to faithfully model physical forces and constraints but more as a design mechanism from which to derive cell shape.

Again as described above in D5, the bag-of-marbles approach may be further abstracted as a graph with subsphere centers as vertices and center-to-center bonds as edges.

Biologically, cell size can be constrained by the physical characteristics of the cell membrane and other necessary structures. In the bag-of-marbles model, the minimum cell size is that of a single subsphere. For multi-subsphere cells, a single subsphere determines minimum cell thickness. Single-subsphere cells grow to multi-subsphere cells by the addition of subspheres. The cell's mass is taken as the sum of the contained spheres' given mass. In general, the cell size can be controlled by the number of subspheres and by the size of those spheres: many smaller spheres allow more resolution of shape while fewer, larger spheres reduce computational cost and range of shape variety. The preferred embodiment keeps subsphere size uniform across all cells, but this is not necessary, although calculations will be eased if all of a given cell's subspheres are of uniform size with or without regard to those of other cells.

All collisions of subspheres, whether within or between cells, are simply between the involved spheres and so are handled identically. The effect on the shape of the cell is derived then from the resulting arrangements. This approach simplifies the simulation.

Figure 18:
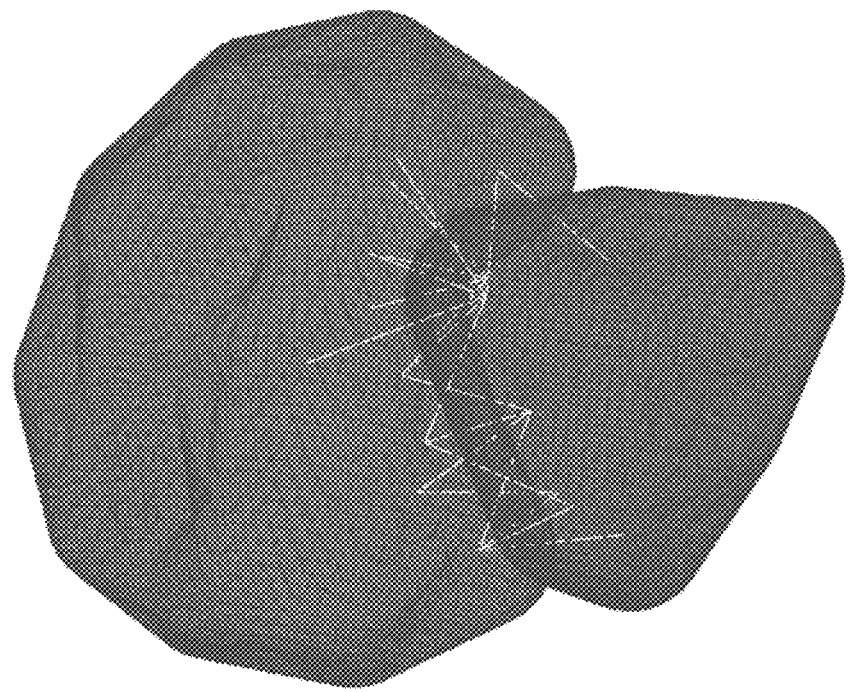
FIG. 18 is an isometric view illustrating two simulated cells behaving in accordance to simulated forces determined by intercellular adhesion rules and in accordance with an embodiment of the disclosure.

Although intracellular adhesions need not be faithful to real physical behavior for realistic modeling, fidelity is required with regard to adhesion between cells. Therefore, intercellular adhesions follow separate, though similar, logic than adhesions within cells. Nonetheless, intercellular adhesions are still anchored to cell subspheres. Cells pressed together are thus capable of forming many adhesions, creating an adhesion "contact patch", depending on how many of their contained spheres come into contact. FIG. 18 is a isometric view illustrating two simulated cells behaving in accordance to simulated forces determined by intercellular adhesion rules and in accordance with an embodiment of the disclosure. Such a contact patch is shown in FIG. 18 for two cells that are each shaped using the bag of marbles model, where the contact lines in the figure represent lines connecting the centers of each adjacent pair of spheres.

Figure 19:
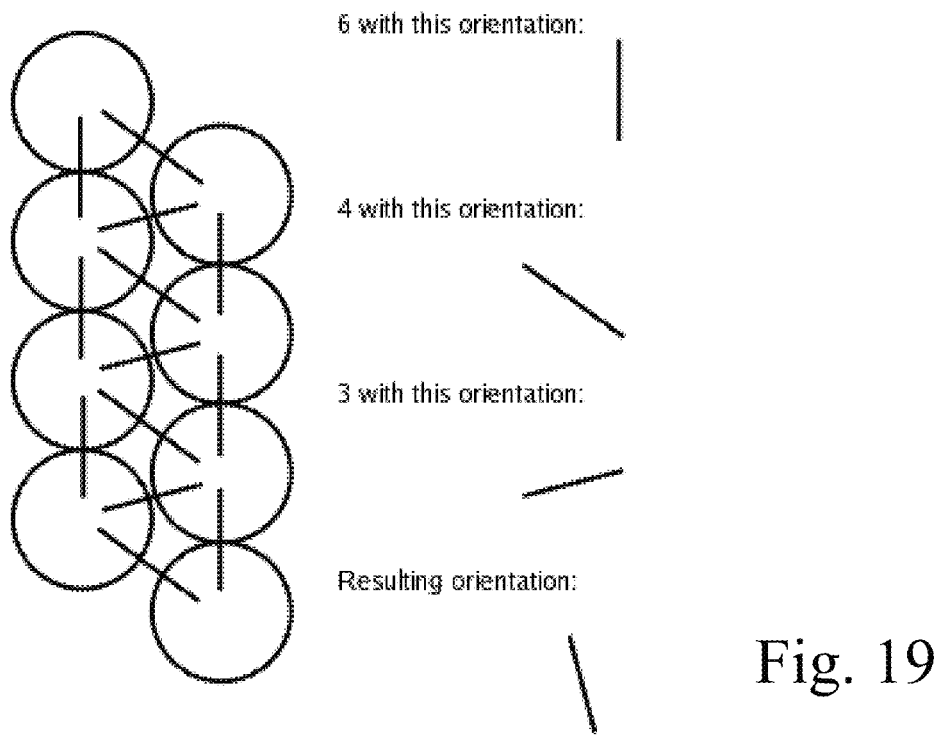
FIG. 19 is a schematic block diagram illustrating one embodiment for calculating the sum vector force of subsphere placement within a virtual cell for determining a modeled cell's resultant spatial orientation in accordance with an embodiment of the disclosure.

Similarly, lines connecting subcells can help determine cell orientation. FIG. 19 is a schematic block diagram illustrating one embodiment for calculating the sum vector force of subsphere placement within a virtual cell for determining a modeled cell's resultant spatial orientation in accordance with an embodiment of the disclosure. As illustrated in FIG. 19, the right side of the figure summarizes the orientations of these connecting lines. From this summary, the cell's overall spatial orientation can be evaluated for later application, analysis or reporting, such as determining a direction for cell division.

Without an internally maintained skeleton, there is no need for cells to have a separate coordinate system from that of the overall simulation context (i.e., environment). Rotation and translation of cells are simple derivatives of the interactions between the subspheres. A cell's orientation need only be calculated for specific actions such as cell division.

When a cell is to divide, its center of mass is determined. A partitioning plane is chosen to intersect the center of mass with a random orientation. Based on their relation to the dividing plane, the parent cell's subspheres are then allocated to the daughter cells. Any existing intracellular adhesions that cross the dividing plane are removed. Therefore, if division is to take place, the cell must have at least two subspheres.

Until visualization, the only constructs are the subspheres and their associating bonds: simulation of ontogeny involving cell shape is complete with only these elements. However, this is not satisfactory for visualization. To represent cells visually, an envelope is rendered around each cell's collection of subspheres. Thus, this expensive computation for the rendering of an arbitrary shape is deferred until necessary. Using various calculations for this visual envelope, cells may be made to appear more lumpy or smooth as aesthetics warrant.

An embodiment including a bag of marbles approach can support the following refinements:

- Differences in intracellular adhesions can indicate cellular differentiation as cells undergo continuing development.
- Cell energy levels can be integrated with intracellular adhesions: intracellular adhesions can lengthen or relax as cell energy increases. High-energy cells will be more malleable and become more rigid as they lose energy.
- Bond stability, the likelihood of two subspheres to continue to adhere, can be treated as a separate factor from energy and so independently control cell cohesion. The higher the cohesion, the more spherical it may tend to be. Stability and adhesion strength (or lengthening) will combine to determine cell rigidity. Further, a cell might be easily deformable (via lower adhesion strength) while retaining a shape memory (via stability) while another cell could resist deformation but readily accept the new shape when deformed.
- If subspheres are considered as having mass at uniform density, then the density at which the spheres are held to one another by adhesions allows for varying density of the overall cell.
- Cell orientation may be derived from the orientation of the vectors between all subspheres' centers (i.e., a fully connected graph of the marbles). Such orientation may be applied to influence the cell's plane of division. FIG. 19 depicts the determination of cell orientation from intracellular sphere relations.

E. CeliSim Configuration File

To illustrate how the virtual genes, chemistry equations, environmental parameters, and other settings are specified to the ontogeny engine, it can be useful to consider a configuration hierarchy. One of ordinary skill in the art will recognize additional embodiments for specifying parameters and settings to the ontogeny engine, and the examples described below are considered to be exemplary.

In one embodiment, configurations are written in XML. An XML file consists of nested pairs of bracketed tags. Each opening tag has a matching closing tag. A closing tag has the same name as the opening tag but the name is preceded by a forward slash ("/"):

```
<SomeTag>
    more nested tags or data
</SomeTag>
```

Tags without nested content can be opened and closed with separate tags or in a single tag:
<SomeTag/>.

Comments for the reader of the configuration file are ignored by the ontogeny engine. These are introduced with double forward slashes ("//"):

```
// The following tag indicates something interesting.
<SomeTag>
    more nested tags or data
</SomeTag>
```

Where periods of ellipsis (" . . . ") appear in the following description within opening and closing tags, subordinate tags may be nested. That is, the tags surrounding the ellipsis may contain subordinate tags, whose detail is not relevant to the immediate description but may be described elsewhere as appropriate.

Editing of the XML configuration file is conventionally done with an ASCII text editor as is commonly done for computer configuration files.

In the preferred embodiment, all configuration files have <CsIndividual> . . . </CsIndividual> as the root tag. The tags detailed below are subordinate to the <CsIndividual> tags.

E1. Development Engine

DevelopmentEngine options cue the server to watch for certain events and pause when they are reached. Each stopping condition is used only once. The user has the option to continue the simulation after a halting condition has been encountered. In the example below, the simulation will run until the earlier of 2000 simulation steps or until the phenotype has been stable for 1,000 steps.

```
<DevelopmentEngine>
    <MaxSteps>2000</MaxSteps>
    <StableSteps>1000</StableSteps>
</DevelopmentEngine>
```

E2. Molecular Catalogue

The MoleculeCatalog provides translations between named aliases and molecular signatures and properties. Each molecule has a name, a two-part signature, a decay rate, and an indivisible flag. The name is for ease of user reference during simulation or configuration; the signature is described in more detail below; and the decay rate describes a how quickly a molecule is reduced and removed from the simulation as a percentage (0.1=10% of the molecule per simulation step). If a molecule is indivisible, it cannot be divided between daughter cells during division, but must instead be allocated to only one of the two.

By default, the decay rate is set to an arbitrary value ("0.1" in the preferred embodiment for a 10% decay per step), and the indivisible flag is set to False. MoleculeA in the below example uses these defaults, so it only matches the alias 'MoleculeA' with its signature '[10, 10]'. MoleculeB specifies a decay rate of 0.2. MoleculeC does not decay and is indivisible: upon division, one daughter cell receives the entire amount of MoleculeC from the parent.

A molecular signature consists of an Indicant and a Sensitivity value. These values are used to calculate the Affinity between molecules and gene units. The Indicant is the molecule's interactive identity and the Sensitivity affects how much Affinity the molecule has for other molecules or gene units with different Indicants. An exact Indicant match between a molecule and gene unit yields a maximum Affinity of 1.0. As the difference between Indicants increases, Affinity decreases at a rate determined by the Sensitivity values of the molecule and gene unit. A molecule with a Sensitivity of 0.0 matches any gene unit; likewise, a gene unit with a Sensitivity of 0.0 matches any molecule. As Sensitivity increases, Indicants must match more closely for there to be significant interaction between molecules and gene units. Molecules A, B, and C below have very high Sensitivities (10) and call for a nearly exact Indicant match with a gene unit to have any effect. MoleculeD, however, with a low sensitivity of 0.5, could interact significantly with gene units having Indicants differing by as much as 5 from MoleculeD's Indicant.

```
<MoleculeCatalog>
  MoleculeA [10, 10];
  MoleculeB [20, 10] 0.2;
  MoleculeC [30, 10] 0.0 I;
  MoleculeD [40, 0.5];
</MoleculeCatalog>
```

E3. Simulation

The Simulation tag encloses parameters for simulation conditions, as described below in Subsections E.3.1 to E.3.7:

```
<Simulation>
...
</Simulation>
```

E3.1. Signal

The choice of Signal method and Signal settings determines how all signals originating in cells will be distributed between non-contacting cells. <FallOff> signaling allows signals to decrease in concentration in a smooth curve as distance increases. The meanings of settings for <FallOff> signaling are discussed under <Shade> below. <Local> signaling presents a fully concentrated signal across the specified separation distance, but none beyond. <Droplet> signaling diffuses signals through fluid droplets when fluid droplets are present in the simulation. <Linear> signaling decreases signal concentration linearly with distance.

```
<FallOff>
  <Exponent>0.5</Exponent>
  <Modifier>2.0</Modifier>
  <Radius>1.0</Radius>
  <Threshold>0.05</Threshold>
</FallOff>
```

```
<Local>
  <Separation>0.2</Separation>
</Local>
<Droplet>
  <Separation>0.1.25</Separation>
</Droplet>
<Linear>
  <Slope>2</Slope>
</Linear>
```

E3.2. MaxInterAdhesionLength

Adhesions between two cells break if they exceed the specified separation distance. The example below specifies a separation distance of 0.25. This parameter primarily accounts for small separations that potentially result from incomplete physics resolution rather than breaking of an adhesion. In general, cell flexibility via Rigidity determines when cell adhesions are broken.

<MaxInterAdhesionLength>0.25</MaxInterAdhesion-Length>

E3.3. SingleAdhesionRule

If the binary parameter <SingleAdhesionRule> is configured as 1, each sphere of a cell may adhere to only one sphere of one other cell, regardless of contact with other spheres of other cells. When it is configured as 0, the number of intercellular adhesions between spheres is limited only by physical contact constraints.

<SingleAdhesionRule>0</SingleAdhesionRule>

E3.4. The Physics Profile

The Physics profile encompassed within the opening and closing tags below, addresses those parameters related to the operation of stepPhysics, and includes sections E.3.4.1 to E.3.4.7

```
<Physics>
...
</Physics>
```

E3.4.1. RepulsionMultiplier

When any two objects in the simulation overlap, a force is applied to separate them. This multiplier adjusts how strong the repulsion force will be. More significant than the absolute value of the specified <RepulsionMultiplier> is the ratio between <RepulsionMultiplier> and <DampingMultiplier>. For example, 1:2 and 100:200 ratios will result in similar collision physics. In the example below, the multiplier is set to 1.

<RepulsionMultiplier>1</RepulsionMultiplier>

E3.4.2. DampingMultiplier

Any object has a resistance force applied opposite its direction of motion. This force is relative to the object's velocity rather than its mass or volume, so a lightweight object at a certain velocity will be slowed more rapidly than a heavier object at the same velocity. In the example, below, the multiplier is set to 2.

<DampingMultiplier>2</DampingMultiplier>

E3.4.3. TimePerStep

<TimePerStep> relates time for physics resolution to the simulated metabolism. Smaller values specify faster metabolism relative to simulated physics resolution, and conversely for larger values. The value specified is in seconds, but has no relation to real time. Thus the reciprocal of the value specified is the number of metabolic steps per second. In this example, there are two (=1.0/0.5) metabolic steps per physics second.
<TimePerStep>0.5</TimePerStep>

E3.4.4. MaxVelocityChange

All forces and collisions are attempted to be resolved within the simulation time allocated to each step in as few physics iterations as possible. To maintain smooth, realistic physics simulation, <MaxVelocityChange> specifies the largest velocity change (i.e., acceleration or deceleration) allowed per physics iteration before overlaps and other physics issues are rechecked. Small values improve physics fidelity at the expense of performance and conversely for large values.
<MaxVelocityChange>0.5</MaxVelocityChange>

E3.4.5. NudgeMagnitude

This parameter specifies the force applied when a user nudges a cell during a simulation run.
<NudgeMagnitude>3</NudgeMagnitude>

E3.4.6. Container

The growth of the phenotype can be physically constrained by specifying a container. A dish container places a virtual petri dish with the specified radius centered at the specified X, Y, Z coordinates. The dish container has infinitely high walls so the phenotype can never escape. In the example below, the "dish" is centered at coordinates 0, −3, 0 with a radius of 10.

```
<Container>
  <Dish>[0, -3, 0] 10</Dish>
</Container>
```

E3.4.7. Gravity

The simulation has no gravity by default. Simulated gravity is added with the <Gravity> tag. Its value adjusts the gravitational force applied throughout the environment.
<Gravity>0.2</Gravity>

E3.5. FixedSpheres

Fixed spheres are immovable, inert, uniform spheres placed in the environment as a physical constraint to phenotype development. Each fixed sphere is described with X, Y, and Z coordinates followed by a radius.

The example below describes two very large fixed spheres are placed above and below the center of the environment where the initial cell is placed. In effect, the cells are sandwiched between flat plates because the radius of these fixed spheres is much larger than the 0.5 radius of the cells.
<FixedSpheres>
  [0, −1000, 0] 1000,
  [0, 1001, 0] 1000
</FixedSpheres>

E3.6. Cell

The Cell tag encloses various virtual cell parameters, described below in E.3.6.1 to E.3.6.7:

```
<Cell>
...
</Cell>
```

E3.6.1. Chemistry

<Chemistry> determines how Affinity will be calculated between molecules and gene units. <Default/> chemistry specifies that Affinity will follow a normally distributed bell curve.
<Chemistry><Default/></Chemistry>

E3.6.2. Promoter

<Promoter> determines how Promotion will be calculated in gene unit transcription. Promotion is based on the Affinity of molecules for a regulatory gene unit and their concentrations.

One such <Promoter>, <Smoother> promotion, has a sigmoidal curve with 0.0 Promotion at 0.0 Affinity and Concentration, and approaches 1.0 Promotion as Affinity and Concentration increase.

```
<Promoter>
  <Smoother>
    <PromotionMidpoint>5</PromotionMidpoint>
    <Slope>3</Slope>
    <ActiveConcentration>1</ActiveConcentration>
  </Smoother>
</Promoter>
```

Figure 20:
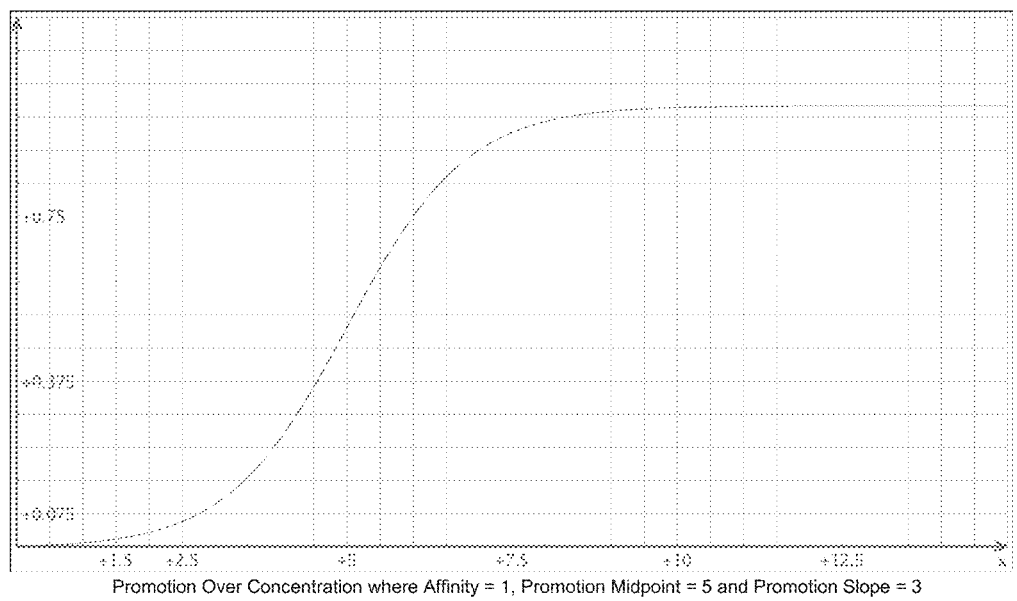
FIG. 20 is a graph illustrating a promotion curve for a modeled molecule interacting with a modeled regulatory gene wherein the affinity between the molecule and gene unit is equal to one in accordance with an embodiment of the disclosure.

FIG. 20 is a graph illustrating a promotion curve for a modeled molecule interacting with a modeled regulatory gene unit wherein the affinity between the molecule and gene unit is equal to one in accordance with an embodiment of the disclosure. FIG. 20 depicts the promotion curve for a perfect match between a single molecule interacting with a single regulatory gene unit. In this case, the Affinity between the molecule and gene unit is 1.0. The promotion of the gene unit given the current concentration of the molecule is multiplied by the gene unit's Effect value to compute the partial promotion of the gene unit by that molecule. Total promotion of the gene unit is the sum of such partial promotions from all molecules. Where a regulatory region contains multiple gene units, the promotion of the region is the sum of all constituent gene unit promotions.

Net positive promotion results in internal production of corresponding structural gene unit product equal to the net positive promotion. The volume of the cell determines how this amount affects concentration: smaller cells experience a greater increase in concentration through transcription than larger cells for the same gene unit promotion level.

From the example configuration above, the promotion curve in FIG. 20 has a midpoint of 5 and slope of 3. As a result, 50% promotion occurs at concentration 5 and ramps sharply from 25% to 75% between concentrations 4 and 7, with asymptotically approaching 100% at concentrations above 10. With consideration of the promotion curve, a researcher can develop intuition with practice from watching resulting molecular concentration levels to appreciate the influence any internal molecule is having on gene units.

E3.6.3. InitialSize

This option specifies the number of sub-spheres in the initial cell placed in the environment at the beginning of the simulation.
<InitialSize>13</InitialSize>

E3.6.4. MaximumSize

A cell may not grow to have more than the number of sub-spheres specified as the MaximumSize. The <InitialSize> may be specified as larger than <MaximumSize>: such a setting can result in zygote-like division.
<MaximumSize>13</MaximumSize>

E3.6.5. MinimumSize

A cell may not divide if one of the equally sized daughter cells would have fewer than the MinimumSize number of spheres. The <InitialSize> may be specified as smaller than <MinimumSize>.
<MinimumSize>6</MinimumSize>

E.3.6.6. InitialChemistry

By default, the initial cell in a simulation contains no molecules and so has no way to import molecules from the environment. <InitialChemistry> specifies the contents with which to initialize this cell. In the example below, the initial cell is primed with 80 units of Nutrient and 10 units of NutrientReceptor on its surface (as denoted by parentheses). The concentration of these molecules depends on the volume of the initial cell as specified by <InitialSize>.

```
<InitialChemistry>
  Nutrient 80
  ( NutrientReceptor ) 10
</InitialChemistry>
```

E3.6.7. Chemical-Interaction Rules

Chemical-interaction rules, designated as ChemistryEquations, are direct conversions of substrate molecules to produce molecules independent of gene unit transcription. The terms to the left of the equal side describe necessary reactants and must include at least one internal or surface molecule. The terms to the right of the equal side describe the products of the interaction. Any equation with external molecules as either reactants or products must have a surface molecule reactant. Refer to Section C for details on the role of chemical-interaction rules.

In the example below, the first equation specifies that internal NutrientReceptor is to be consumed to produce an equal amount of surface NutrientReceptor. The second equation specifies that external Nutrient is to be transported into the cell by surface NutrientReceptor. The surface NutrientReceptor is replaced on the product side and so acts as a catalyst in the equation. Coefficients can be specified for any reactants or products to describe proportion and amounts as demonstrated in the third example equation.

```
<ChemistryEquations>
  NutrientReceptor = ( NutrientReceptor );
  { Nutrient } + ( NutrientReceptor ) = Nutrient + ( NutrientReceptor );
  1.5 SubstrateA + 2 SubstrateB = SomeProduct;
</ChemistryEquations>
```

E3.6.8. DivisionRules

By default, cell divisions have random directional orientation. By specifying DivisionRules, division can occur in a direction relative to the highest activity of a surface molecule. Rule choice depends on the concentration of internal or surface molecules, as modified by a positive, multiplier coefficient; single division rules must specify a positive coefficient. Directional keywords are "perpendicular", "toward", "away", and "random". For DivisionRules, "toward" and "away" are equivalent. Alternatively, directions may be specified as angles in real degrees from 0 to 180.

```
<DivisionRules>
  0.5 Nutrient perpendicular ( ContactReceptor );
  1 NeighborhoodMarker toward ( NeighborhoodReceptor );
  1 ContactMarker random;
</DivisionRules>
```

E3.7. AdhesionRules

AdhesionRules are pairs of colon-separated surface molecules. When two cells contact one another, the list of adhesion rules and the molecules on the cells' surfaces are compared to determine if an adhesion is to be formed.

In the first example rule below, an adhesion is formed if each cell has CellAdhesion molecule on its surface. In the second example equation, one cell must have CellAdhesionA on its surface and the other cell must have CellAdhesionB. The strength of an adhesion depends on the concentrations of the adhering molecules.

```
<AdhesionRules>
  ( CellAdhesion ) : ( CellAdhesion );
  ( CellAdhesionA ) : ( CellAdhesionB );
</AdhesionRules>
```

E4. Genome

As discussed in Section D above, Genome consists of a bracketed, comma-separated set of gene units. A gene unit consists of a bracketed Regulatory Region and a bracketed Structural Region. A Regulatory Region consists of a comma-separated set of Regulatory gene units. Each Regulatory gene unit has a molecule alias or an Indicant-Sensitivity pair, called a signature, and an Effect multiplier value. A Structural Region consists of a comma-separated set of Structural gene units, each of which is a molecule alias or signature.

Regulatory gene units either promote, with positive Effect values, or inhibit, with negative Effect values, transcription of the structural region of the gene unit. In each metabolic step, all internal molecules in a cell are compared to all Regulatory gene units and the promotion of the gene unit, based on the Affinity and concentration of each molecule, is multiplied by the gene unit's Effect value. If the net promotion of a Regulatory Region is positive, the molecules listed in the Structural Region are produced in the cell at a quantity matching the net positive promotion. If the net promotion of the Regulatory Region is zero or negative, no molecules are produced.

```
<Genome>
[
    [ Nutrient 0.9 ]
    [ NutrientReceptor ],
    [ Nutrient 1.0, SomeInhibitor −1.0 ]
    [ ProductA, ProductB, SomeInhibitor ]
]
</Genome>
<Shade><UseRadius/><UseModifier/>
```

E5. Shade

Shade is a bracketed collection of comma-separated molecular point sources, sometimes called gradient builders. In practice with the preferred embodiment, <UseRadius/> and <UseModified> are specified to designate a more complete description of the point sources.

Each point source description begins with an "S", followed by a molecular alias or signature, an "@" (commercial-at) symbol, and completed with a sequence of floating-point values. The first three values of the numerical sequence are the X, Y, and Z coordinates of the point source. The fourth number is the concentration at the source location. To describe the shape of the gradient away from the source, the last three numbers are exponent, modifier, and radius values.

Setting the exponent value to 0 causes the gradient to be uniform at the full source concentration throughout the environment space. An exponent specified at greater than 1 describes a decrease in concentration at distance increases from the source.

```
S Nutrient @ 0 0 0 1 0 1 1,
S Morphogen @ 0 0 0 1 0.5 2 1
]
</Shade>
```

F. Ontogeny Engine

When a simulation is started, the configuration file is parsed and transmitted by the user interface to the ontogeny engine whereby the ontogeny engine is initialized to an initial step boundary from which subsequent steps may be taken. In one embodiment, the initial step boundary can define a reference point from which a simulation can commence or continue. In the present implementation, the ontogeny engine is driven one step at a time from the initial step boundary to subsequent step boundaries. The ontogeny engine may be implemented on any of a variety of computing systems known in the art. In one embodiment, the ontogeny engine supports user control of the number of steps performed in the simulation without additional instruction.

For each step in the ontogeny engine, the following functions, detailed below, can be performed until the user halts the simulation or a configured halting condition described in E1 is reached:
    killCells
    stepCells
    stepECM
    stepPhysics One of ordinary skill in the art will recognize that the ontogeny engine can perform one or more of these functions in any combination and/or order. For example, in some embodiments, the ontogeny engine can be advanced from an initial step boundary to subsequent step boundary by performing a stepCells function. In another embodiment, the advancing can include performing a stepCells function and a stepPhysics function. It will also be recognized that each function employed during the advancing of the ontogeny engine can be performed in a sequential and/or simultaneous manner. In a further embodiment, one or more functions can be performed in an asynchronous manner. For example, advancing from a first current step boundary to a next step boundary may include a stepCells function and advancing from a second current step boundary to a next step boundary may include a killCells function and a stepPhysics function.

Pseudocode described and presented herein is understood to be exemplary only. Accordingly, one of ordinary skill in the art will recognize that other code and program instructions, order of steps, etc. can be used to implement the features and functions described herein.

F1. Embodiments of Narrative Pseudocode for killCells Function

As described under Section B and in FIG. 3B at 37, killCells removes virtual cells marked for death in a previous step. When first marked by a flag set in the source code controlling the cell, cell death is treated as no longer performing any metabolic or transcription algorithms.

Upon being marked for death, the cell can begin a countdown to be removed from the simulation and so will no longer be involved in any physical interactions. In one embodiment, this countdown is satisfied immediately and so the cell will be removed immediately upon being marked for death.

```
function killCells
{
    while there are cells to kill
    {
        nextCellToDie ← the next cell to kill
        for each Cell in the simulation
        {
            if Cell == nextCellToDie
            {
                //internally, the cell simply flags itself as dead
                Cell.die
            }
        }
    }
}
```

F2. Embodiments of Narrative Pseudocode for Step Cells Function

Described under Section B and in FIG. 3B at 38, this function can be performed in each simulation step. In some embodiments each virtual cell can be independently subjected to internal step logic. In summary, signals from source cells are copied to target regions for detection by potential target cells, cells gather signals so placed, and cell then performs a step of metabolism, as described in F5.

```
// this function is called on the simulation itself
function stepCells
```

```
{
    remove all dead cells from simulation
    if there are any cell signals
    {
        for each cell's region
        // where region is an imaginary sphere about the cell
        {
            exchange signal molecules with overlapping regions
        }
    }
    // each cell's immediate region now recognizes external molecules
    // signaled to it from overlapping regions from other cells.
    for each Cell in the simulation
    {
        update Cell's region with external molecules
            from nutrient molecule source
        metabolizeCell    // (see below)
    }
}
```

F3. Embodiments of Narrative Pseudocode for stepECM Function

As described under Section B and in FIG. 3B at 40, this function can update adhesions between sub-spheres that represent extra cellular matrix (ECM).

```
function stepECM
{
    // based on simulation adhesions:
    breakOverextendedBindings between ECM subunits
    connectECM between subunits
    decayECM    // over several steps, ECM subunits
    decay and are removed
}
```

F4. Embodiments of Narrative Pseudocode for stepPhysics Function

As described under Section B and in FIG. 3B at 41, physical interaction rules can be processed following metabolism to update a cell's location in response to cell death, division, growth, adhesion changes, or perturbation. In other embodiments, stepPhysics function can be performed at any time or in any order with respect to other function and operations during simulation. For stepPhysics operations, the unit spheres that represent the physical presence of cells (or ECM) can be treated with only limited regard to their cell (or ECM) membership. Accordingly, in one embodiment, each sphere location and velocity is updated iteratively based on forces calculated to be acting upon it.

```
// this function is called on the simulation itself
function stepPhysics
{
    Initialize Bag as an empty set of unit spheres
    Initialize Network as an empty set of general adhesions
    for each cell in the simulation
    {
        collect all cell sub-unit spheres into Bag
    }
    collect all ECM sub-unit spheres into Bag
    create inter-object adhesions if adhesion conditions met
    remove overextended adhesions between inter-object unit spheres
    update adhesion forces between collected inter-object unit spheres
    if projectile fired
    {
        for each cell touched by projectile
        {
            //internally, the cell flags itself as dead
            instruct cell to die
        }
    }
    for each cell to be nudged, collect forces from user nudges
    for each Iteration for configured-iterations-per-step
    {
        for each Sub-Unit-Sphere in Bag
        {
            accumulate force from all nudges onto Sub-Unit-Sphere
        }
        for each Sub-Unit-Sphere in Bag
        {
            accumulate forces from all adhesions in Network
                onto Sub-Unit-Sphere
        }
        for each Sub-Unit-Sphere in Bag
        {
            accumulate repulsion force onto Sub-Unit-Sphere
        }
        for each Sub-Unit-Sphere in Bag
        {
            accumulate damping of forces onto Sub-Unit-Sphere
        }
        for each Sub-Unit-Sphere in Bag
        {
            // translocation distance based on current velocity, net
            // forces adjusting that velocity & elapsed time per iteration
            translocate Sub-Unit-Sphere in Bag
        }
    }
}
```

F5. Embodiments of Narrative Pseudocode for metabolizeCell Function

The metabolizeCell function provides additional operation directives for stepCells function described above under F2. In one embodiment, if a cell has not been marked for death, the stepCells function will invoke a metabolic processing step. In one embodiment, a metabolic processing step can be configured to apply rules directed to metabolic interactions and genetic transcription calculations. Each metabolic interaction is computed to assess molecule flux (e.g., the molecule value consumed and produced according to the configured chemistry equations and gene units). The molecules produced from these virtual metabolism and genetic transcription calculations are then accumulated in the context of molecule strength and/or relative concentration. Over subsequent steps, the molecule strength values can be reduced so as to simulate molecular decay. If the cell has not reached its death threshold (that is, has not accumulated enough death action molecules), growth, adhesion, and division actions are performed if the cell has reached those respective thresholds.

```
// this function is called on a given cell in simulation
function metabolizeCell
{
    if alive
    {
        // reaction will consume and produce molecules inside, outside,
        // or on the surface of the cell based on configured equations
        react according to molecular interaction equations
        produce ECM sub-units according to configured ECM production
            instructions
        transcribeGenome                          // (see below)
        accumulate internal molecules // from reaction & transcription above
        accumulate action molecules   // from reaction & transcription above
    }
    decay action molecules              // at a constant rate
    decay internal molecules            // at a constant rate
    decay surface molecules             // at a constant rate
    if alive
    {
        if flagged to die or reached threshold of death action molecule
        {
            alive ← FALSE
        }
    }
    if alive
    {
        position produced ECM sub-units into environment
        if reached threshold of growth action molecule, and
        if not already at configured maximum size
        {
            add a sub-unit sphere to cell
            reduce accumulated growth action molecule by the growth threshold
                amount
        }
        // rigidity, elasticity, plasticity adhesions are
        // added, removed, or amended according to applied forces
        apply adhesions to cell sub unit spheres
        if reached threshold of divide action molecule
        {
            reduce accumulated divide action molecule by the
                divide threshold amount
            divide cell sub unit spheres between the parent
                cell and a new daughter cell
            divide cell molecules between parent and daughter cells
            distribute and adjust adhesions between parent and daughter cells
        }
    }
}
```

F5. Embodiments of Narrative Pseudocode for transcribeGenome Function

The following function provides additional detail for metabolizeCell described above under F5. See section E4 for the description of a genome and its components. Each gene unit of the genome can be compared for affinity and a corresponding promotion is calculated. If the promotion is sufficient to result in a concentration (e.g., strength value applied), the gene unit products specified in its structural region are produced and added to the cell's internal molecules, either as transfactors to be considered in future transcriptions or chemistry reactions or as action potentials accumulated for growth, division, et al.

The calculation of promotion, referred to in the pseudocode below, is referred to in Section C, in FIG. 5 at 100, specified per Section E.3.6.2, and further described in FIG. 20. One such calculation used in the preferred embodiment is $$\frac{SpecifiedEffect}{1 + e^{-(SpecifiedAffinity - SpecifiedPromotionMidpoint)}}$$

The updating of concentration, referred to in the pseudocode below, is described in Section E.3.6.2 and specified by the genome (see Section E.4). In one embodiment, a calculation used is the product of the SpecifiedConcentration and the CalculatedPromotion from the promotion calculation.

```
// this function is called on a genome by its cell during simulation
function transcribeGenome
{
    for each GeneUnit in Genome
    {
        calculate Promotion on GeneUnit based on present
            transfactors and presented chemistry
        update Concentration from Promotion
        if Concentration > 0
        {
            for each Gene in GeneUnit's structural region
            {
                if Specified-Gene-Product is a Transfactor
                {
                    accumulate concentration of Transfactor
                        specified in the GeneUnit into Cell's store
                }
                else
                {
                    accumulate concentration of Action-Molecule
                        product specified in the GeneUnit
                        into Cell's store
                }
            }
        }
    }
}
```

```
            }
        }
    }
}
```

G. Applications of the Cell-Centric Simulation System to Modeling Multicellular Tissue Development This section describes methods and strategies for generating multicellular virtual tissues having selected behavioral and morphological properties, and for testing such virtual tissues.

Essentially, three steps can be followed to develop a particular model:
1) Describe the model: identify the criteria that indicates how the model will be recognized;
2) Define cell states: identify the various cell states expected to be seen in the model;
3) Write configuration file: encode the cell state transitions into a configuration with virtual genes and chemical-interaction rules.

The following examples illustrate tissue modeling for three different tissue types and all assume a free space environment where cells can be shaped with the marbles-in-a-bag approach described under D7. The examples are intended to illustrate how the virtual genome and chemistry equations may be selected to achieve specific tissue behavior and morphology, but are in no way intended to limit the scope of the invention.

G1. Example 1: Simple Model of Cells Committed to Differentiation

Figure 24B:
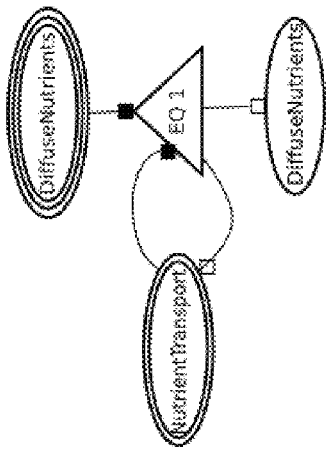
FIGS. 24A-24O are schematic flow diagrams illustrating molecules and actions, virtual genes and gene products, and chemical-interaction rules for modeling a multicellular tissue in accordance with the simulation of biological events described in Example 1 of sections C and G1, and in accordance with an embodiment of the disclosure.
Figure 24D:
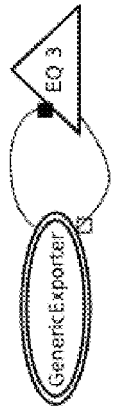
Figure 24A:
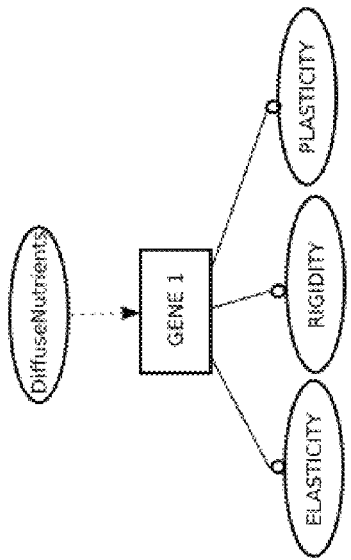
Figure 24C:
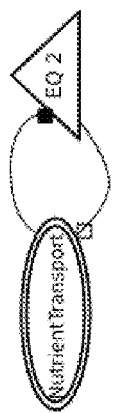
Figure 24K:
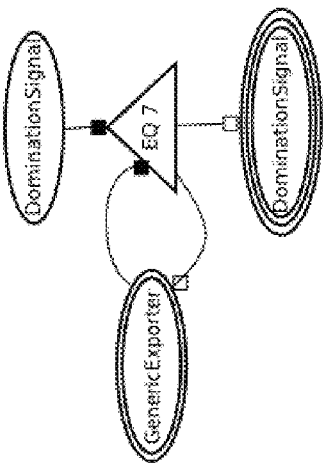

Introduced in Section D, the first example demonstrates how cells can develop a propensity to differentiate. This section describes an analysis and design approach with which to generate that example. The SGRN for this example is diagramed in FIG. 9 and discussed above in Section C. FIGS. 24A-24O are schematic flow diagrams illustrating molecules and actions, virtual genes and gene products, and chemical-interaction rules for modeling a multicellular tissue in accordance with the simulation of biological events described in Example 1 of sections C and G1, and in accordance with an embodiment of the disclosure.

G1.1. Describing the Model

Figure 22:
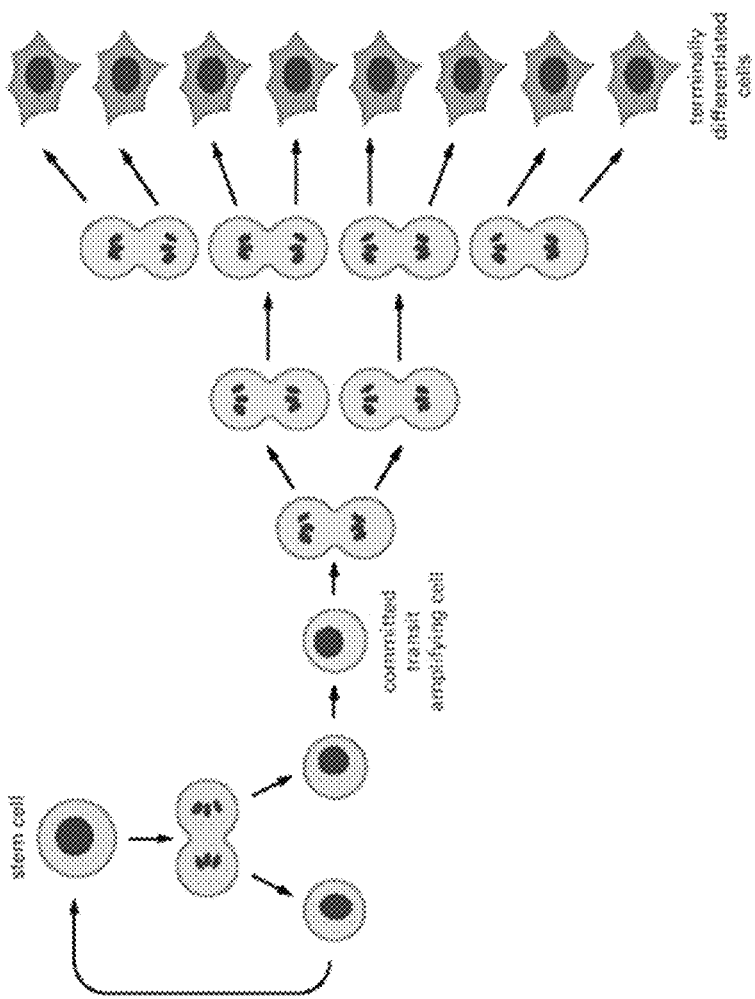
FIG. 22 is a schematic diagram illustrating the role of transient amplifying cells in the development of epithelial tissue.
Figure 23A:
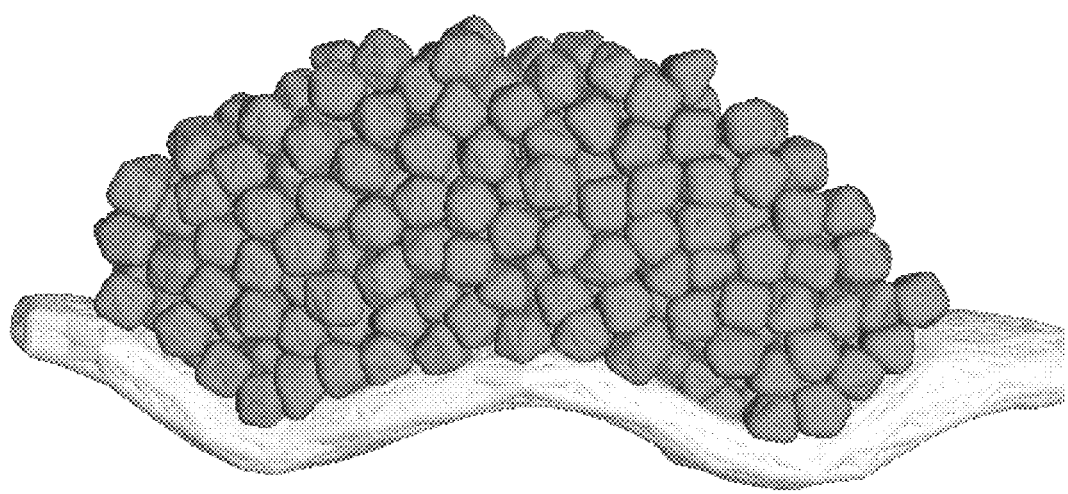
FIGS. 23A-23D are isometric views illustrating a modeled epithelial tissue, with the modeled basement membrane highlighted (23A), the modeled tissue's stem cells highlighted (23B), with the modeled cells neighboring the stem cells highlighted (23C), and with a population of modeled lipid-producing cells highlighted (23D) in accordance with an embodiment of the disclosure.
Figure 23B:
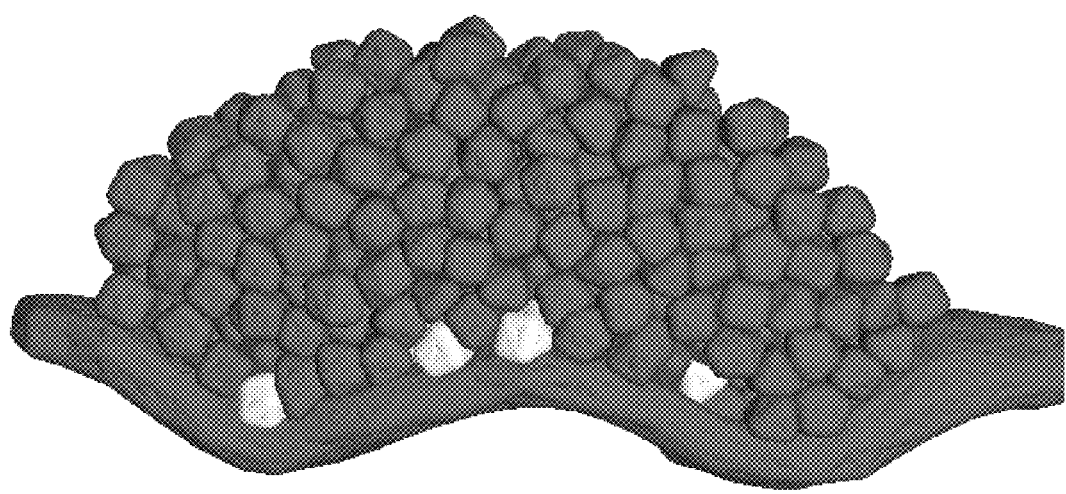
Figure 23C:
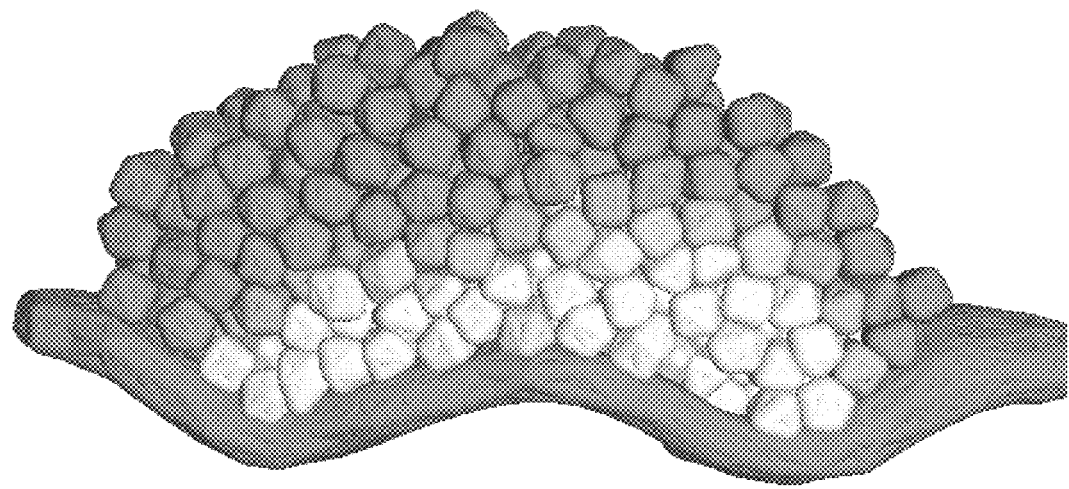
Figure 23D:
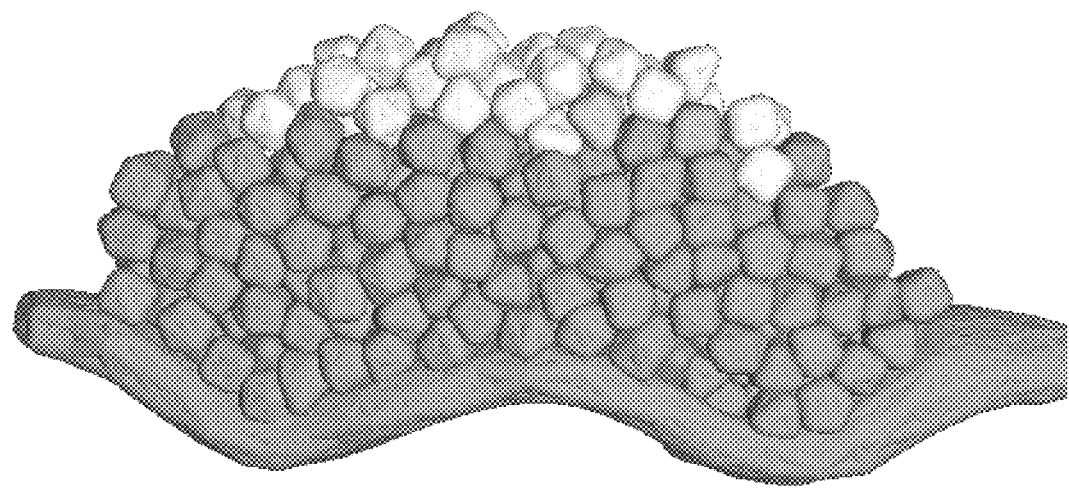

The object is to produce some kind of chemical disparity between two cells that can lead to a persistent or permanent difference between them. This mechanism closely resembles biological mechanisms for generating daughter cells from dividing stem cells. Typically one daughter cell remains a stem cell while the other daughter cell differentiates to some other type of cell. FIG. 22 is a schematic diagram illustrating the role of transient amplifying cells in the development of epithelial tissue.

To generate this model with the preferred embodiment, the user starts with the initial cell. The intent is to have this cell grow and divide such that two cell types result: Dominator, similar to the initial cell state, and Dominated, distinct from Dominator. The cells are to have chemical differences resulting from signaling from neighbor cells. The initial cell will produce new cells that will signal one other. Due to the nature of the signaling, no two cells will receive the exact same amount of signal.

The goal is to build a metabolic pathway and adjust it to use this difference in signaling strength to produce the intended differences in the cells. The cells will be competing to reach the Dominator state: the first to reach that state will commit to the Dominator state, suppress the other cells from reaching that state, and actively signal them to instead transition to the Dominated state. Until a cell reaches the Dominator state, all cells will be uncommitted.

G1.2. Defining Cell States

First, a list of cellular states and their corresponding behaviors in different situations must be made from which to design a suitable genome. As appropriate, listed states may have mutual exclusivity with other states. For this example model, three cell states are listed:

TABLE 5

| Categorical Examples and Descriptions of Cell States | |
|---|---|
| NEUTRAL: | Neutral cells have not committed to any path but pursue reaching Dominator state when they detect enough neighbors around them. They can grow and divide, send and receive a "neighbor" signal, can receive "become Dominated" signal, and can attain either Dominator or Dominated states. |
| DOMINATOR: | These cells pursue retention of the Dominator state and influence surrounding cells to reach Dominated state. Dominator cells cannot grow and divide. They can send and receive a "become Dominated" signal. |
| DOMINATED: | These cells have reached a terminal state and so cannot transition further. These cells cannot grow or divide. |

G1.3. Writing the Configuration File

A configuration file to submit to the ontogeny engine can be written. Section E describes key syntax. From an initial simulation configuration template, features and details are successively added until the desired outcome is reached.

Below is a simulation configuration template; it does not yet contain any model specific equations or genetic information. Its content is based primarily on previous practice that worked well in various models.

Configuration Example

```
<CsIndividual>
    <Simulation>
        <Cell>
            <Chemistry><Smooth/></Chemistry>
            // Starting the Cell off with some surface molecules
            <InitialChemistry>
                (NutrientTransport) 50
                        (GenericExporter) 50
                        (ECMDetector) 50
            </InitialChemistry>
```

```
            <ChemistryEquations>
                    { DiffuseNutrients } + (NutrientTransport) =
                            .1 DiffuseNutrients + ( 1.11111111111111 NutrientTransport );
                    ( NutrientTransport ) =
                            ( 1.11111111111111111 NutrientTransport );
                    ( GenericExporter ) = ( 1.1111111111111111 GenericExporter );
            </ChemistryEquations>
            // A pretty standard promotion curve
            <Promoter>
                    <Smooth>
                            <PromotionMidpoint> 10 </PromotionMidpoint>
                            <ActiveConcentration> 1 </ActiveConcentration>
                    </Smooth>
            </Promoter>
            //This large maximum size makes us be careful about regulating growth
            <MaximumSize>300</MaximumSize>
            // Size of the first cell, larger than a typical somatic
            // cell for this model, more like an egg
            <InitialSize>40</InitialSize>
            <MinimumSize>6</MinimumSize>
    </Cell>
    <Signal> // A very short range signaling scheme
            <Local>
                    <Separation> .1 </Separation>
            </Local>
    </Signal>
    // These physics settings tend to work well, they're used in
    // lots of models
    <Physics>
            <IterationsPerStep>50</IterationsPerStep>
            <TimePerStep>.2</TimePerStep>
            <DampingMultiplier>0.99</DampingMultiplier>
            <NudgeMagnitude>1</NudgeMagnitude>
    </Physics>
    <MaxInterAdhesionLength>0.65</MaxInterAdhesionLength>
</Simulation>
<Genome>
[
    [ DiffuseNutrients .3 ] [ Plasticity, Elasticity, Rigidity ]
]
</Genome>
// Our cells will live in an environment evenly covered with
// DiffuseNutrients
<Shade><UseRadius/><UseModifier/>
[
    S DiffuseNutrients @ 0 1 0 5 1 1 1000
]
</Shade>
</CsIndividual>
```

This initial configuration template includes one gene unit, three chemistry equations, and surface molecules that represent the state the cell is to start as. These surface molecules allow the cell to bring in DiffuseNutrients. The single gene unit, illustrated in FIG. 24A, is to produce structural molecules to give the cell a reasonable shape. The three chemistry equations, illustrated in FIGS. 24B-24D, are to maintain the initial surface molecules and facilitate transport of DiffuseNutrients. The coefficients of 1.1111 . . . are to help retain those nondecaying and unconsumed molecules; that is, surface transport molecules are replaced at a greater rate so as to offset their consumption or decay.

In practice, the template <Physics> settings produce a relatively stable environment; not all potential settings produce smooth results. The template <Smooth> promotion allows any molecule, no matter how poorly matched, to promote any gene unit, even at 0.0 affinity and concentration. For this reason, promotion midpoints for Smooth promotion are typically set relatively high to reduce the promotion at 0.0 affinity and concentration. With Smooth promotion, gene units often include explicit inhibitors to cancel out interference from molecules that should not promote the assembly.

As is, a simulation run with this initial configuration would develop a single, reasonably shaped cell that does not grow or divide, consumes DiffuseNutrients, and maintains its shape. Gene units and equations are added to generate the desired differentiation behavior.

First, the state of the cells should reflect how many neighbor cells are around: all cells need to be able to send and receive a general awareness signal. While each cell exists and can transcribe Diffuse Nutrients, it is to produce internal molecules for this purpose. ExistanceSignal is to be a signal to other cells of given cell's existence and ExistanceSignalReceiver is to be placed on the surface of the cell to receive such signals from other cells. FIG. 24E shows, as GENE 2, a gene unit that produces these molecules with the promoter and product designations shown below. This gene unit is added inside the square brackets subordinate to the <Genome> tag.

Configuration Example

[DiffuseNutrients 5] [ExistanceSignal, ExistanceSignalReceiver]

To be a signal, the surface molecule GenericExporter, established in <InitialChemistry>, must participate in a chemistry equation to transport the internally produced ExistanceSignal molecules out of the cell; see FIG. 24H. The equation must also restore GenericExporter to prevent its consumption. As with all chemistry interactions, the below text is to be added under the <ChemistryEquations> tag:

Configuration Example

ExistanceSignal+(GenericExporter)=(GenericExporter)+{ExistanceSignal};

To receive similar signals from other cells, ExistanceSignalReceiver must be placed onto the cell surface. Again, this is done with a chemistry equation, see FIG. 24I and below:

Configuration Example

ExistanceSignalReceiver=(ExistanceSignalReceiver);

Finally, the actual reception of ExistanceSignal external to the cell requires its transport into the cell by the surface ExistanceSignalReciever. Such molecules transported into the cell will be represented by internal NeighborPresent molecules. Again, this is done with a chemistry equation, see FIG. 24J and below:

Configuration Example

{ExistanceSignal}+(ExistanceSignalReceiver)= NeighborPresent;

With the addition of the four previous configuration instructions, the signaling necessary for recognizing the presence of neighboring cells and broadcasting a cell's presence is complete, but cell response to such signaling is not.

To keep the overall model as a small cluster of cells, the cells are to grow and divide in the presence of nutrient only as long as there are not too many neighbors present. This does not preclude cells with a Dominated state from growing and dividing when they are isolated, but growth and division will stop when in a small cluster. This behavior is configured by the addition of GENES 3 and 4, illustrated in FIGS. 24F and 24G. The configuration instructions for inclusion in the genome are given below:

Configuration Example

[DiffuseNutrients 0.18, NeighborPresent −3] [Growth]
[DiffuseNutrients 0.18, NeighborPresent −3] [Division]

To establish the potential for cell differentiation, cells need to track their Dominator state and need to signal other cells of their progress to that state. This requires a gene unit to promote a Dominator state in response to the presence of neighboring cells. The NeighborsPresent molecule received from other cells will promote this gene unit to produce both Dominator molecule for internal accumulation and DominationSignal as a signal for negotiating the competition between cells to attain the Dominator state, FIG. 24K:

Configuration Example

[NeighborPresent 3, Dominated −10, Dominator 3]
[Dominator, DominationSignal]

Figure 24L:
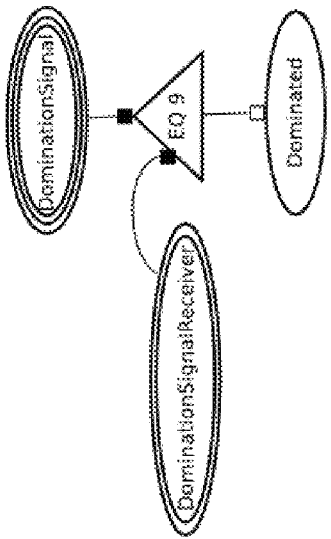

As in the signaling to indicate neighbor presence, this signal must be transported out, via GenericExporter, as it is produced, FIG. 24L:

Configuration Example

DominationSignal+(GenericExporter)=(GenericExporter)+{DominationSignal};

Likewise, similar signals from other cells must be received to complete the signal pathway. A surface molecule, DominationSignalReceiver, is necessary to transport the external signals into the cell. As the external signal molecules are brought in, they will accumulate as internal Dominated molecules, FIG. 24N:

Configuration Example

{DominationSignal}+(DominationSignalReceiver)= Dominated;

DominationSignalReceivers require an origin: this is an opportunity for differentiation. By attenuating the production of the surface molecules for signal reception, cells can vary their response to signals from other cells. As cells accumulate internal Dominator molecule by their own signal production (see above), resistance to other cells' signal should increase until that attains the Dominator state. As cells accumulate internal Dominated molecule from other cells' signals, the cells will reduce their signaling until they become inert and no longer send or receive Domination signals from their neighbors.

See FIG. 24O and the configuration instruction to be added below. The "Dominator −10" in a new gene unit's control region will inhibit the expression of internal DominationSignalReceiver molecule. Conversely, as cells accumulate Dominated molecules from other cells, this expression is promoted. Cells reinforce the expression of this gene unit with DiffuseNutrients, further setting them on the path of terminal differentiation.

Configuration Example

[DiffuseNutrients 5, Dominator −10, Dominated 5]
[DominationSignalReceiver]

Figure 24M:
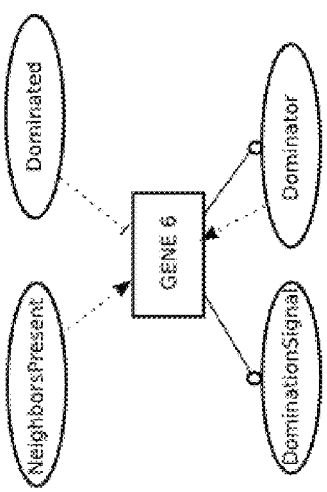
Figure 24N:
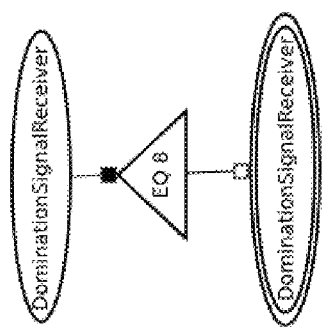
Figure 24O:
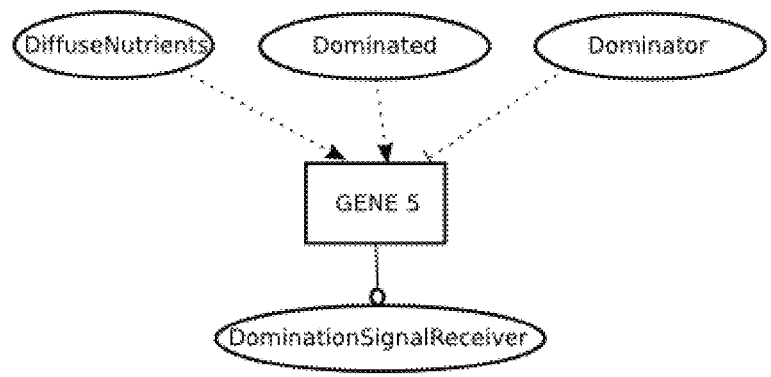

As before, a chemistry equation moves any produced DominationSignalReceiver to the cell surface, FIG. 24M:

Configuration Example

DominationSignalReceiver=(DominationSignalReceiver);

In practice, the design of configuration instructions to create necessary gene unit and chemistry equations requires trial and error of the involved coefficients to refine the model. If cells receive too much signal and transition too quickly, the signal receptor coefficient will require adjustment. If cell only partially transit to another state and continue uncommitted for longer than desired, it may be necessary to adjust the gene unit expression for state transitions to be more definite.

The following is an exemplary configuration file generated from the Example 1 described above:

```
<CsIndividual>
    <MoleculeCatalog></MoleculeCatalog>
    <Simulation>
        <ECMDefinitionRules></ECMDefinitionRules>
        <AdhesionRules>
            Dominator : Dominator ;
        </AdhesionRules>
        <Cell>
            <Axisifier><Random/></Axisifier>
            <Chemistry><Smooth/></Chemistry>
            <InitialChemistry>
                (NutrientTransport) 50
                (GenericExporter) 50
            </InitialChemistry>
            <ChemistryEquations>
                { DiffuseNutrients } + (NutrientTransport) =
                    .1 DiffuseNutrients + ( 1.11111111111111 NutrientTransport );
                ( NutrientTransport ) =
                    ( 1.1111111111111111 NutrientTransport );
                ( GenericExporter ) = ( 1.1111111111111111 GenericExporter );
                ExistanceSignal + ( GenericExporter ) =
                    ( 1.1111111111111 GenericExporter ) + { ExistanceSignal };
                ExistanceSignalReceiver = ( ExistanceSignalReceiver );
                { ExistanceSignal } + ( ExistanceSignalReceiver ) =
                    20 NeighborPresent;
                DominationSignal + ( GenericExporter ) =
                    ( 1.1111111111111 GenericExporter ) + { DominationSignal };
                DominationSignalReceiver = ( DominationSignalReceiver );
                { DominationSignal } + ( DominationSignalReceiver ) =
                    20 Dominated + 20 GrowABit;
            </ChemistryEquations>
            <Promoter>
                <Smooth>
                    <PromotionMidpoint> 10 </PromotionMidpoint>
                    <ActiveConcentration> 1 </ActiveConcentration>
                </Smooth>
            </Promoter>
            <MaximumSize>300</MaximumSize>
            <InitialSize>40</InitialSize>
            <MinimumSize>6</MinimumSize>
            <ECMProductionRules></ECMProductionRules>
        </Cell>
        <Signal>
            <Local>
                <Separation> .1 </Separation>
            </Local>
        </Signal>
        <Physics>
            <IterationsPerStep>50</IterationsPerStep>
            <TimePerStep>.2</TimePerStep>
            <DampingMultiplier>0.99</DampingMultiplier>
            <NudgeMagnitude>1</NudgeMagnitude>
        </Physics>
        <MaxInterAdhesionLength>0.65</MaxInterAdhesionLength>
    </Simulation>
    <DevelopmentEngine>
        <MaxSteps>10000</MaxSteps>
        <StableSteps>10000</StableSteps>
    </DevelopmentEngine>
    <Genome>
        [ DiffuseNutrients .3 ] [ Plasticity, Elasticity, Rigidity ],
        [ DiffuseNutrients 5 ] [ ExistanceSignal, ExistanceSignalReceiver ],
        [ DiffuseNutrients .18, NeighborPresent -3 ] [ Growth ],
        [ DiffuseNutrients .18, NeighborPresent -3 ] [ Division ],
        [ DiffuseNutrients 5, Dominator -10, Dominated 5 ]
            [ DominationSignalReceiver ],
        [ NeighborPresent 3, Dominated -10, Dominator 3 ]
            [ Dominator, DominationSignal ]
    </Genome>
    <Shade><UseRadius/><UseModifier/>
    [
    S DiffuseNutrients @ 0 1 0 5 1 1 1000
    ]
    </Shade>
</CsIndividual>
```

The resulting SGRN from this configuration is given by FIG. 9 and may be read as described in Section C.

G2. Example 2: Tissue Sheet with Stem Cell Niches

Figure 21:
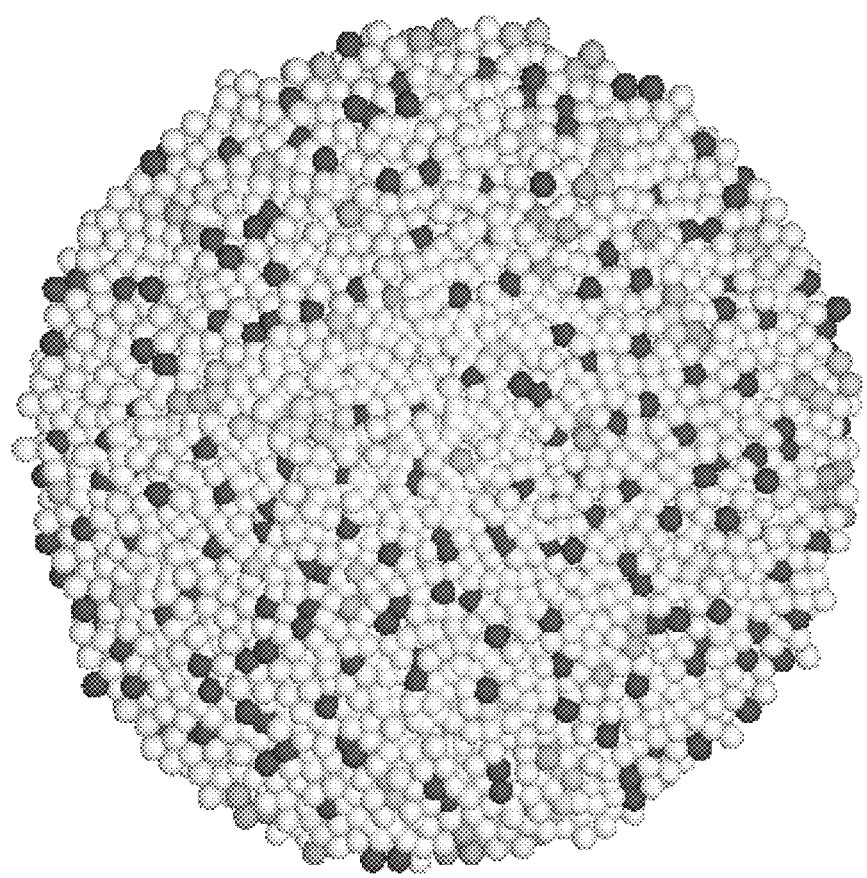
FIG. 21 is an isometric view illustrating a modeled cellular sheet including virtual stem cells, in accordance with the simulation of biological events described in Example 2 of section G2 and in accordance with an embodiment of the disclosure.

FIG. 21 is an isometric view illustrating a modeled cellular sheet including virtual stem cells, in accordance with the simulation of biological events described in Example 2 of section G2 and in accordance with an embodiment of the disclosure. This example is more complex than the first, in section G1, and includes stem cell niches and cell differentiation, rather than just demonstrating the propensity for differentiation. The sheet is formed by placing two very large fixed spheres (see section E.3.5) about the initial cell to establish relatively flat, metabolically inert obstacles in the environment and so physically limit the growth to the sheet. The user may configure the visualization engine to inhibit display of these large fixed spheres to allow unobstructed examination of the subject sheet.

Figure 25A:
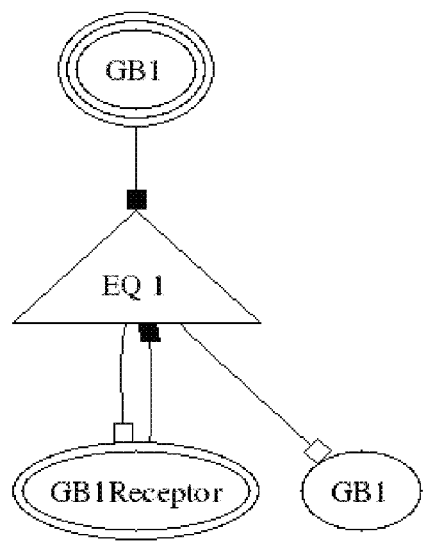
Figure 25B:
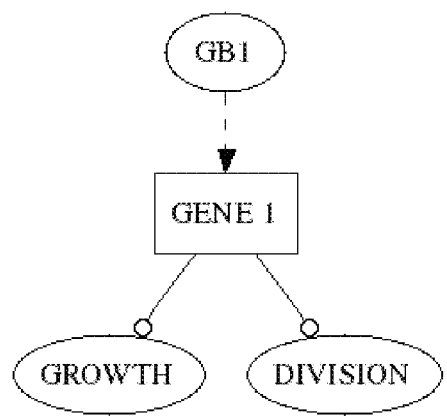

Signal isolation similar to that seen in Example 1 was used to establish cell differentiation leading to two types of cells: undifferentiated stem-cell-like cells and differentiated cells analogous to transit amplifying cells. FIGS. 25-A-25K are schematic flow diagrams illustrating molecules and actions, virtual genes and gene unit products, and chemical-interaction rules for modeling a multicellular tissue in accordance with the simulation of biological events described in Example 2 of section G2, and in accordance with an embodiment of the disclosure. FIG. 26 is a schematic flow diagram illustrating a modeled SGRN for simulating development of a multicellular tissue with stem-cell niches in accordance with the simulation of biological events described in Example 2 of section G2, and in accordance with an embodiment of the disclosure.

G2.1. Describing the Model

This model is intended for exploration of a signaling mechanism to explain how stem cell niches might become evenly distributed within a tissue. In a physically constrained sheet of cells, slow-growing, isolated, stem-like cells are each surrounded by numerous, faster-growing, transit-amplifying cells.

G2.2. Decomposing the Problem to Identify Cell-Level Features

There are two basic cell conditions in this model: (1) the undifferentiated condition belonging to the initial cell and (2) a condition in which cells have been induced to commit by signals from an undifferentiated cell and remain committed to differentiating in the presence of minimal ongoing signal. These conditions loosely represent the relationship between stem cells and transit-amplifying cells in the basal layer of epidermis.

In general, stem cells are regulated by niches. In some tissues, these niches are clearly defined and precisely located. In others, they may be scattered throughout the tissue with no apparent specialized niche cells. Regardless, the number of stem cells is relatively small compared to the number of differentiating or differentiated cells and the stem niches are relatively isolated from one another. In this example, individual virtual stem cells are isolated, effectively representing an entire niche. When an undifferentiated cell divides, one of them is to remain undifferentiated and the other commits to differentiation: this dynamic keeps the density of stem-like cells nearly constant. This behavior implies a signaling competition or some kind of asymmetric division. This model explores a signal isolation mechanism to support the intended behavior.

In basal epidermis, transit-amplifying cells normally remain transit-amplifying cells until they are removed from the basal layer by population pressure or asymmetric division with respect to the basement membrane. However, in the event of injury where stem cell populations are damaged, some transit-amplifying cells may revert to stem cell conditions as part of the repair process. This implies that although commitment to differentiation is not trivial, at least some minimal signaling from stem cells may be required to keep transit-amplifying cells from reverting to stem cells.

G2.3. Writing the Configuration File

The configuration is designed starting from a minimal simulation template. A <MaxInterAdhesionLength> setting of 0.25 allows adhesions between cells to stretch up to half the radius of unit spheres (i.e., r=0.5) before breaking (see E.3.2). This allows some computational variance for physics resolution and acknowledges that unlike model spheres, cells are flexible.

Configuration Example

```
<CsIndividual>
    <Simulation>
        <MaxInterAdhesionLength>0.25</MaxInterAdhesionLength>
        <SingleAdhesionRule>0</SingleAdhesionRule>
        <Cell>
            <Chemistry><Default/></Chemistry>
        </Cell>
    </Simulation>
</CsIndividual>
```

<Physics> settings from previous practice that worked well in various models are used to establish an initial configuration. Unlike the configuration of Example 1, <IterationsPerStep> is not specified. The simulation is left to dynamically adjust this parameter for each step based on the <MaxVelocityChange> and <TimePerStep> values and current calculated velocities. As in Example 1, the <DampingMultiplier> and <RepulsionMultiplier> values are close to one another—identical in this case. Practice with the preferred embodiment has shown that balanced values tend to work better and that absolute values tend to be less significant than the ratio.

Configuration Example

```
<Physics>
    <MaxVelocityChange>2</MaxVelocityChange>
    <TimePerStep>0.5</TimePerStep>
    <DampingMultiplier>2</DampingMultiplier>
    <RepulsionMultiplier>2</RepulsionMultiplier>
</Physics>
```

Instead of the <Smooth> promotion from Example 1, <Smoother> promotion is used to yield 0.0 promotion at 0.0 affinity and concentration; this allows lower promotion midpoints to be chosen for developer convenience. In this example, <PromotionMidpoint> is set to 5 so that the effective range of promotion is covered by concentrations from 0 to 10. The <Slope> is set at 3 so that key promotion levels occur at convenient concentrations. 50% of the promotion range is covered between concentration 4, where promotion is 25%, and concentration 6, where promotion is 75%. Above concentration 10, promotion is asymptotically maximal.

Configuration Example

```
<Promoter>
    <Smoother>
        <PromotionMidpoint>5</PromotionMidpoint>
        <Slope>3</Slope>
        <ActiveConcentration>1</ActiveConcentration>
    </Smoother>
</Promoter>
```

The following is the resulting initial configuration from which to begin development of the second example:

Configuration Example

```
<CsIndividual>
    <Simulation>
        <MaxInterAdhesionLength>0.25</MaxInterAdhesionLength>
        <SingleAdhesionRule>0</SingleAdhesionRule>
        <Physics>
            <MaxVelocityChange>2</MaxVelocityChange>
            <TimePerStep>0.5</TimePerStep>
            <DampingMultiplier>2</DampingMultiplier>
            <RepulsionMultiplier>2</RepulsionMultiplier>
        </Physics>
        <Cell>
            <Chemistry><Default/></Chemistry>
            <Promoter>
                <Smoother>
                    <PromotionMidpoint>5</PromotionMidpoint>
                    <Slope>3</Slope>
                    <ActiveConcentration>1</ActiveConcentration>
                </Smoother>
            </Promoter>
        </Cell>
    </Simulation>
</CsIndividual>
```

To simplify the example, mechanisms for cell cohesion or division orientation are unwanted. The below instructions, under <Simulation>, constrain the model to grow between a pair of effectively infinite plates (see E3.5), limiting tissue growth to a single-layer sheet.

Configuration Example

```
<FixedSpheres>
    [0, -1000, 0] 1000,
    [0, 1001, 0] 1000
</FixedSpheres>
```

For simplicity and speed, only a very short range Local signaling with Separation 0.2 is used (see E3.1). This requires cells to be touching or nearly touching for cell signals to be exchanged. The following is added under <Simulation>.

Configuration Example

```
<Signal>
    <Local>
        <Separation>0.2</Separation>
    </Local>
</Signal>
```

To develop numerous cells quickly in minimal space, the minimum cell size is set to one subsphere and the maximum cell size to two subspheres. However, the initial cell will be larger than the maximum and have an odd number of subspheres to guarantee an asymmetrically-sized first division. As the initial 13-subsphere cell divides into thirteen individual cells in the first few steps, it will rapidly generate a mix of cells with different signaling environments and molecular concentrations. The following is added under <Cell>.

Configuration Example

```
<InitialSize>13</InitialSize>
<MinimumSize>1</MinimumSize>
<MaximumSize>2</MaximumSize>
```

A cell nutrient molecule named GB1 is to be uniformly available throughout the environment. As a entry of <Shade> under <CsIndividual>, a gradient builder for GB1 is added (see E5) with a strength parameter of 1.0 and an exponent of 0.0. With an exponent of 0.0, the concentration of GB1 will be at the full strength of 1.0 everywhere in the environment; the location, modifier, and radius values are irrelevant.

Configuration Example

```
<Shade><UseRadius/><UseModifier/>
    [ S GB1 @ 0 0 0 1 0 1 1 ]
</Shade>
```

For reference ease, a <MoleculeCatalog> is established, under <CsIndividual>, with GB1 as its first entry. A high Sensitivity setting of 10 in the molecule signature effectively demands exact matching with regulatory gene units.

Configuration Example

```
<MoleculeCatalog>
    GB1 [10, 10];
</MoleculeCatalog>
```

As in the first example, surface transport molecules are specified as both reactants and products so that they are not consumed or altered during molecule transport. To import external GB1 via surface GB1Receptor, a chemistry equation is added, FIG. 25A:

Configuration Example

```
<ChemistryEquations>
    { GB1 } + ( GB1Receptor ) = GB1 + ( GB1Receptor );
</ChemistryEquations>
```

So cells do not have to maintain surface transport molecules via gene unit expression as in the first example, all surface transport molecules in this model are configured with decay rates of 0.0. The instruction below is added to the <MoleculeCatalog>:

Configuration Example

GB1Receptor [20, 10] 0.0;

GB1 is to be used to provide a reference concentration for gene unit promotion. To keep associated gene units fully promoted, cells must be able to take in GB1 and maintain its concentration at or above 10. Therefore, the initial cell is primed with internal GB1 and surface GB1Receptor by adding these molecules to <InitialChemistry> under <Cell>. The amounts of initial molecules are chosen so that the initial cell contains a GB1 concentration of 10 and the surface GB1Receptor concentration is greater than the concentration of external GB1, making the signal the limiting factor and not the receptor.

To simplify searches for appropriate coefficients in signaling, it is often useful to explicitly make either the signal or the receptor the limiting factor by ensuring an abundance of the other factor. In this case, the cell should be initialized with enough GB1Receptor so that the cell can take in all of the presented external GB1 and maintain an internal GB1 concentration at or above 10, where its effect on gene unit promotion is maximal.

Configuration Example

```
<InitialChemistry>
    GB1 10
    ( GB1Receptor ) 5
</InitialChemistry>
```

All cells in this model are to grow and divide. In undifferentiated cells, only GB1 will internally promote growth and division. The <Genome>, under <Cell>, is established. Its first gene unit, depicted in FIG. 25B, is written for production of Growth and Division molecules upon promotion by GB1. The promotion effect value is adjusted so that growth and division occur in the initial cell and continue in the daughter cells.

Configuration Example

```
<Genome>
[
    [ GB1 0.112 ] [ Growth, Division ]
]
</Genome>
```

To keep the tissue together and minimize drifting and shuffling of cells, cells must adhere to one another and so a non-decaying CellAdhesion molecule is needed. The molecule is defined in the <MoleculeCatalog>:

Configuration Example

CellAdhesion [90, 10] 0.0;

It is also added to the <InitialChemistry> as a surface molecule so that no production expression or equation is necessary:

Configuration Example (CellAdhesion) 0.1

An <AdhesionRule> is added under <Simulation> to associate the surface CellAdhesion molecules of one cell to the surface CellAdhesion molecules of another cell.

Configuration Example

```
<AdhesionRules>
    ( CellAdhesion ) : ( CellAdhesion );
</AdhesionRules>
```

Because of the high pressure situation created by the constrained environment and an intentionally rapidly growing tissue, surrounded cells should grow and divide more slowly than cells on the perimeter. The concept of "contact inhibition" in living tissues can be applied here. To accomplish contact inhibition, cells need to recognize how surrounded they are.

A chemistry equation is added to create internal SurroundedMarker in response to receiving external SurroundedSignal via surface SurroundedReceptor, FIG. 25D. The coefficient on SurroundedMarker (e.g., 2.0) is adjusted through experimentation so that a fully surrounded cell has a concentration of SurroundedMarker near 10, such that promotion of gene units by SurroundedMarker will be high, while a cell with only 1 or 2 neighbors has a SurroundedMarker concentration below 2 or 3, such that promotion of gene units by SurroundedMarker will be very low.

Configuration Example

{SurroundedSignal}+(SurroundedReceptor)=2.0 SurroundedMarker+(Surrounded Receptor);

As always in this example, these molecules are added to the <MoleculeCatalog>. As with GB1Receptor, SurroundedReceptor is not to decay.

Configuration Example

SurroundedSignal [30, 10];
SurroundedReceptor [40, 10] 0.0;
SurroundedMarker [50, 10];

Also as with GB1Receptor, SurroundedReceptor is added to the <InitialChemistry> in sufficient quantity to guarantee that signal amounts will be the limiting factor in signaling:

Configuration Example (SurroundedReceptor) 50

Figure 25C:
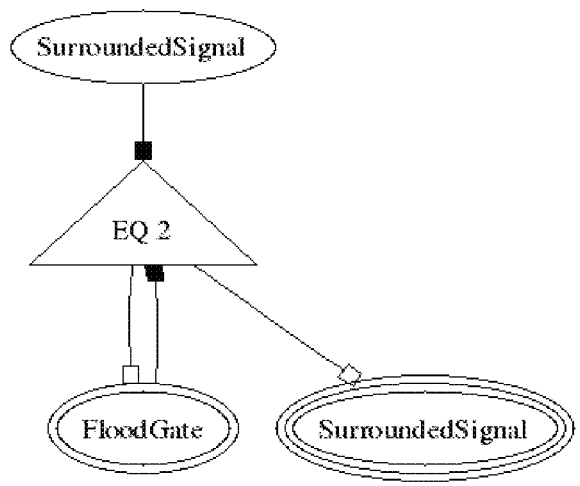
Figure 25G:
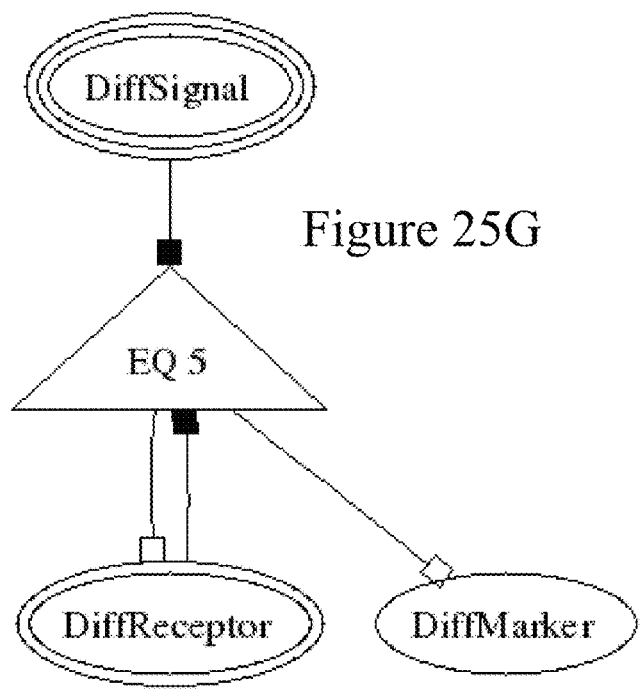
Figure 25H:
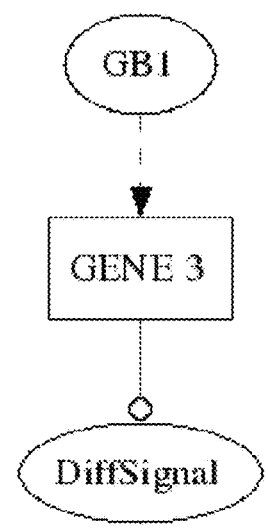
Figure 26:
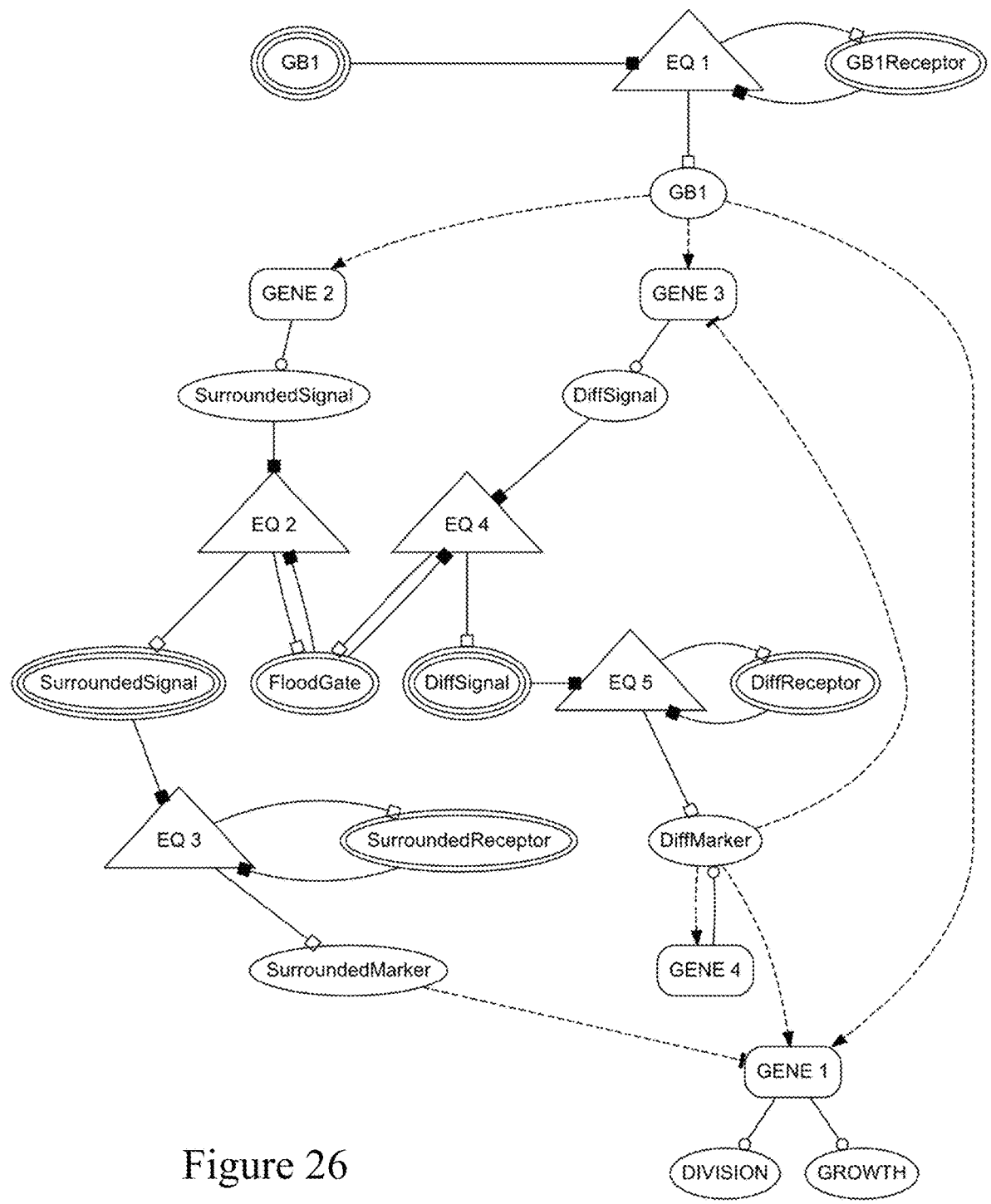
FIG. 26 is a schematic flow diagram illustrating a modeled SGRN for simulating development of a multicellular tissue with stem-cell niches in accordance with the simulation of biological events described in Example 2 of section G2, and in accordance with an embodiment of the disclosure.

Another chemistry equation is added to export internal SurroundedSignal to the environment via a general-purpose surface exporter molecule, FloodGate, FIG. 25C:

Configuration Example

SurroundedSignal+(FloodGate)={SurroundedSignal}+(FloodGate);

FloodGate, as a surface transporter, is added to the <MoleculeCatalog> so as not to decay:

Configuration Example

FloodGate [100, 10] 0.0;
As with the other surface transporters, FloodGate is added to the Initial Chemistry in sufficient quantity to guarantee that signal amounts will be the limiting factor in signaling.

Configuration Example (FloodGate) 50
All cells will send the SurroundedSignal, so a gene unit promoted by GB1 is added to the <Genome> to produce SurroundedSignal, FIG. 25E. The promotion effect value is set to something large enough that signals produced each step will be detectable by neighboring cells, but not so large as to require neighbors to sustain a high concentration of receptors. Practice with the preferred embodiment has indicated that values near 0.125 meet these requirements given these other initial configuration settings.

Configuration Example

[GB1 0.125] [SurroundedSignal]
By the Kepler conjecture regarding maximum packing density of spheres in any three dimensional space, a maximally-surrounded single-sphere cell can receive contact signal from at most twelve single-sphere neighbors (Hales, T. C. (2005). A proof of the Kepler conjecture. *Annals of Mathematics*, 162, 1063-1183). Therefore, for such a cell to be able to distinguish between, say, the maximum number of neighbors and one less than the maximum number of neighbors, its concentration of SurroundedReceptor must be at least 12 times greater than the maximal signal concentration. Internally, the range of SurroundedMarker concentration sustained by receiving from minimum to maximum SurroundedSignal should be between 0 and 10, the effective range of the simulation's configured promotion curve.

To reduce the rate of Growth and Division in surrounded cells, an inhibitory region matching SurroundedMarker is added to the already existing gene unit producing Growth and Division. The promotion and inhibition effect values may need to be balanced so that surrounded cells are still capable of growth and division at a very low rate while perimeter cells grow and divide at a noticeably higher rate. The changed gene unit is now as follows:

Configuration Example

[GB1 0.112, SurroundedMarker −0.001] [Growth, Division],
The configuration written thus far will grow a sheet of adhered cells where the edge cells of the sheet grow and divide more rapidly than those surrounded within:

Configuration Example

```
<CsIndividual>
    <MoleculeCatalog>
        GB1 [10, 10];
        GB1Receptor [20, 10] 0.0;
        SurroundedSignal [30, 10];
        SurroundedReceptor [40, 10] 0.0;
        SurroundedMarker [50, 10];
        CellAdhesion [90, 10] 0.0;
        FloodGate [100, 10] 0.0;
    </MoleculeCatalog>
    <Simulation>
        <MaxInterAdhesionLength>0.25</MaxInterAdhesionLength>
        <SingleAdhesionRule>0</SingleAdhesionRule>
        <Physics>
            <MaxVelocityChange>2</MaxVelocityChange>
            <TimePerStep>0.5</TimePerStep>
            <DampingMultiplier>2</DampingMultiplier>
            <RepulsionMultiplier>2</RepulsionMultiplier>
        </Physics>
        <FixedSpheres>
            [0, −1000, 0] 1000,
            [0, 1001, 0] 1000
        </FixedSpheres>
        <Signal>
            <Local>
                <Separation>0.2</Separation>
            </Local>
        </Signal>
        <Cell>
            <Chemistry><Default/></Chemistry>
            <InitialSize>13</InitialSize>
            <MinimumSize>1</MinimumSize>
            <MaximumSize>2</MaximumSize>
            <InitialChemistry>
                GB1 10
                ( GB1Receptor ) 5
                ( FloodGate ) 50
                ( SurroundedReceptor ) 50
                ( CellAdhesion ) 0.1
            </InitialChemistry>
            <ChemistryEquations>
                { GB1 } + ( GB1Receptor ) = GB1 +
                    ( GB1Receptor );
                SurroundedSignal + ( FloodGate ) =
                    { SurroundedSignal } + ( FloodGate );
                { SurroundedSignal } + ( SurroundedReceptor ) =
                    2.0 SurroundedMarker + ( Surrounded Receptor );
            </ChemistryEquations>
            <Promoter>
                <Smoother>
                    <PromotionMidpoint>5</PromotionMidpoint>
                    <Slope>3</Slope>
                    <ActiveConcentration>1</ActiveConcentration>
                </Smoother>
            </Promoter>
        </Cell>
        <AdhesionRules>
            ( CellAdhesion ) : ( CellAdhesion );
        </AdhesionRules>
    </Simulation>
    <Genome>
    [
        [ GB1 0.112, SurroundedMarker −0.001 ] [ Growth, Division ],
        [ GB1 0.125 ] [ SurroundedSignal ]
    ]
    </Genome>
    <Shade>
        <UseRadius/><UseModifier/>
        [ S GB1 @ 0 0 0 1 0 1 1 ]
    </Shade>
</CsIndividual>
```

From this base model, the signal isolation and differentiation relevant to stem cell formation can now be implemented. Undifferentiated cells are to behave as stem cells and so should not have undifferentiated neighbors but should signal their neighbors to differentiate. Where two or more undifferentiated cells are together, a signaling competition similar to that in the first example should result in only one of the cells remaining undifferentiated.

All cells should be capable of receiving signals to differentiate. A chemistry equation is added to produce DiffMarker in response to receiving external DiffSignal via surface DiffReceptor, FIG. 25G:

Configuration Example

{DiffSignal}+(DiffReceptor)=DiffMarker+(DiffReceptor);

The three molecules are added to the Molecule Catalog with the receptor marked to not decay:

Configuration Example

DiffSignal [60, 10];
DiffReceptor [70, 10] 0.0;
DiffMarker [80, 10];

As with previous receptors, DiffReceptor is added to the Initial Chemistry:

Configuration Example (DiffReceptor) 50

Another equation is added to export internal DiffSignal via surface FloodGate, FIG. 25F:

Configuration Example

DiffSignal+(FloodGate)={DiffSignal}+(FloodGate);

An instruction to produce DiffSignal is not yet written and so this signal pathway will not yet be exercised. Undifferentiated cells need to signal neighbors to differentiate, but differentiated cells should not signal their neighbors. A gene unit producing DiffSignal is added, promoted by GB1, FIG. 25H:

Configuration Example

[GB1 0.4] [DiffSignal]

An inhibiting gene unit matching DiffMarker is still necessary to prevent differentiated cells from signaling. Similar to the way SurroundedSignal and SurroundedMarker were balanced, the effect value promoting DiffSignal in the genome and the coefficient of DiffMarker in the chemistry equation for response to DiffSignal need to be balanced so that a fully surrounded cell has a concentration of DiffMarker near 120: 12 (again, maximum contacting cells) times the concentration of 10 desired in response to signal from a single undifferentiated cell.

Figure 25I:
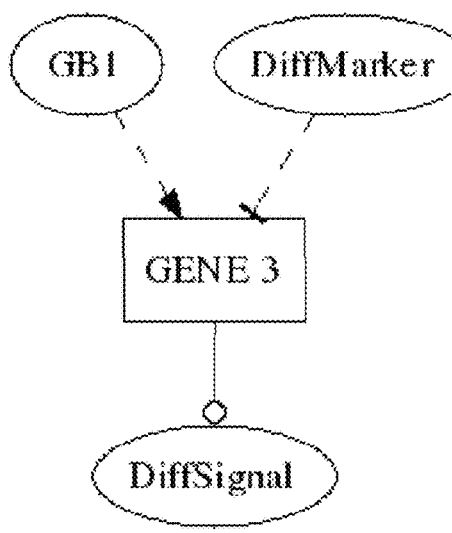

The following instruction amends the gene unit for the balanced inhibition, FIG. 25I. The magnitude of the inhibitory effect should be larger than the promotion effect to ensure that a differentiated cell will not produce and send DiffSignal.

Configuration Example

[GB1 0.4, DiffMarker −0.5] [DiffSignal]

The previously added chemistry equation for importing the signal from the environment is amended to complete the balance:

Configuration Example

{DiffSignal}+(DiffReceptor)=3.0 DiffMarker+(DiffReceptor);

At this point, the model produces isolated undifferentiated cells with low concentrations of DiffMarker surrounded by differentiated cells with high concentrations of DiffMarker. Four factors are balanced to produce the central feature of signal isolation: promotion and inhibition effect values controlling DiffSignal expression, promotion effect of DiffMarker on expression of DiffMarker, and the coefficient on DiffMarker in the Chemistry Equation responding DiffSignal. This is sufficient to meet the basic design requirements, but two more refinements will improve the model's fidelity.

Figure 25J:
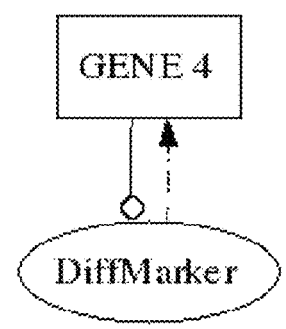
Figure 25K:
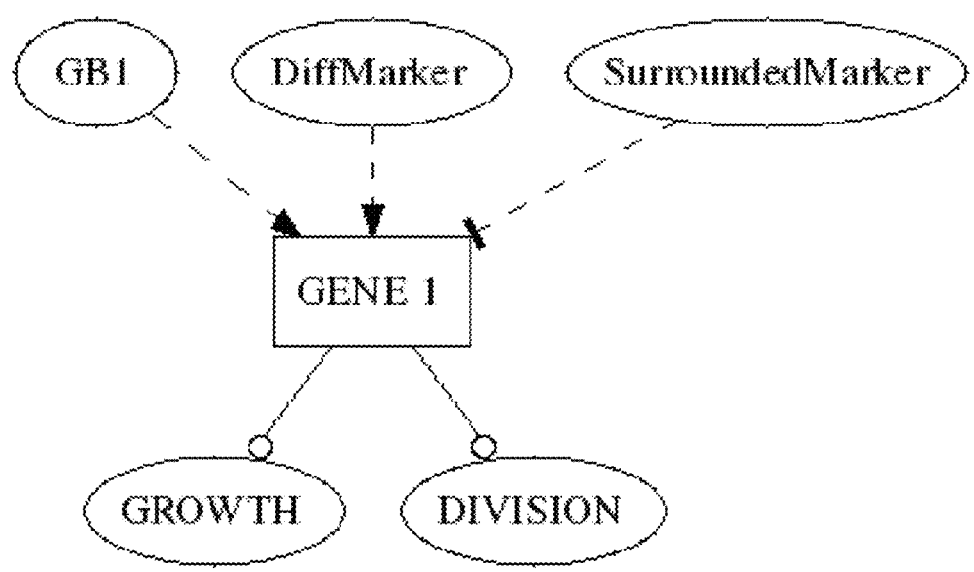

To reinforce the distinction between differentiated and undifferentiated cells and to reduce the likelihood of differentiated cells reverted to an undifferentiated state, a positive reinforcement gene unit for DiffMarker, FIG. 25J, can be added to the <Genome>. The promotion effect value should be as high as possible without allowing a differentiated cell to maintain its concentration of DiffMarker through expression of this gene unit alone.

Configuration Example

[DiffMarker 0.25] [DiffMarker]

As a demonstration of a tangible potential behavioral effect of differentiation and to complete the model requirements from G2.1, differentiating cells in the model can be made to grow and divide more rapidly than undifferentiated cells, analogous to transit-amplifying cell division rates versus stem division rates. This is accomplished by amending the gene unit controlling growth and division to include DiffMarker as a promoter with its effect magnitude similar to the inhibition magnitude of SurroundedMarker, FIG. 25K. In general, all effect values in the assembly are adjusted as necessary to yield the slowest growth by internal undifferentiated cells, slightly faster growth by internal differentiated cells, and the fastest growth by perimeter differentiated cells.

Configuration Example

[GB1 0.112, DiffMarker 0.006, SurroundedMarker −0.001] [Growth, Division],

Once this simple model is working as intended, it can be used as-is or enhanced to explore patterns of signal isolation within a tissue given different signaling ranges and distributions.

In the example discussed above, a resulting configuration is shown below:

```
<CsIndividual>
    <MoleculeCatalog>
        GB1 [10, 10];
        GB1Receptor [20, 10] 0.0;
        SurroundedSignal [30, 10];
        SurroundedReceptor [40, 10] 0.0;
        SurroundedMarker [50, 10];
        DiffSignal [60, 10];
        DiffReceptor [70, 10] 0.0;
        DiffMarker [80, 10];
        CellAdhesion [90, 10] 0.0;
        FloodGate [100, 10] 0.0;
    </MoleculeCatalog>
    <Simulation>
        <MaxInterAdhesionLength>0.25</MaxInterAdhesionLength>
        <SingleAdhesionRule>0</SingleAdhesionRule>
        <Physics>
            <MaxVelocityChange>2</MaxVelocityChange>
            <TimePerStep>0.5</TimePerStep>
            <DampingMultiplier>2</DampingMultiplier>
            <RepulsionMultiplier>2</RepulsionMultiplier>
            <NudgeMagnitude>3</NudgeMagnitude>
        </Physics>
        <FixedSpheres>
```

-continued

```
        [0, -1000, 0] 1000,
        [0, 1001, 0] 1000
    </FixedSpheres>
    <Signal>
        <Local>
            <Separation>0.2</Separation>
        </Local>
    </Signal>
    <Cell>
        <Chemistry><Default/></Chemistry>
        <Promoter>
            <Smoother>
                <PromotionMidpoint>5</PromotionMidpoint>
                <Slope>3</Slope>
                <ActiveConcentration>1</ActiveConcentration>
            </Smoother>
        </Promoter>
        <InitialSize>13</InitialSize>
        <MinimumSize>1</MinimumSize>
        <MaximumSize>2</MaximumSize>
        <InitialChemistry>
            GB1 10
            ( GB1Receptor ) 5
            ( FloodGate ) 50
            ( DiffReceptor ) 50
            ( SurroundedReceptor ) 50
            ( CellAdhesion ) 0.1
        </InitialChemistry>
        <ChemistryEquations>
            { GB1 } + ( GB1Receptor ) = GB1 +
                ( GB1Receptor );
            SurroundedSignal + ( FloodGate ) =
                { SurroundedSignal } + ( FloodGate );
            { SurroundedSignal } + ( SurroundedReceptor ) =
                2.0 SurroundedMarker + ( SurroundedReceptor );
            DiffSignal + ( FloodGate ) = { DiffSignal } +
                ( FloodGate );
            { DiffSignal } + ( DiffReceptor ) =
                3.0 DiffMarker + ( DiffReceptor );
        </ChemistryEquations>
    </Cell>
    <AdhesionRules>
        ( CellAdhesion ) : ( CellAdhesion );
    </AdhesionRules>
</Simulation>
<Genome>
[
    [ GB1 0.125 ] [ SurroundedSignal ],
    [ GB1 0.112, DiffMarker 0.006, SurroundedMarker -0.001 ]
        [ Growth, Division ],
    [ GB1 0.4, DiffMarker -0.5 ] [ DiffSignal ],
        [ DiffMarker 0.25 ] [ DiffMarker ]
]
</Genome>
<Shade>
    <UseRadius/><UseModifier/>
    [ S GB1 @ 0 0 0 1 0 1 1 ]
</Shade>
</CsIndividual>
```

The resulting SGRN from this configuration is given by FIG. 26 and may be read as follows:

Nutrient for this model is provided by the external GB1 molecule which is moved to the interior of a cell via "EQ 1" with surface GB1 Receptors.

Once inside the cell, GB1 promotes each of gene units "GENE 1", "GENE 2", "GENE 3", and "GENE 4". Gene units "GENE 2" and "GENE 3" directly promote division and growth of cells and in the beginning of development provide stimulus for the model to expand.

However, "GENE 1" is also promoted by GB1 to produce SurroundedSignal. When moved to the outside of a given cell by "EQ 2" using surface FloodGate molecules, other cells may receive it. In this way, a cell can signal to others that it exists and so contributes to how surrounded the receiving cell is. The receiving cell accepts SurroundedSignal with "EQ 3" and its own surface SurroundedReceptor. It is received as SurroundedMarker which in turn inhibits "GENE 3" and "GENE 4" and so counteracts the influence of the nutrient.

GB1's promotion of "GENE 4" leads to the production of DiffSignal which also combines with surface FloodGate in "EQ 4" to be transported outside the cell. Other cells receive this through their DiffReceptor surface molecules in "EQ 5" as DiffMarkers. Once in a cell, "GENE 5" amplifies these DiffMarker molecules which go on to contribute to the promotions of "GENE 3" and "GENE 4".

The more a cell is signaled to differentiate, the more it is likely to grow and divide; those cells not so differentiated are essentially rudimentary stem cells. Independent of that dynamic, the more a cell is signaled that it is surrounded, the less it will grow and divide.

G3. Example 3: Virtual Epithelium

The third example applies principles from the previous examples to model epithelial tissue. With the preferred embodiment, several approaches with varying fidelity and complexity can be taken to model more complex subjects such as epithelial tissue: the present example describes only one such solution. It will be appreciated that by practicing development principles applied in this and the previous examples, a range of such solutions can be generated.

FIGS. 23A-23D are isometric views illustrating a modeled epithelial tissue, with the modeled basement membrane highlighted (23A), the modeled tissue's stem cells highlighted (23B), with the modeled cells neighboring the stem cells highlighted (23C), and with a population of modeled lipid-producing cells highlighted (23D) in accordance with an embodiment of the disclosure. This small cross-section of epithelial tissue rests on a slightly irregular basement membrane, highlighted in FIG. 23A. From the same simulation moment as FIG. 23A, the tissue's stem cells are highlighted in FIG. 23B. In FIG. 23C, again from the same simulation moment as FIGS. 23A and 23B, all cells near the stem cells are highlighted. This indicates that any highlighted stem or transit amplifying cells are influenced to suppress their stem character. From a later simulation moment, FIG. 24D highlights the virtual cells producing molecules corresponding to lipids.

G3.1. Describing the Model

FIGS. 27A-27JJ are schematic flow diagrams illustrating molecules and actions, gene units and gene unit products, and chemical-interaction rules for modeling a multicellular epithelial tissue in accordance with the simulation of biological events described in Example 3 of section G3 and in accordance with an embodiment of the disclosure. Living epithelial tissue can be characterized by a constant generation and flow of cells from a basement membrane to its surface. Across the basement membrane, stem cells and transit amplifier cells proliferate. As they do so, they become physically pressured to detach from the membrane. Stem cells adhere most strongly to the basement membrane; as cells differentiate, their attachment to the membrane weakens. Thus, most cells that detach are transit amplifier cells. Cells that detach from the basement continue to differentiate into keratinized cells; these keratinocytes eventually produce fatty oils, called lipids.

The stem cells exist in small groups called niches. As a niche enlarges, the cells on its periphery become transit amplifying cells. Not yet committed to differentiation, these cells retain some stem cell character and so can revert to stem cells. This reversion can happen if the cells stay attached to the basement membrane and find themselves sufficiently far from already established stem cell niches. The establishment and maintenance of stem cell niches is consistent with living stem cell formation in epithelial tissue. Peripheral stem cells are not able to become transit amplifier cells unless there is a sufficiently large population of stem cells nearby. In this model, the niches arise from such stem cells. The stem cells most likely to retain their stem character are those at the center of the niche. Once the niche is reduced in size by peripheral attrition to transit amplifying cells, the central stem cells divide and the process continues.

As the population of keratinocytes increases, they are pushed away from the basement membrane. As they move farther away, they receive less signal from the membrane and begin to produce lipids.

G3.2. Decomposing the Problem to Identify Cell-Level Features

As in the previous examples, descriptions of cell types are listed in Table 6 below.

TABLE 6

| Categorical Examples and Descriptions of Cell Type | |
| --- | --- |
| STEM: | Undifferentiated cell attached to the basement membrane. The initial cell of the simulation is a stem cell. |
| TRANSIT AMPLIFIER: | Cells differentiated from stem cells by detachment from the basement membrane proliferate to produce most of the cells in the simulation. These cells cannot revert to stem cells once detached from the basement membrane. |
| KERATINOCYTE: | Cells that were Transit Amplifier cells will differentiate further when a sufficient distance from the basement membrane. These cells cannot grow or divide nor revert to Transit Amplifier cells. |
| LIPID PRODUCING | Keratinocytes beyond the signaling range of the basement membrane produce lipids. |

Dead cells are simply removed from the simulation to optimize computation. These dead cells are interpreted as those sloughed off in the normal cycle of living epithelial development.

The initial cell starts on a special construct called a Basement Membrane, described further below. The basement membrane is to be the anchor point for the virtual epithelium and corresponds to the basal lamina in vivo. Virtual stem cells are to proliferate in the simulation and produce more cells that can fit on the basement membrane. The cells that detach from the membrane undergo several stages of changes as they are pushed up by younger cells from the basement membrane.

For simplicity and to avoid having to grow a basement membrane, which would have led to growing yet other anatomical structures, a special construct is supported by the preferred embodiment of the ontogeny engine for specification of a basement membrane. This example <BasementMembrane> construct is treated as a large cell of numerous subspheres arranged as a sheet. It is specified with its own genome and chemistry equations and so may be considered as a special initial cell.

G3.3. Writing the Configuration File

The configuration is designed starting from a simulation configuration template, with details interpreted in previous examples and in section E.

Configuration Example

```
<CsIndividual>
    <MoleculeCatalog>
    </MoleculeCatalog>
    <Simulation>
        <Physics>
            <TimePerStep>.2</TimePerStep>
            <DampingMultiplier>1</DampingMultiplier>
            <RepulsionMultiplier>2</RepulsionMultiplier>
            <NudgeMagnitude>3</NudgeMagnitude>
        </Physics>
        <Signal>
            <Local>
                <Separation>.3</Separation>
            </Local>
        </Signal>
        <ECMDefinitionRules></ECMDefinitionRules>
        <Cell>
            <Chemistry><Default/></Chemistry>
            <Promoter>
                <Smoother>
                    <PromotionMidpoint>5</PromotionMidpoint>
                    <Slope>10</Slope>
                    <ActiveConcentration>1</ActiveConcentration>
                </Smoother>
            </Promoter>
            <MaximumSize>50</MaximumSize>
            <InitialSize>8</InitialSize>
            <MinimumSize>6</MinimumSize>
            <ECMProductionRules></ECMProductionRules>
            <InitialChemistry>
            </InitialChemistry>
            <ChemistryEquations>
            </ChemistryEquations>
        </Cell>
    </Simulation>
    <Genome>
    [
    ]
    </Genome>
</CsIndividual>
```

G3.3.1. Establishing a Basement Membrane and Initial Environment

The special <BasementMembrane> construct in the preferred embodiment includes subordinate <Cell> (see E3.6) and <Genome> (see E4) sections separate from those of other cells in the simulation to supply special genome and chemistry equations sufficient to keep its shape and supply it with the desired adhesive and signaling characteristics of an epithelial basement membrane. It also supports a special <Bounds> tag to specify its size and location in the environment. The <Bounds> describes two opposing "corners" of the membrane sheet to be filled with subspheres.

The following adds an inert basement membrane:

Configuration Example

```
<BasementMembrane>
    <Bounds>[-22, -2.5, -5][28, -1.0, 7]</Bounds>
    <Cell>
        <Chemistry><Default/></Chemistry>
        <Promoter>
```

```
        <Smooth>
            <PromotionMidpoint>6</PromotionMidpoint>
            <ActiveConcentration>1</ActiveConcentration>
        </Smooth>
    </Promoter>
    <InitialChemistry>
    </InitialChemistry>
    <ChemistryEquations>
    </ChemistryEquations>
</Cell>
<Genome>
[
]
</Genome>
</BasementMembrane>
```

The initial shape and physical responsiveness of the membrane is given by specifying initial values for Rigidity and Elasticity under <InitialChemistry> for the <BasementMembrane>:

Configuration Example

Rigidity 10
Elasticity 10

As Rigidity and Elasticity are special adhesion factors, the preferred embodiment of the ontogeny engine imposes a constant decay. Therefore, these adhesion molecules must be replenished throughout the simulation. One technique is genetic production of Rigidity and Elasticity. This requires some undecaying internal molecule to promote the production.

First, this internal molecule is defined in the simulation's <MoleculeCatalog>:

Configuration Example

BasementMembrane [8000, 10] 0;
The molecule is then established in the <InitialChemistry> for the <BasementMembrane>:

Configuration Example

BasementMembrane 10
Finally, it is used to constantly promote production of Rigidity and Elasticity by the <Genome> of the <BasementMembrane>:

Configuration Example

[BasementMembrane 2.8][Rigidity],
[BasementMembrane 0.2] [Elasticity]

For this example, a basement membrane is useful for cell signaling so that basal cells can recognize attachment. As with all signals, this is done by moving molecules into the environment with a surface molecule. The following reuses the undecaying BasementMembrane molecule to supply surface molecule in the <InitialChemistry> of the <BasementMembrane>. Since metabolism of a basement membrane is not the subject of the present example and has no analogy in living membranes, there is no need for a mechanism to move an internal molecule to the surface: the molecule can simply be reused.

Configuration Example (BasementMembrane) 10
The above surface molecule will be directly seen as an external molecule by any contacting cell. To allow portions of a cell in contact to the membrane recognize contact proximity, a spontaneous, constant signal from the membrane itself is established. Given that the simulation's local signal distance is less than subsphere radii (see initial configuration template, G3.3), a cell must be in or near contact to receive this signal. The following instruction is added to the <ChemistryEquations> of the <BasementMembrane>:

Configuration Example (BasementMembrane)=(BasementMembrane)+{50 BasementMembraneSignal};

<FixedSpheres> are added below the basement membrane to give it an undulated shape similar to skin epithelium:

Configuration Example

```
<FixedSpheres>
    [0,-5,0] 7,
    [17,-5,0] 7,
    [-17,-5,0] 7,
</FixedSpheres>
```

Large fixed spheres are added around the basement membrane to the above <FixedSpheres> as a virtual container to prevent cells from going beyond the edge of the basement membrane surface:

Configuration Example

[−10000,0,0] 9975,
[10000,0,0] 9975,
[0,0,−10000] 9997.5,
[0,0,10000] 9997.5,
[0, −10000, 0] 9996

To produce a gradient consistent with that of dermal tissue under an undulating basement membrane, new source points must be added below the membrane. This is done by adding a gradient Shade to the simulation with gradient builders:

Configuration Example

```
<Shade>
    <UseRadius/>
    <UseModifier/>
    [
        S [6000,10] @  17 −6 0   10   0.8 1 10,
        S [6000,10] @   0 −6 0   10   0.8 1 10,
        S [6000,10] @ −17 −6 0   10   0.8 1 10
    ]
</Shade>
```

For ease of reference later, an entry matching this new signal's molecular signature is made to the simulation's <MoleculeCatalog> as BasementSignal:

Configuration Example

BasementSignal [6000, 10];
The configuration so far produces an undulated, signaling basement membrane draped over three large spheres with large spheres on its sides to keep the cells from falling off the membrane's edge. Following is an exemplary intermediate configuration from which to begin developing epithelial form and behavior:

```
<CsIndividual>
    <MoleculeCatalog>
        BasementMembrane [8000, 10] 0;
        BasementSignal [6000, 10];
    </MoleculeCatalog>
    <Simulation>
        <Physics>
            <TimePerStep>.2</TimePerStep>
            <DampingMultiplier>1</DampingMultiplier>
            <RepulsionMultiplier>2</RepulsionMultiplier>
            <NudgeMagnitude>3</NudgeMagnitude>
        </Physics>
        <Signal>
            <Local>
                <Separation>.3</Separation>
            </Local>
        </Signal>
        <ECMDefinitionRules></ECMDefinitionRules>
        <BasementMembrane>
            <Bounds>[-22, -2.5, -5][28, -1.0, 7]</Bounds>
            <Cell>
                <Chemistry><Default/></Chemistry>
                <Promoter>
                    <Smooth>
                        <PromotionMidpoint>6
                        </PromotionMidpoint>
                        <ActiveConcentration>1
                        </ActiveConcentration>
                    </Smooth>
                </Promoter>
                <InitialChemistry>
                    Rigidity 10
                    Elasticity 10
                    BasementMembrane 10
                    (BasementMembrane) 10
                </InitialChemistry>
                <ChemistryEquations>
                    (BasementMembrane) =
                        (BasementMembrane) +
                        {50 BasementMembraneSignal };
                </ChemistryEquations>
            </Cell>
            <Genome>
                [
                    [ BasementMembrane 2.8 ][ Rigidity ],
                    [ BasementMembrane .2 ] [ Elasticity ]
                ]
            </Genome>
        </BasementMembrane>
        <Cell>
            <Chemistry><Default/></Chemistry>
            <Promoter>
                <Smoother>
                    <PromotionMidpoint>5</PromotionMidpoint>
                    <Slope>10</Slope>
                    <ActiveConcentration>1</ActiveConcentration>
                </Smoother>
            </Promoter>
            <MaximumSize>50</MaximumSize>
            <InitialSize>8</InitialSize>
            <MinimumSize>6</MinimumSize>
            <ECMProductionRules></ECMProductionRules>
            <InitialChemistry>
            </InitialChemistry>
            <ChemistryEquations>
            </ChemistryEquations>
        </Cell>
        <FixedSpheres>
            [0,-5,0] 7,
            [17,-5,0] 7,
            [-17,-5,0] 7,
            [-10000,0,0] 9975,
            [10000,0,0] 9975,
            [0,0,-10000] 9997.5,
            [0,0,10000] 9997.5,
            [0, -10000, 0] 9996
```

-continued

```
        </FixedSpheres>
    </Simulation>
    <Genome>
        [
        ]
    </Genome>
    <Shade>
        <UseRadius/>
        <UseModifier/>
        [
            S [6000,10] @  17 -6 0   10   0.8 1 10,
            S [6000,10] @   0 -6 0   10   0.8 1 10,
            S [6000,10] @ -17 -6 0   10   0.8 1 10
        ]
    </Shade>
</CsIndividual>
```

G3.3.2. Initial Epithelial Stem Cell

For a cell to be considered a stem cell, a cell will be required to have sufficient Stem molecule. This must be added to the <InitialChemistry> of the starting cell in a sufficient amount to promote gene units to be added later in this example:

Configuration Example

Stem 50

It then must also be added to the <MoleculeCatalog> to not decay:

Configuration Example

Stem [100, 10] 0;

A division rule (see Section E.3.6.7.8.) is added under <Cell> to assure that stem cells divide along the basement membrane; that is, perpendicular to the line between the centers of the contacted membrane subsphere and the contacting cell. Because it is a single rule, the coefficient is arbitrary. To avoid conflicts with tracking the cell state, a new surface molecule, StemBM, is introduced solely for support of this division:

Configuration Example

```
<DivisionRules>
    .1 Stem perpendicular (StemBM);
</DivisionRules>
```

The new molecule StemBM is added to the <MoleculeCatalog> and set to not decay:

Configuration Example

StemBM [180, 10] 0;

Because the initial cell should have this property, StemBM is added to <InitialChemistry> as a surface molecule:

Configuration Example (StemBM) 50

Since an undifferentiated cell must be attached to the basement membrane for it to be considered a stem cell, adhesion rules must be established, under <Simulation>, to attach the initial cell to the basement membrane. Alternatively, the adhesion could equivalently involve Stem molecules moved to the surface instead of the special surface StemBM.

Configuration Example

```
<AdhesionRules>
    ( BasementMembrane ) : ( StemBM );
</AdhesionRules>
```

G3.3.3. Production of Stem Cells and Terminally Differentiated Keratinocytes To promote regular cell shaping, three gene units are added to the <Genome>, depicted in FIGS. 27A, 27B, and 27C. Since the Stem and StemBM molecules will not exist in differentiated cells, a new molecule Cell is made present in all cells for shaping.

Configuration Example

[Cell 0.4][Rigidity],
[Cell 0.2][Elasticity],
[Cell 0.6][Plasticity],

The Cell molecule is now added to the <MoleculeCatalog> to not decay so as to be perpetuated in all cells:

Configuration Example

Cell [400, 10] 0;

For this, the <InitialChemistry> must include Cell in the initial cell:

Configuration Example

Cell 10

Stem cells have the ability to grow and divide and so a gene unit is added to support stem cell growth and division. However, as stem cells differentiate, the Stem molecule will be lost. Therefore, a molecule LegitStem is introduced to control growth and division of stem cells:

Configuration Example

[LegitStem 1] [Division, Growth],

LegitStem's production then is promoted by the presence of Stem and inhibited by transition away from a stem cell. The following gene unit promotes the production of LegitStem molecule when Stem molecule is present and inhibits it in the presence of a Transit molecule, FIG. 27D. The production of the Transit molecules is discussed later in this example.

Configuration Example

[Stem 2, Transit −4] [LegitStem],

In this example model, stem cells can not divide if surrounded by other stem cells. Therefore, the gene unit added earlier can be amended to inhibit growth and division upon contact with other stem cells. For this, the molecule StemContact is introduced. As is typical in this example with the preferred embodiment, the final coefficient for StemContact in this gene unit is determined from iterative experimentation throughout this configuration's development.

Configuration example:

[LegitStem 1, StemContact −0.87] [Division, Growth],

Contact with another stem cell can be determined through detection of a surface molecule that exists on both the subject and contacting stem cells. For this, a chemistry equation using a dedicated molecule StemM is added to produce internal StemContact molecule, FIG. 27E. Again, iterative experimentation establishes its coefficient.

Configuration Example

{StemM}+(StemM)=(StemM)+0.2 StemContact;

Since StemM is to be present in all stem cells, it is added as a non-decaying molecule to the <MoleculeCatalog>:

Configuration Example

StemM [150, 10] 0;

The initial cell is also imbued with StemM as a surface molecule, under <InitialChemistry>:

Configuration Example (StemM) 50

An epithelial stem cell can not grow and divide if it is detached from the basement membrane. The gene unit promoting growth and division is amended once again to be inhibited if the cell has detached, recognized through a Detached molecule. The gene unit controlling growth and division is now complete with three conditions, FIG. 27F:

Configuration Example

[LegitStem 1, StemContact −0.87, Detached −2] [Division, Growth],

The production of Detached is dependent on attachment to the basement membrane. As long as a cell is attached, the molecule should not be produced. When a cell gets pushed off the basement membrane, it produces Detached molecule.

Configuration Example

[StemAttachedToBasement −3.2] [Detached],

Without promotion, Detached will never be produced. The gene unit can be amended with the common Cell molecule to always produce Detached in the absence of attachment to be basement membrane. Later in this example description other amendments to this gene unit are discussed.

Configuration Example

[Cell 1.5, StemAttachedToBasement −3.2] [Detached],

Production of StemAttachedToBasement is produced from contact of a stem cell to the basement membrane. The chemistry equation below establishes a contact signal between the membrane and the cell, FIG. 27G:

Configuration Example

{BasementMembrane}+(StemBM)=(StemBM)+ StemAttachedToBasement;

If a portion of the cell (i.e., one or more subspheres) is not in contact with the membrane, then its reception of signal is dramatically reduced compared to a cell in more complete contact with the membrane. The chemistry equation below moderates this by relying on a signal direct from the membrane to even out the production when portions of a cell are very near to the membrane, FIG. 27H:

Configuration Example

{BasementMembraneSignal}+(StemBM)= (StemBM)+StemAttachedToBasement;

As stem cells divide and fill the basement membrane, daughter cells are forced by physics to detach from the membrane and so begin to differentiate permanently into keratinocytes. From the earlier gene unit producing Detached, such cells produce Detached molecule and so promote stem cells to transition. This is implemented with a chemistry equation, FIG. 27I:

Configuration Example

Stem+(StemBM)+(StemM)+Detached=Detached+5 Keratinocyte;

Since the keratinocytes are terminally differentiated, the internal molecule should not decay; the Keratinocyte molecule is added under the <MoleculeCatalog>:

Configuration Example

Keratinocyte [2000, 10] 0;

Further, as the cells make this transition, they lose their stem cell characteristics. The following chemistry equation consumes the stem cell molecules to implement this loss, FIG. 27J:

Configuration Example

Keratinocyte+Stem+(StemBM)+(StemM)=Keratinocyte;

G3.3.4. Stem Niches and Transit Amplifier Cells

To this point, the model produces only stem cells and keratinocytes. The production of the keratinocytes is limited by the production of the stem cells to produce detached cells. This approach is insufficient to generate the volume of cells needed for model fidelity and does not recognize how living epithelial tissue leverages stem cell production to produce many more cells. Therefore, the mechanisms associated with stem cell niches and transit amplifying cells need to be added to the model configuration.

As described previously in this example and in the second example under G2, stem niches are isolated clusters of stem cells. Potential for stem niches arise and are reinforced as stem cells acquire and keep stem cell neighbors through the following gene unit:

Configuration Example

[Stem 0.7, StemNearby 0.4, NichePotential 0.25] [NichePotential],

The internal molecule StemNearby is the product of a signal from other stem cells. A portion of StemSignal is passed along by a receiving cell to adjoining cells and so is dampened as it travels. A general surface molecule, CellMembrane, acts as a receiver for the StemSignal to produce the internal StemNearby molecule. This chemistry equation is depicted in FIG. 27K:

Configuration Example

{StemSignal}+(CellMembrane)=(CellMembrane)+0.7 StemNearby+{0.5 StemSignal};

From iterative experimentation with the preferred embodiment during the development of the configuration, an adjustment to the decay of StemNearby is suggested. It is specified in the <MoleculeCatalog>.

Configuration Example

StemNearby [2600, 10] 0.5;

As is typical in this example for transport molecules, CellMembrane is marked as nondecaying in the <MoleculeCatalog>:

Configuration Example

CellMembrane [300, 10] 0;

Likewise, CellMembrane is added as a surface molecule to the <InitialChemistry>:

Configuration Example (CellMembrane) 50

Figure 27C:
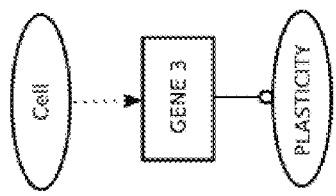
FIGS. 27A-27JJ are schematic flow diagrams illustrating molecules and actions, gene units and gene unit products, and chemical-interaction rules for modeling a multicellular epithelial tissue in accordance with the simulation of biological events described in Example 3 of section G3 and in accordance with an embodiment of the disclosure.
Figure 27B:
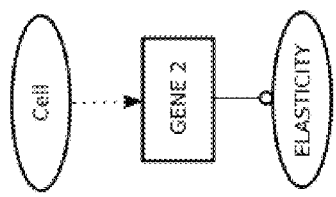
Figure 27A:
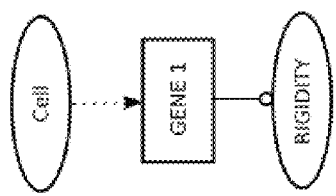
Figure 27E:
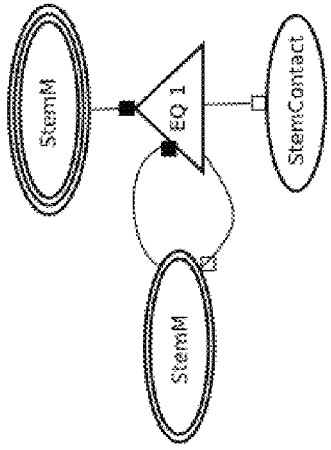
Figure 27G:
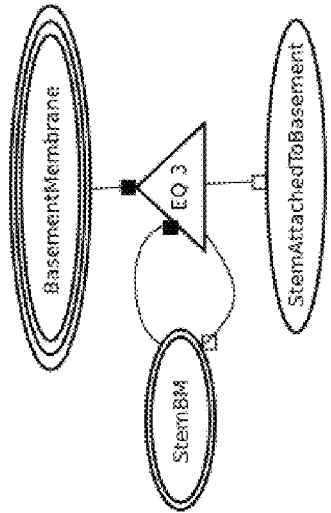
Figure 27D:
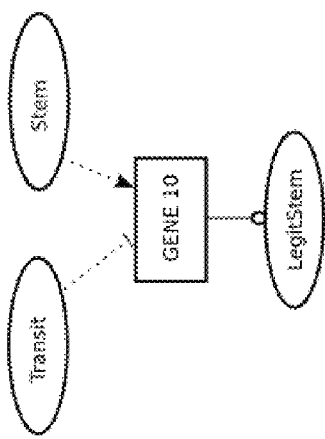
Figure 27F:
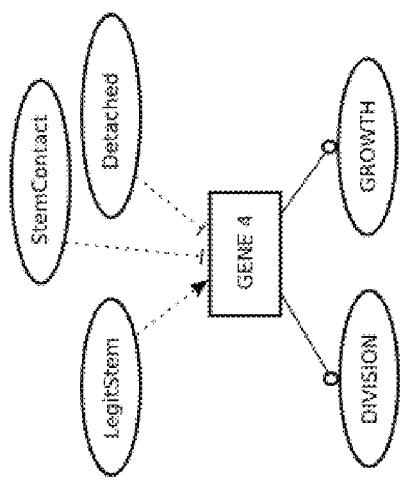
Figure 27I:
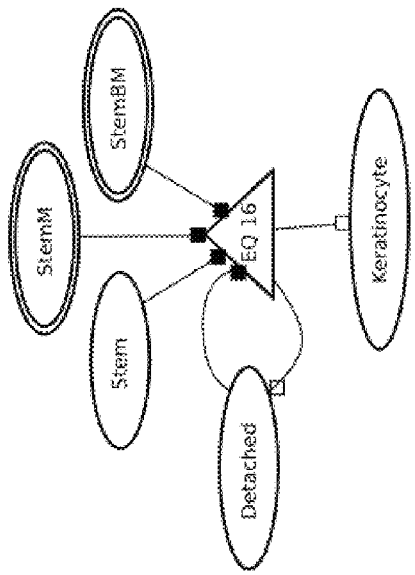
Figure 27K:
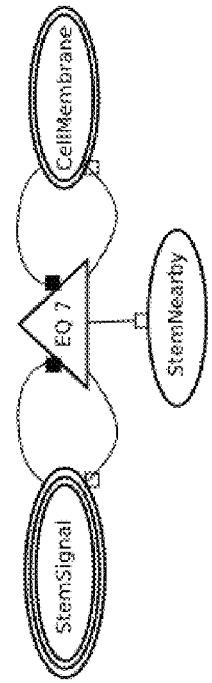
Figure 27H:
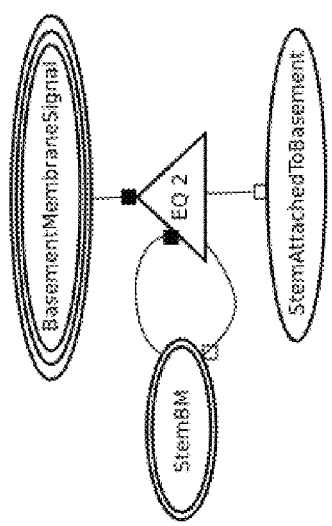
Figure 27J:
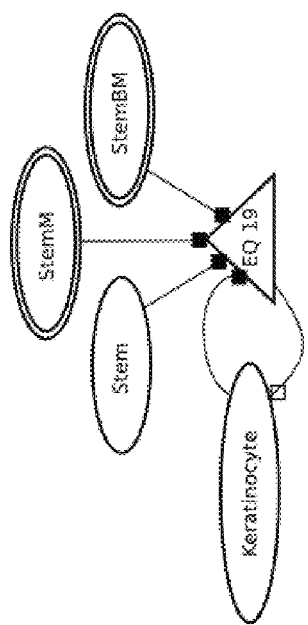
Figure 27M:
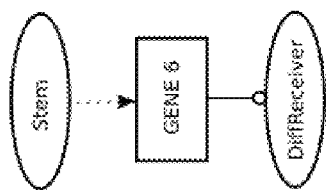
Figure 27O:
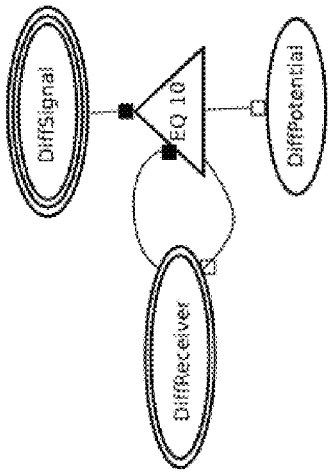
Figure 27L:
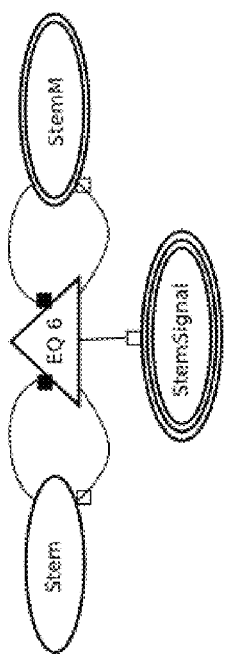

For stem cells to broadcast their proximity, the following chemistry equation, FIG. 27L, causes stem cells to externally produce StemSignal molecule:

Configuration Example

Stem+(StemM)=Stem+(StemM)+{StemSignal};

Stem cells in this example use a similar approach as the previous examples to promote differentiation of other stem cells based on signal competition, and so further separate stem niches. As long as a cell remains a stem cell it produces differentiation receiver molecules via the following gene unit, FIG. 27M:

Configuration Example

Figure 27N:
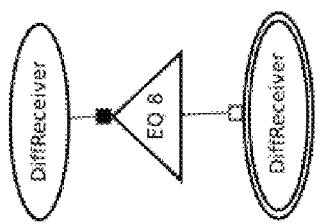

[Stem 2] [DiffReceiver],

A chemistry equation moves the receiver molecule to the cell surface, FIG. 27N:

Configuration Example

DiffReceiver=(DiffReceiver);

Signals received from other cells increase the potential for cell differentiation through a chemistry equation, FIG. 27O:

Configuration Example

Figure 27Q:
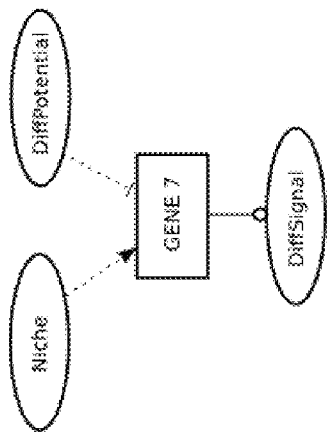
Figure 27S:
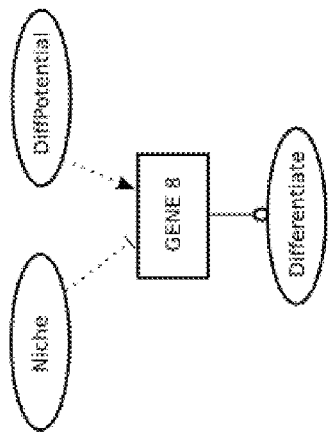
Figure 27P:
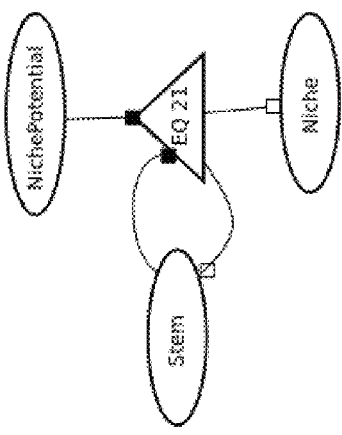

{DiffSignal}+(DiffReceiver)=(DiffReceiver)+2 DiffPotential;

As a cell maintains its stem cell state and gains NichePotential, it gains internal Niche molecule through a chemistry equation, FIG. 27P.

Configuration Example

NichePotential+Stem=Stem+Niche;

As a cell maintains its membership in a stem niche and resists reception of DiffSignal from other cells, it produces more DiffSignal through the following gene unit, FIG. 27Q, to signal neighbor cells to differentiate.

Configuration Example

[Niche 1, DiffPotential −2] [DiffSignal]

Figure 27R:
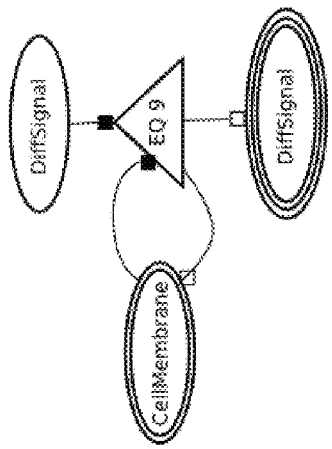

Produced DiffSignal is exported by chemistry equation, FIG. 27R, as a signal through the cell membrane's transport molecule, CellMembrane:

Configuration Example

DiffSignal+(CellMembrane)=(CellMembrane)+{DiffSignal};

As a cell loses membership in a stem niche, accepts more DiffSignal and so gains DiffPotential, it produces more internal Differentiate molecule through the following gene unit, FIG. 27S:

Configuration Example

[DiffPotential 4, Niche −6] [Differentiate]

Increasing DiffPotential should also inhibit a cell's potential to stay with a stem niche. This is done by amending the gene unit for NichePotential added earlier in this section:

Configuration Example

[Stem 0.7, StemNearby 0.4, DiffPotential −3, NichePotential 0.25] [NichePotential], Transit amplifying cells are proliferating cells still attached to the basement membrane but not part of a stem niche. The transition from a stem cell to a transit amplifying cell is not immediate. Before a cell reaches the transit amplifying state and begin proliferating as in FIG. 22, any internal molecules from its stem cell state must be disposed and so a mechanism is required by which the cell progressively gains the potential to proliferate while consuming any remaining molecules related to its prior stem cell state.

Transit molecule represents a cell's state of transition from a stem cell to a transit amplifying state. Transit molecule is configured to not decay with an entry in the <MoleculeCatalog>.

Configuration Example

Transit [1400, 10] 0;

The following chemistry equation, FIG. 27T, converts stem cell molecules to produce transit molecules. The internal Stem molecule, its associated surface StemM and adhesive surface StemBM molecules are consumed with Differentiate to produce internal Transit molecules. TransitM surface molecules, with a coefficient of 0.5, replace StemBM to maintain a weaker adhesion to the membrane. Prolif, discussed later, is also produced and accumulated to support cell proliferation once the transitioning cell becomes a transit amplifier.

Configuration Example

Stem+(StemM)+(StemBM)+Differentiate=Transit+(0.5 TransitM)+0.3 Prolif;

A new <AdhesionRule>, under <Simulation>, establishes TransitM as adhering to the basement membrane:

Configuration Example (BasementMembrane):(TransitM);

Cells in transition should not continue or establish membership in a stem niche and so the gene unit previously added is amended to its final configuration, FIG. 27U:

Configuration Example

[Stem 0.7, Transit −3, StemNearby 0.4, DiffPotential −3, NichePotential 0.25] [NichePotential], Cells that are in the transition process are still subject to differentiation should they detach from the basement membrane. The following equation, FIG. 27V, supports that transition, similar to the equation of FIG. 27I in Section G3.3.3:

Configuration Example

Transit+(0.5 TransitM)+Detached=Detached+5 Keratinocyte;

The cell should be both in transition and a keratinocyte and so will not tolerate the presence of both Transit and Keratinocyte; differentiating cells consume away the Transit molecule, FIG. 27W:

Configuration Example

Figure 27Y:
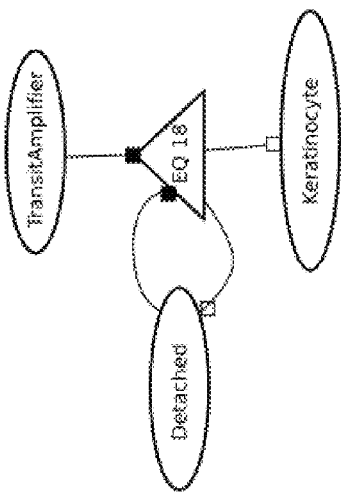
Figure 27A:
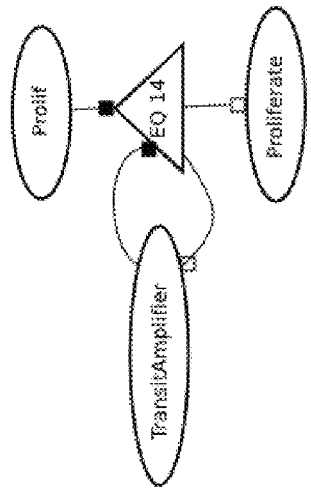
Figure 27X:
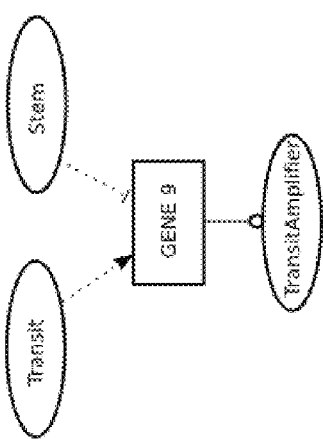

Keratinocyte+Transit=Keratinocyte;

Once a cell has sufficiently transitioned from a stem cell, it has reached a transit amplifying state exhibiting production of TransitAmplifier molecule, FIG. 27X:

Configuration Example

[Transit 2, Stem −4] [TransitAmplifier]

Like other cells (see FIG. 27I and FIG. 27V), transit amplifying cells differentiate into keratinocytes upon detachment, FIG. 27Y:

Configuration Example

Figure 27Z:
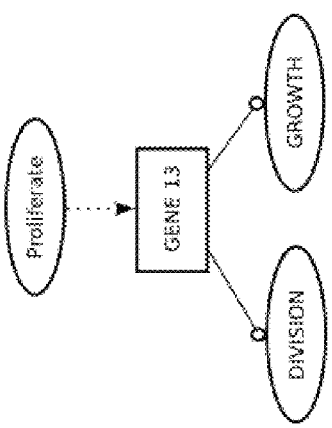
Figure 27C:
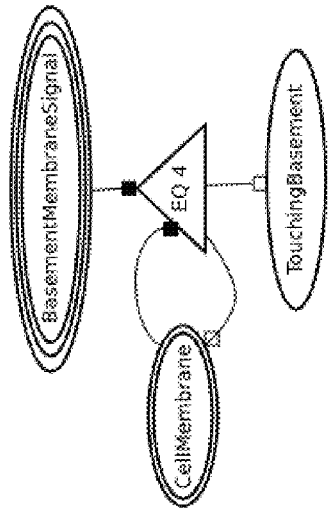
Figure 27B:
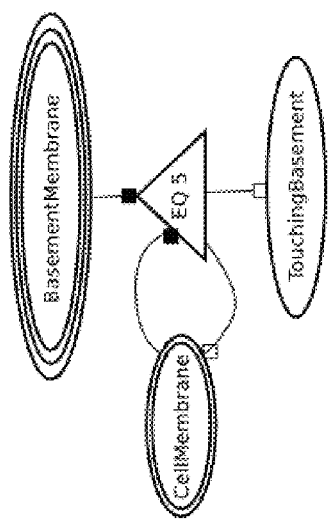
Figure 27E:
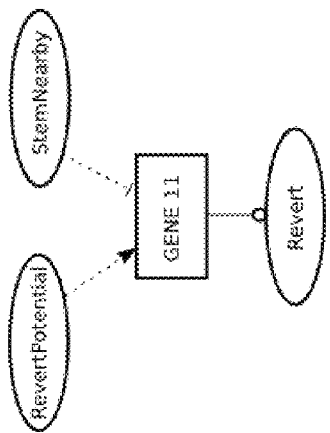
Figure 27D:
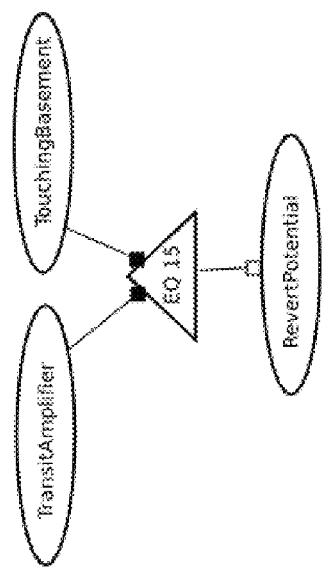
Figure 27F:
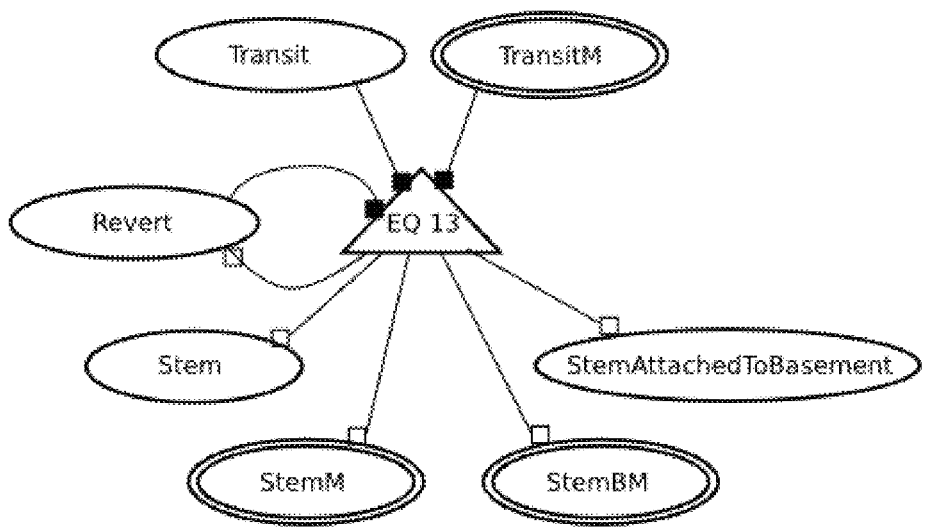
Figure 27H:
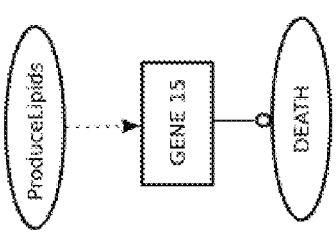
Figure 27J:
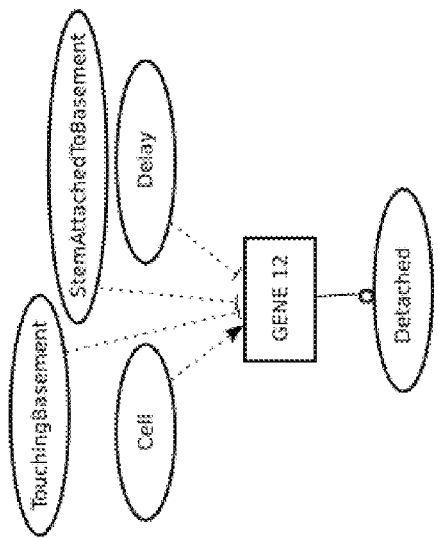
Figure 27G:
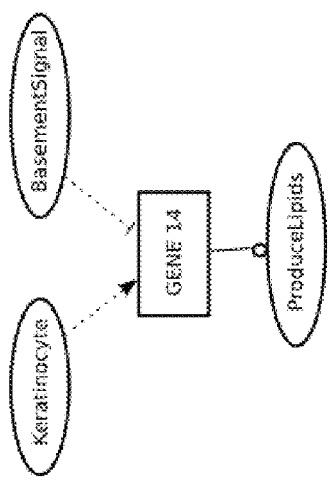
Figure 27I:
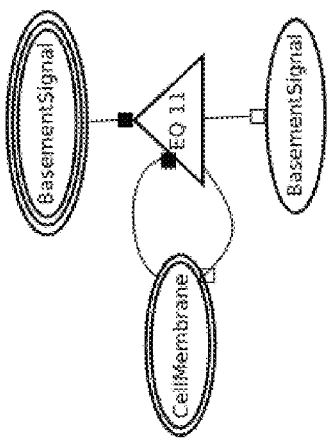

TransitAmplifier+Detached=Detached+5 Keratinocyte;

Upon reaching a transit amplifier state, a cell begins to proliferate. With sufficient Proliferate molecule, the cell rapidly grows and divides, FIG. 27Z. The growth and division continues until the decay of the Proliferate molecule; in the preferred embodiment, this typically lasts three or four rounds of division.

Configuration Example

[Proliferate 2] [Division, Growth]

While in transition, the cell produced Prolif molecule to prepare for this prolific state (see FIG. 27T). The <MoleculeCatalog> includes an entry to prevent decay of the Prolif molecule:

Configuration Example

Prolif [1450, 10] 0;

Once a TransitAmplifier, all of the previously produced Prolif molecule can become Proliferate molecule with the following equation, FIG. 27AA:

Configuration Example

TransitAmplifier+Prolif=TransitAmplifier+Proliferate;

This example began with a single stem cell on the basement membrane. With the pathways described thus far, daughter cells from the initial cell either continue as stem cells in the same initial niche or differentiate to transit amplifying cells or keratinocytes. Therefore, only a single stem cell niche would form for the whole epithelium, yet the model should have some niches at intervals along the membrane. These niches form from transit amplifying cells that revert to stem cells when they are sufficiently far from other stem cells and have not yet detached from the basement membrane.

So far in the configuration file, only the StemAttachedToBasement molecule supports internal recognition of attachment and is only produced will the cell is a stem cell. One solution is to allow all cells to recognize contact with the basement membrane. Similar to those of FIG. 27G and FIG. 27H, these chemistry equations, FIG. 27BB and FIG. 27CC, allow all cells to produce TouchingBasement when in contact with the basement membrane:

Configuration Example

{BasementMembrane}+(CellMembrane)=(CellMembrane)+TouchingBasement;

{BasementMembraneSignal}+(CellMembrane)=(CellMembrane)+TouchingBasement;

Just as with StemAttachedToBasement molecule, the production of Detached should be inhibited by TouchingBasement. The gene unit controlling production of Detached, added in Section G3.3.3, is amended:

Configuration Example

[Cell 1.5, StemAttachedToBasement −3.2, TouchingBasement −3.2] [Detached],

TouchingBasement is given a high (0.5) decay rate in the <MoleculeCatalog>, so that it only exists in the cell while in contact:

Configuration Example

TouchingBasement [2900, 10] 0.5

While a transit amplifier cell is still touching the basement membrane, it gains some potential to revert to stem cells, FIG. 27DD:

Configuration Example

TransitAmplifier+TouchingBasement=10 RevertPotential;

If a cell has sufficient RevertPotential and is far enough away from another stem cell, the following gene unit will cause the cell to begin reversion, FIG. 27EE:

Configuration Example

[RevertPotential 2, StemNearby −4] [Revert]

The reversion process converts a cell's transition molecules (Transit and TransitM) to their stem cell counterparts (Stem, StemM, and StemBM) while maintaining Revert molecule, FIG. 27FF:

Configuration Example

Revert+Transit+(0.5 TransitM)=Stem+(StemM)+(StemBM)+Revert+10 StemAttachedToBasement;

The example configuration now supports stem cell niches and transit amplifying cells. Further, while cells are in transition but still attached, they can establish new stem cell niches if sufficiently distant from other stem cells by reverting.

G3.3.5. Lipid Production and Cell Death

As differentiated cells rise to the surface of the epithelia, the model requires that they begin to produce lipids, eventually die, and slough off.

When the basement membrane was defined in section G3.3.1, gradient signals were added as a <Shade> to represent a general signal from the dermis layer. This signal can be used by cells to recognize their distance from the basement membrane and so begin to produce lipids when sufficiently far.

As keratinocytes are pushed further away from the basement membrane they begin to produce lipids, FIG. 27GG, and eventually die to be sloughed off, FIG. 27HH:

Configuration Example

[Keratinocyte 3, BasementSignal −3] [ProduceLipids],
[ProduceLipids 0.3] [Death]

The cell's reception of the basement signal determines the range of lipid production. This reception can be attenuated as desired by either adjusting the signal gradients under <Shade> or by adjusting the coefficient of the signal received in the cell. The equation below uses the latter technique, FIG. 27II:

Configuration Example

{BasementSignal}+(CellMembrane)=(CellMembrane)+0.9 BasementSignal;

G3.3.6. Completed Example

In accordance with one embodiment, the configuration so far works but the initial cells differentiate too quickly to allow a critical mass of stem cells to form. This can be attenuated by adding a new Delay molecule to the structural region of the gene unit that produces Detached molecule upon cell detachment. FIG. 27JJ depicts the final configuration for this gene unit.

Configuration Example

[Cell 1.5, StemAttachedToBasement −3.2, TouchingBasement −3.2, Delay −5] [Detached], This new Delay molecule must then be added to the <InitialChemistry>:

Configuration Example

Delay 100

With Delay not included in the <MoleculeCatalog>, the default decay rate of 10% will be applied to act as a countdown in the initial cells before they begin to detach. This can be further attenuated by either changing the initial value of the molecule under <InitialChemistry> or adding it under the <MoleculeCatalog> with a different decay rate.

In the example discussed above, a resulting configuration is shown below:

```
<CsIndividual>
    <MoleculeCatalog>
        Stem          [100, 10] 0;
        StemM         [150, 10] 0;
        StemBM        [180, 10] 0;
        CellMembrane  [300, 10] 0;
        Cell          [400, 10] 0;
        Transit       [1400, 10] 0;
        Prolif        [1450, 10] 0;
        Keratinocyte [2000, 10] 0;
        StemNearby [2600, 10] 0.5;
        TouchingBasement [2900, 10] 0.5;
        BasementMembrane [8000, 10] 0;
        BasementSignal [6000, 10];
    </MoleculeCatalog>
    <Simulation>
        <Physics>
            <TimePerStep>.2</TimePerStep>
            <DampingMultiplier>1</DampingMultiplier>
            <RepulsionMultiplier>2</RepulsionMultiplier>
            <NudgeMagnitude>3</NudgeMagnitude>
        </Physics>
        <Signal>
            <Local>
                <Separation>.3</Separation>
            </Local>
        </Signal>
        <ECMDefinitionRules></ECMDefinitionRules>
        <BasementMembrane>
            <Bounds>[-22, -2.5, -5][28, -1.0, 7]</Bounds>
            <Cell>
                <Chemistry><Default/></Chemistry>
                <Promoter>
                    <Smooth>
                        <PromotionMidpoint>6</PromotionMidpoint>
                        <ActiveConcentration>1</ActiveConcentration>
                    </Smooth>
                </Promoter>
                <InitialChemistry>
                    Rigidity 10
                    Elasticity 10
                    BasementMembrane 10
                    (BasementMembrane) 10
                </InitialChemistry>
                <ChemistryEquations>
                    (BasementMembrane) =
                        (BasementMembrane) + { 50 BasementMembraneSignal };
                </ChemistryEquations>
            </Cell>
            <Genome>
            [
                [ BasementMembrane 2.8 ][ Rigidity ],
                [ BasementMembrane .2 ][ Elasticity ]
            ]
            </Genome>
        </BasementMembrane>
        <Cell>
            <Chemistry><Default/></Chemistry>
            <Promoter>
                <Smoother>
                    <PromotionMidpoint>5</PromotionMidpoint>
                    <Slope>10</Slope>
                    <ActiveConcentration>1</ActiveConcentration>
                </Smoother>
            </Promoter>
            <MaximumSize>50</MaximumSize>
            <InitialSize>8</InitialSize>
            <MinimumSize>6</MinimumSize>
            <ECMProductionRules></ECMProductionRules>
            <InitialChemistry>
                Delay 100
                Cell 10
                (CellMembrane) 50
                Stem 50
                (StemM) 50
                (StemBM) 50
            </InitialChemistry>
            <ChemistryEquations>
                { StemM } + (StemM) = (StemM) + .2 StemContact;
                { BasementMembraneSignal } + (StemBM) =
                    (StemBM) + StemAttachedToBasement;
```

```
            { BasementMembrane } + (StemBM) =
                (StemBM) + StemAttachedToBasement;
            { BasementMembraneSignal } + (CellMembrane) =
                (CellMembrane) + TouchingBasement;
            { BasementMembrane } + (CellMembrane) =
                (CellMembrane) + TouchingBasement;
            Stem + (StemM) = Stem + (StemM) + { StemSignal };
            { StemSignal } + (CellMembrane) =
                (CellMembrane) + .7 StemNearby + { .5 StemSignal };
            DiffReceiver = (DiffReceiver);
            DiffSignal + (CellMembrane) = (CellMembrane) + { DiffSignal };
            { DiffSignal } + (DiffReceiver) =
                (DiffReceiver) + 2 DiffPotential;
            {BasementSignal} + (CellMembrane) =
                (CellMembrane) + .9 BasementSignal;
            Stem + (StemM) + (StemBM) + Differentiate =
                Transit + (.5 TransitM) + .3 Prolif;
            Revert + Transit + (.5 TransitM) =
                Stem + (StemM) + (StemBM) + Revert + 10 StemAttachedToBasement;
            TransitAmplifier + Prolif = TransitAmplifier + Proliferate;
            TransitAmplifier + TouchingBasement = 10 RevertPotential;
            Stem + (StemBM) + (StemM) + Detached = Detached + 5 Keratinocyte;
            Transit + (.5 TransitM) + Detached = Detached + 5 Keratinocyte;
            TransitAmplifier + Detached = Detached + 5 Keratinocyte;
            Keratinocyte + Stem + (StemBM) + (StemM) = Keratinocyte;
            Keratinocyte + Transit = Keratinocyte;
            NichePotential + Stem = Stem + Niche;
        </ChemistryEquations>
        <DivisionRules>
            .1 Stem perpendicular (StemBM);
        </DivisionRules>
    </Cell>
    <AdhesionRules>
        ( BasementMembrane ) : ( StemBM );
        ( BasementMembrane ) : ( TransitM );
    </AdhesionRules>
    <FixedSpheres>
        [0,-5,0] 7,
        [17,-5,0] 7,
        [-17,-5,0] 7,
        [-10000,0,0] 9975,
        [10000,0,0] 9975,
        [0,0,-10000] 9997.5,
        [0,0,10000] 9997.5,
        [0, -10000, 0] 9996
    </FixedSpheres>
</Simulation>
<Genome>
[
    [ Cell .4 ][ Rigidity ],
    [ Cell .2 ][ Elasticity ],
    [ Cell .6 ][ Plasticity ],
    [ LegitStem 1, StemContact -0.87, Detached -2 ] [ Division, Growth ],
    [ Stem 0.7,
        Transit -3,
        StemNearby 0.4,
        DiffPotential -3,
        NichePotential .25 ]
        [ NichePotential ],
    [ Stem 2 ] [ DiffReceiver ],
    [ Niche 1, DiffPotential -2 ] [ DiffSignal ],
    [ DiffPotential 4, Niche -6 ] [ Differentiate ],
    [ Transit 2, Stem -4 ] [ TransitAmplifier ],
    [ Stem 2, Transit -4 ] [ LegitStem ],
    [ RevertPotential 2, StemNearby -4 ] [ Revert ],
    [ Cell 1.5,
        StemAttachedToBasement -3.2,
        TouchingBasement -3.2,
        Delay -5 ]
        [ Detached ],
    [ Proliferate 2 ] [ Division, Growth ],
    [ Keratinocyte 3, BasementSignal -3 ] [ ProduceLipids ],
    [ ProduceLipids .3 ] [ Death ]
]
</Genome>
<Shade>
    <UseRadius/>
    <UseModifier/>
    [
```

```
      S [6000,10] @  17 -6 0   10   0.8 1 10,
      S [6000,10] @   0 -6 0   10   0.8 1 10,
      S [6000,10] @ -17 -6 0   10   0.8 1 10
    ]
  </Shade>
</CsIndividual>
```

H. Additional Embodiments of Simulation Systems and Methods

As another example, the cell-centric simulator may be implemented as a computational component for use in directing one or more computing devices to model one or more biological events. Referring to FIG. 29, the computational component may comprise encoded computing device instructions 2922, emanating from a tangible computer readable medium, such as a memory 2920 at a server 2908. The encoded computing device instructions 2922 are electronically accessible to at least one of the computing devices 2902 and 2908 for execution. The computational component may be received at the memory 3002 (FIG. 30) of the computing device 2902 from the server 2908 coupled to the memory 3002 via the network 2906, for example.

The execution of the encoded computing device instructions 2922 may cause the one or more computing devices 2902 and 2908 to receive configurable simulation information. In one embodiment, the configurable simulation information may include user-configurable simulation information received via user interface. In another embodiment, the configurable simulation information can be extracted from a selected configuration file generated during a previous simulation session and stored, for example, in the memory 2920 and/or database 2910.

The execution of the encoded computing device instructions 2922 may further cause the one or more computing devices 2902 and 2908 to initialize an ontogeny engine to an initial step boundary in accordance with the configurable simulation information. The execution of the encoded computing device instructions 2922 may further cause the one or more computing devices 2902 and 2908 to advance the ontogeny engine from a current step boundary to a next step boundary in accordance with the configurable simulation information and the current step boundary. The advancing can include performing a stepCells function. The execution of the encoded computing device instructions 2922 may further cause the one or more computing devices 2902 and 2908 to continue the advancing until a halting condition is encountered. In other embodiments, the advancing can include performing one or more of a killCells function, a stepECM function and stepPhysics function.

Referring to FIG. 30, an operating system (not shown) runs on the processor 3001 and coordinates and provides control of various components within the computing device system 2902. The operating system may be a commonly available operating system such as Microsoft® Windows® XP (Microsoft and Windows are trademarks of Microsoft Corporation in the United States, other countries, or both). A programming system or program interpreter may run in conjunction with the operating system and provide calls to the operating system from these programs or applications executing on computing system 2902.

Instructions for the operating system, the programming system, and applications or programs are located on storage devices, such as a hard disk drive, and may be loaded into the memory 3002 for execution by the processor 3001. The processes of the disclosed illustrative embodiments may be performed by the processor 3001 using computer implemented instructions, which may be located in a memory such as, for example, the memory 3002 or in one or more peripheral devices.

The hardware in computing system 2900 may vary depending on the implementation. Other internal hardware or peripheral devices, such as flash memory, equivalent non-volatile memory, or optical disk drives and the like, may be used in addition to or in place of the hardware depicted in FIG. 29. Also, the processes of the disclosed illustrative embodiments may be applied to a multiprocessor data processing system.

In some illustrative examples, portions of the computing system 2900 may be implemented in a personal digital assistant (PDA), which is generally configured with flash memory to provide non-volatile memory for storing operating system files and/or user-generated data. A bus system may be comprised of one or more buses, such as a system bus, an I/O bus and a PCI bus. Of course the bus system may be implemented using any type of communications fabric or architecture that provides for a transfer of data between different components or devices attached to the fabric or architecture. A communications unit may include one or more devices used to transmit and receive data, such as a modem or a network adapter. A processing unit may include one or more processors or CPUs. The depicted examples in FIGS. 29 and 30 and above-described examples are not meant to imply architectural limitations. For example, portions of the computing system 2900 also may be implemented in a tablet computer, laptop computer, or telephone device in addition to taking the form of a PDA.

Particular embodiments of the computing system 700 can take the form of an entirely hardware embodiment, an entirely software embodiment or an embodiment containing both hardware and software elements. In a particular embodiment, the disclosed methods are implemented in software, which includes but is not limited to firmware, resident software, microcode, etc.

Further, embodiments of the present disclosure, such as the one or more embodiments in FIGS. 1-27 can take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and digital versatile disk (DVD).

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the data processing system either directly or through intervening I/O controllers.

Network adapters may also be coupled to the data processing system to enable the data processing system to become coupled to other data processing systems or remote printers or storage devices through intervening private or public networks. Modems, cable modems, and Ethernet cards are just a few of the currently available types of network adapters.

I. Conclusion

Various embodiments of the technology are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the claims, they may not be described in detail with respect to the Figures. Furthermore, features, structures, or characteristics of various embodiments may be combined in any suitable manner.

Moreover, one skilled in the art will recognize that there are a number of other technologies that could be used to perform functions similar to those described above and so the claims should not be limited to the devices or routines described herein. While processes or blocks are presented in a given order, alternative embodiments may perform routines having steps, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times. The headings provided herein are for convenience only and do not interpret the scope or meaning of the claims.

The terminology used in the description is intended to be interpreted in its broadest reasonable manner, even though it is being used in conjunction with a detailed description of identified embodiments.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

Any patents, applications and other references, including any that may be listed in accompanying filing papers, are incorporated herein by reference. Aspects of the described technology can be modified, if necessary, to employ the systems, functions, and concepts of the various references described above to provide yet further embodiments.

These and other changes can be made in light of the above Detailed Description. While the above description details certain embodiments and describes the best mode contemplated, no matter how detailed, various changes can be made. Implementation details may vary considerably, while still being encompassed by the technology disclosed herein. For example, it will be appreciated how one can simulate biological events, modify the configurable simulation information, and perform additional and/or subsequent simulations, such as those detailed above, using the cell-centric simulation system. Further, it will be recognized that a user can generate user-configurable simulation information to computationally simulate biological events such as development of cellular tissues having a desired phenotype, shape, cell composition, and/or other properties.

As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the claims to the specific embodiments disclosed in the specification, unless the above Detailed Description section explicitly defines such terms. Accordingly, the actual scope of the claims encompasses not only the disclosed embodiments, but also all equivalents.

The previous description of the disclosed embodiments is provided to enable any person skilled in the art to make or use the disclosed embodiments. Various modifications to these embodiments will be readily apparent to those skilled in the art, and the generic principles defined herein may be applied to other embodiments without departing from the scope of the disclosure. Thus, the present disclosure is not intended to be limited to the embodiments shown herein but is to be accorded the widest scope possible consistent with the principles and features as defined by the following claims.

We claim:

1. A computer-implemented method of modeling a biological event comprising:
    receiving configurable simulation information;
    initializing an ontogeny engine to an initial step boundary in accordance with the configurable simulation information;
    advancing the ontogeny engine from a current step boundary to a next step boundary in accordance with the configurable simulation information and the current step boundary, the advancing comprising performing a stepCells function and a stepPhysics function; and
    continuing the advancing until a halting condition is encountered.

2. The method of claim 1 wherein receiving configurable simulation information includes receiving user-configurable simulation information from a user interface.

3. The method of claim 1 wherein receiving configurable simulation information includes receiving a configuration file generated during a first simulation session, and wherein the configuration file is used to model a biological event during a second simulation session.

4. The method of claim 1 wherein continuing the advancing until a halting condition is encountered includes continuing the advancing until a halt command is received from a user interface.

5. The method of claim 1 wherein continuing the advancing until a halting condition is encountered includes continuing the advancing until a configured halting condition is encountered.

6. The method of claim 5 wherein the configured halting condition includes a preset number of advancements by the ontogeny engine from a current step boundary to a next step boundary, and wherein continuing the advancing until a halting condition is encountered includes continuing the advancing until the preset number of advancements has been exhausted.

7. The method of claim 5 wherein the configured halting condition includes a threshold degree of change between a current step boundary and a next step boundary, and wherein continuing the advancing until a halting condition is encountered includes continuing the advancing until the degree of change between a current step boundary and a next step boundary is less than the threshold degree of change.

8. The method of claim 1, further comprising generating a configuration file at the current step boundary, and storing the configuration file for subsequent retrieval.

9. The method of claim 8 wherein:
initializing the ontogeny engine to an initial step boundary includes initializing the ontogeny engine to a first initial step boundary;
the configuration file includes configurable simulation information captured from the current step boundary; and
wherein the method further includes retrieving the configuration file for initializing the ontogeny engine to a second initial step boundary.

10. The method of claim 9 wherein the configuration file is a user-selected configuration file, and wherein receiving configurable simulation information includes receiving the user-selected configuration file and receiving user-defined alteration information for altering the configurable simulation information in the user-selected configuration file.

11. The method of claim 1, wherein the initial step boundary is a first initial step boundary, and wherein the method further comprises:
capturing a configuration file having current step configurable simulation information at the current step boundary;
detecting a dynamic alteration criterion in the configuration file; and
automatically initializing the ontogeny engine to a second initial step boundary in accordance with the current step configurable simulation information and alteration information, the alteration information based on the dynamic alteration criterion.

12. The method of claim 1 wherein advancing further comprises performing a killCells function, and wherein performing a killCells function includes eliminating a virtual cell from a virtual environment.

13. The method of claim 12 wherein eliminating a virtual cell from a virtual environment includes eliminating a virtual cell when a death condition is detected in the virtual cell, and wherein the death condition includes at least one of activation of a death gene unit and deactivation of an essential gene unit in the virtual cell at a previous step.

14. The method of claim 12 wherein advancing further comprises performing a stepECM function, and wherein performing a stepECM function includes at least one of eliminating a cell adhesion and forming a cell adhesion.

15. The method of claim 14 wherein performing a killCells function, a stepCells function, a stepECM function and a stepPhysics function includes performing the killCells function, the stepCells function, the stepECM function and the stepPhysics function simultaneously, thereby modeling the biological event in a continuous manner.

16. The method of claim 1 wherein performing a stepCells function includes invoking at least one of a gene unit control region rule and a chemical-interaction rule for adjusting a level of a molecule.

17. The method of claim 1 wherein performing a stepPhysics function includes invoking a physical interaction rule, and wherein the physical interaction rule applies to at least one of virtual cell adhesion forces, virtual cell overlap resolution and virtual cell movement.

18. The method of claim 17 wherein performing a stepPhysics function includes invoking a physical interaction rule for resolving a virtual cell overlap, and wherein the virtual cell overlap is a result of at least one of virtual cell growth, virtual cell division, and virtual cell motion.

19. The method of claim 1 wherein performing a stepCells function includes metabolic processing, and wherein the metabolic processing includes performing metabolic interaction and genetic transcription calculations.

20. The method of claim 1 wherein receiving configurable simulation information includes receiving information for modeling a biological event in a free-coordinate virtual environment, wherein a virtual cell is represented by a solid sphere, and wherein the virtual cell occupies a non-discrete space in a three-dimensional coordinate arrangement.

21. The method of claim 1 wherein receiving configurable simulation information includes receiving information for modeling a biological event in a free-coordinate virtual environment, wherein a virtual cell is represented by a plurality of subspheres, and wherein the virtual cell occupies a non-discrete space in a three-dimensional coordinate arrangement.

22. The method of claim 1, further comprising displaying at least one of a graphical, a numerical and an alphanumeric representation of data generated at the current step boundary.

23. The method of claim 1, further comprising generating and displaying a graphical image representing the current step boundary at a user interface.

24. The method of claim 23 wherein the graphical image is a first graphical image, and wherein the method further comprises displaying a second graphical image representing the next step boundary, the second graphical image displayed in sequential order following the display of the first graphical image.

25. The method of claim 1 wherein:
initializing an ontogeny engine to an initial step boundary includes independently initializing each of one or more virtual cells in a virtual environment to an initial step boundary; and
advancing the ontogeny engine from a current step boundary to a next step boundary includes advancing each of the one or more virtual cells in the virtual environment independent of each of the other virtual cells, whereby the method achieves modeling a biological event in a continuous manner.

26. The method of claim 1 wherein modeling a biological event includes modeling epithelial tissue growth.

27. The method of claim 1 wherein modeling a biological event includes modeling a process for stem cell differentiation.

28. A non-transitory computer-readable medium encoded with instructions that, when executed by a processor, cause the processor to perform a method comprising:
receiving configurable simulation information;
initializing an ontogeny engine to an initial step boundary in accordance with the configurable simulation information;
advancing the ontogeny engine from a current step boundary to a next step boundary in accordance with the configurable simulation information and the current step boundary, the advancing comprising performing a stepCells function and a stepPhysics function; and
continuing the advancing until a halting condition is encountered.

29. The non-transitory computer-readable medium of claim 28 wherein receiving configurable simulation information includes receiving user-configurable simulation information from a user interface.

30. The non-transitory computer-readable medium of claim 28 wherein continuing the advancing until a halting condition is encountered includes continuing the advancing until a halt command is received from a user interface.

31. The non-transitory computer-readable medium of claim 28 wherein continuing the advancing until a halting condition is encountered includes continuing the advancing until a configured halting condition is encountered.

32. The non-transitory computer-readable medium of claim 31 wherein the configured halting condition includes a preset number of advancements by the ontogeny engine from a current step boundary to a next step boundary, and wherein continuing the advancing until a halting condition is encountered includes continuing the advancing until the preset number of advancements has been exhausted.

33. The non-transitory computer-readable medium of claim 31 wherein the configured halting condition includes a threshold degree of change between a current step boundary and a next step boundary, and wherein continuing the advancing until a halting condition is encountered includes continuing the advancing until the degree of change between a current step boundary and a next step boundary is less than the threshold degree of change.

34. The non-transitory computer-readable medium of claim 28, further comprising generating a configuration file at the current step boundary, and storing the configuration file for subsequent retrieval.

35. The non-transitory computer-readable medium of claim 34 wherein:
initializing the ontogeny engine to an initial step boundary includes initializing the ontogeny engine to a first initial step boundary;
the configuration file includes configurable simulation information captured from the current step boundary; and
wherein the method further includes retrieving the configuration file for initializing the ontogeny engine to a second initial step boundary.

36. The non-transitory computer-readable medium of claim 35 wherein the configuration file is a user-selected configuration file, and wherein receiving configurable simulation information includes receiving the user-selected configuration file and receiving user-defined alteration information for altering the configurable simulation information in the user-selected configuration file.

37. The non-transitory computer-readable medium of claim 28, wherein the initial step boundary is a first initial step boundary, and wherein the method further comprises:
capturing a configuration file having current step configurable simulation information at the current step boundary;
detecting a dynamic alteration criterion in the configuration file; and
automatically initializing the ontogeny engine to a second initial step boundary in accordance with the current step configurable simulation information and alteration information, the alteration information based on the dynamic alteration criterion.

38. The non-transitory computer-readable medium of claim 28 wherein performing a stepCells function includes invoking at least one of a gene unit control region rule and a chemical-interaction rule for adjusting a level of a molecule.

39. The non-transitory computer-readable medium of claim 38 wherein advancing further comprises performing a killCells function for eliminating a virtual cell from a virtual environment, and wherein eliminating a virtual cell from a virtual environment includes detecting a death condition in the virtual cell and, following detection, removing the cell.

40. The non-transitory computer-readable medium of claim 28 wherein advancing further comprises performing a stepECM function, and wherein performing a step ECM function includes at least one of eliminating a cell adhesion between one or more non-adjacent virtual cells and forming a cell adhesion between one or more adjacent virtual cells.

41. The non-transitory computer-readable medium of claim 28 wherein performing a stepPhysics function includes invoking a physical interaction rule, and wherein the physical interaction rule applies to at least one of virtual cell adhesion forces, virtual cell overlap resolution and virtual cell movement.

42. The non-transitory computer-readable medium of claim 41 wherein performing a stepPhysics function includes invoking a physical interaction rule for resolving a virtual cell overlap, and wherein the virtual cell overlap is a result of at least one of virtual cell growth, virtual cell division, and virtual cell motion.

43. The non-transitory computer-readable medium of claim 28 wherein receiving configurable simulation information includes receiving information for modeling a biological event in a fixed-coordinate, virtual environment in which virtual cells occupy discrete spaces in a predetermined coordinate arrangement.

44. The non-transitory computer-readable medium of claim 28 wherein receiving configurable simulation information includes receiving information for modeling a biological event in a free-coordinate virtual environment, wherein a virtual cell is represented by a solid sphere, and wherein the virtual cell occupies a non-discrete space in a three-dimensional coordinate arrangement.

45. The non-transitory computer-readable medium of claim 28 wherein receiving configurable simulation information includes receiving information for modeling a biological event in a free-coordinate virtual environment, wherein a virtual cell is represented by a plurality of subspheres, and wherein the virtual cell occupies a non-discrete space in a three-dimensional coordinate arrangement.

46. The non-transitory computer-readable medium of claim 28, further comprising displaying at least one of a graphical, a numerical and an alphanumeric representation of data generated at the current step boundary.

47. The non-transitory computer-readable medium of claim 28, further comprising generating and displaying a graphical image representing the current step boundary at a user interface.

48. The non-transitory computer-readable medium of claim 47 wherein the graphical image is a first graphical image, and wherein the method further comprises displaying a second graphical image representing the next step boundary, the second graphical image displayed in sequential order following the display of the first graphical image.

49. The non-transitory computer-readable medium of claim 28 wherein:
initializing an ontogeny engine to an initial step boundary includes independently initializing each of one or more virtual cells in a virtual environment to an initial step boundary; and
advancing the ontogeny engine from a current step boundary to a next step boundary includes advancing each of the one or more virtual cells in the virtual environment independent of each of the other virtual cells, whereby the method achieves modeling a biological event in a continuous manner.

50. The non-transitory computer-readable medium of claim 28 wherein modeling a biological event includes modeling epithelial tissue growth.

51. The non-transitory computer-readable medium of claim 28 wherein modeling a biological event includes modeling a process for stem cell differentiation.

52. A system for modeling a biological event, comprising:
a processor;
a receive module configured to execute on the processor and receive configurable simulation information;
an initialize module configured to execute on the processor and initialize an ontogeny engine to an initial step boundary in accordance with the configurable simulation information;
an advance module configured to execute on the processor and advance the ontogeny engine from a current step boundary to a next step boundary in accordance with the configurable simulation information and the current step boundary, the advancing comprising performing a stepCells function and a stepPhysics function; and
a halt detection module configured to execute on the processor and continue the execution of the advance module until a halting condition is encountered.

53. The system of claim 52 wherein the receive module is configured to receive user-configurable simulation information from a user interface.

54. The system of claim 52 wherein the receive module is configured to receive a configurable file from a first modeling run to initiate modeling of a second biological event.

55. The system of claim 52 wherein the halting condition is a halt command received from a user interface.

56. The system of claim 52 wherein the halting condition is a configured halting condition, and wherein the halt detection module continues the execution of the advance module until the configured halting condition is encountered.

57. The system of claim 56 wherein the configured halting condition includes a preset number of advancements by the ontogeny engine from a current step boundary to a next step boundary, and wherein the halt detection module can halt the advancement module when the preset number of advancements has been exhausted.

58. The system of claim 56 wherein the configured halting condition includes a threshold degree of change between a current step boundary and a next step boundary, and wherein the halt detection module can halt the advancement module when the degree of change between a current step boundary and a next step boundary is less than the threshold degree of change.

59. The system of claim 52, further comprising means for generating a configuration file at the current step boundary, and means for storing the configuration file for subsequent retrieval.

60. The system of claim 59 wherein:
the initial step boundary is a first initial step boundary;
the configuration file includes configurable simulation information captured from the current step boundary, and wherein the system further comprises means for retrieving the configuration file;
the receive module is further configured to receive the configuration file; and
the initialization module is further configured to initialize the ontogeny engine to a second initial step boundary in accordance with the configurable simulation information captured from the current step boundary.

61. The system of claim 60 wherein the configuration file is a user-selected configuration file, and wherein the receive module is configured to receive the user-selected configuration file and receive user-defined alteration information for altering the configurable simulation information captured from the current step boundary.

62. The system of claim 52 wherein the initial step boundary is a first initial step boundary, and wherein the system further comprises a dynamic adjustment module configured to:
execute on the processor;
capture a configuration file having current step configurable simulation information at the current step boundary; and
detect a dynamic alteration criterion in the configuration file, wherein the initialization module is further configured to initialize the ontogeny engine to a second initial step boundary in accordance with the current step configurable simulation information and alteration information, the alteration information based on the dynamic alteration criterion.

63. The system of claim 52 wherein:
the advancing further includes a killCells function configured to eliminate a virtual cell from a virtual environment and a stepECM function is configured to invoke a rule for at least one of eliminating a cell adhesion and forming a cell adhesion;
the stepCells function is configured to invoke at least one of a gene unit control region rule and a chemical-interaction rule for adjusting a level of a molecule; and
the stepPhysics function is configured to invoke a physical interaction rule.

64. The system of claim 63 wherein the physical interaction rule for resolving a virtual cell overlap, and wherein the virtual cell overlap is a result of at least one of virtual cell growth, virtual cell division and virtual cell motion.

65. The system of claim 52, further comprising a visualization engine for displaying at least one of a graphical, a numerical and an alphanumeric representation of data generated at the current step boundary.

66. The system of claim 52, further comprising a visualization engine configured to generate and display a graphical image representing the current step boundary at a user interface.

67. The system of claim 66 wherein the graphical image is a first graphical image, and wherein the visualization engine is configured to display a second graphical image representing the next step boundary, the second graphical image displayed in sequential order following the display of the first graphical image.

68. A computational component for directing one or more computing devices to model a biological event, the computational component comprising a non-transitory computer readable medium comprising encoded computing device instructions, the encoded computing device instructions electronically accessible to at least one of the one or more computing devices for execution, the instructions configured to cause the one or more computing devices to perform a method, the method comprising:
receiving configurable simulation information;
initializing an ontogeny engine to an initial step boundary in accordance with the configurable simulation information;
advancing the ontogeny engine from a current step boundary to a next step boundary in accordance with the configurable simulation information and the current step boundary, the advancing comprising performing a killCells function, a stepCells function, a stepECM function and a stepPhysics function; and
continuing the advancing until a halting condition is encountered.

69. The computational component of claim 68 wherein receiving configurable simulation information includes receiving user-configurable simulation information from a user interface.

70. The computational component of claim 68 wherein continuing the advancing until a halting condition is encountered includes continuing the advancing until a halt command is received from a user interface.

71. The computational component of claim 68 wherein continuing the advancing until a halting condition is encountered includes continuing the advancing until a configured halting condition is encountered.

72. The computational component of claim 71 wherein the configured halting condition includes a preset number of advancements by the ontogeny engine from a current step boundary to a next step boundary, and wherein continuing the advancing until a halting condition is encountered includes continuing the advancing until the preset number of advancements has been exhausted.

73. The computational component of claim 71 wherein the configured halting condition includes a threshold degree of change between a current step boundary and a next step boundary, and wherein continuing the advancing until a halting condition is encountered includes continuing the advancing until the degree of change between a current step boundary and a next step boundary is less than the threshold degree of change.

74. The computational component of claim 68, further comprising generating a configuration file at the current step boundary, and storing the configuration file for subsequent retrieval.

75. The computational component of claim 74 wherein:
initializing the ontogeny engine to an initial step boundary includes initializing the ontogeny engine to a first initial step boundary;
the configuration file includes configurable simulation information captured from the current step boundary; and
wherein the method further includes retrieving the configuration file for initializing the ontogeny engine to a second initial step boundary.

76. The computational component of claim 75 wherein the configuration file is a user-selected configuration file, and wherein receiving configurable simulation information includes receiving the user-selected configuration file and receiving user-defined alteration information for altering the configurable simulation information in the user-selected configuration file.

77. The computational component of claim 68, wherein the initial step boundary is a first initial step boundary, and wherein the method further comprises:
capturing a configuration file having current step configurable simulation information at the current step boundary;
detecting a dynamic alteration criterion in the configuration file; and
automatically initializing the ontogeny engine to a second initial step boundary in accordance with the current step configurable simulation information and alteration information, the alteration information based on the dynamic alteration criterion.

78. The computational component of claim 68 wherein:
performing a killCells function includes eliminating a virtual cell from a virtual environment, and wherein eliminating a virtual cell from a virtual environment includes eliminating a virtual cell when a death condition is detected in the virtual cell; and
performing a stepCells function includes invoking at least one of a gene unit control region rule and a chemical-interaction rule for adjusting a level of a molecule.

79. The computational component of claim 78 wherein the death condition includes at least one of activation a death gene unit and deactivation of an essential gene unit in the virtual cell at a previous step.

80. The computational component of claim 68 wherein performing a stepECM function includes invoking a rule for eliminating a cell adhesion between one or more non-adjacent virtual cells and forming a cell adhesion between one or more adjacent virtual cells.

81. The computational component of claim 68 wherein performing a stepPhysics function includes invoking a physical interaction rule, and wherein the physical interaction rule applies to at least one of virtual cell adhesion forces, virtual cell overlap resolution and virtual cell movement.

82. The computational component of claim 81 wherein performing a stepPhysics function includes invoking a physical interaction rule for resolving a virtual cell overlap, and wherein the virtual cell overlap is a result of at least one of virtual cell growth, virtual cell division, and virtual cell motion.

83. The computational component of claim 68 wherein receiving configurable simulation information includes receiving information for modeling a biological event in a fixed-coordinate, virtual environment in which virtual cells occupy discrete spaces in a predetermined coordinate arrangement.

84. The computational component of claim 68 wherein receiving configurable simulation information includes receiving information for modeling a biological event in a free-coordinate virtual environment, wherein a virtual cell is represented by a solid sphere, and wherein the virtual cell occupies a non-discrete space in a three-dimensional coordinate arrangement.

85. The computational component of claim 68 wherein receiving configurable simulation information includes receiving information for modeling a biological event in a free-coordinate virtual environment, wherein a virtual cell is represented by a plurality of subspheres, and wherein the virtual cell occupies a non-discrete space in a three-dimensional coordinate arrangement.

86. The computational component of claim 68, further comprising displaying at least one of a graphical, a numerical and an alphanumeric representation of data generated at the current step boundary.

87. The computational component of claim 68, further comprising generating and displaying a graphical image representing the current step boundary at a user interface.

88. The computational component of claim 87 wherein the graphical image is a first graphical image, and wherein the method further comprises displaying a second graphical image representing the next step boundary, the second graphical image displayed in sequential order following the display of the first graphical image.

89. The computational component of claim 68 wherein:
   initializing an ontogeny engine to an initial step boundary includes independently initializing each of one or more virtual cells in a virtual environment to an initial step boundary; and
   advancing the ontogeny engine from a current step boundary to a next step boundary includes advancing each of the one or more virtual cells in the virtual environment independent of each of the other virtual cells, whereby the method achieves modeling a biological event in a continuous manner.

90. The computational component of claim 68 wherein performing a killCells function, a stepCells function, a stepECM function and a stepPhysics function includes performing the killCells function, the stepCells function, the stepECM function and the stepPhysics function simultaneously, thereby modeling the biological event in a continuous manner.

91. The computational component of claim 68 wherein modeling a biological event includes modeling epithelial tissue growth.

92. The computational component of claim 68 wherein modeling a biological event includes modeling a process for stem cell differentiation.

* * * * *